United States Patent
Takahashi et al.

(10) Patent No.: US 11,208,429 B2
(45) Date of Patent: Dec. 28, 2021

(54) MODIFIED NUCLEIC ACID MONOMER COMPOUND AND OLIGONUCLEIC ACID ANALOG

(71) Applicant: EISAI R&D MANAGEMENT CO., LTD., Tokyo (JP)

(72) Inventors: Yoshinori Takahashi, Ibaraki (JP); Yuta Suzuki, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 80 days.

(21) Appl. No.: 16/616,693

(22) PCT Filed: Jun. 14, 2018

(86) PCT No.: PCT/JP2018/022663
§ 371 (c)(1),
(2) Date: Nov. 25, 2019

(87) PCT Pub. No.: WO2018/230624
PCT Pub. Date: Dec. 20, 2018

(65) Prior Publication Data
US 2020/0216488 A1 Jul. 9, 2020

(30) Foreign Application Priority Data
Jun. 16, 2017 (JP) .............................. JP2017-118572

(51) Int. Cl.
| | | |
|---|---|---|
| *C07H 21/02* | (2006.01) | |
| *C07H 21/04* | (2006.01) | |
| *C07D 239/54* | (2006.01) | |
| *C07D 239/47* | (2006.01) | |
| *C07D 473/34* | (2006.01) | |
| *C07D 473/18* | (2006.01) | |

(52) U.S. Cl.
CPC ........... *C07H 21/02* (2013.01); *C07D 239/47* (2013.01); *C07D 239/54* (2013.01); *C07D 473/18* (2013.01); *C07D 473/34* (2013.01); *C07H 21/04* (2013.01)

(58) Field of Classification Search
CPC ...... C07H 21/02; C07H 21/04; C07D 239/47; C07D 239/54; C07D 473/18; C07D 473/34
USPC ......................................................... 544/277
See application file for complete search history.

(56) References Cited

U.S. PATENT DOCUMENTS

| | | |
|---|---|---|
| 5,637,684 A | 6/1997 | Cook et al. |
| 10,023,863 B2 | 7/2018 | Templin et al. |

FOREIGN PATENT DOCUMENTS

| | | |
|---|---|---|
| JP | 09-509663 | 9/1997 |
| JP | 10-508312 | 8/1998 |
| JP | 2016-130232 | 7/2016 |
| WO | WO 1996/014330 | 5/1996 |
| WO | WO 2011/139710 | 11/2011 |
| WO | WO 2013/061295 | 5/2013 |

OTHER PUBLICATIONS

Boyode et al., "Synthesis of acyclic nucleoside 5-Ocarbonyl uracil derivative," Journal de la Société Ouest Africaine de Chimie, 2009, 14(28):61-66.
Colombo et al., "Pharmacogenomics and analogues of the antitumour agent $N^6$-isopentenyladenosine," International Journal of Cancer, 2009, 124(9):2179-2185.
Fire et al., "Potent and Specific genetic interference by double-stranded RNA in Caenorhabditis elegans," Nature, 1998, 391:806-811.
International Preliminary Report on Patentability in International Application No. PCT/JP2018/022663, dated Dec. 17, 2019, 13 pages (with English Translation).
International Search Report and Written Opinion in International Application No. PCT/JP2018/022663, dated Jul. 17, 2018, 14 pages (with English Translation).
Kashida et al., "Control of the Chirality and Helicity of Oligomers of Serinol Nucleic Acid (SNA) by Sequence Design," Angewandte Chemie International Edition, 2011, 50(6): 1285-1288.
Kim et al., "Acyclic Analogues of Deoxyadenosine 3', 5'-Bisphosphates as $P2Y_1$ Receptor Antagonists," Journal of Medicinal Chemistry, 2000, 43(4):746-755.
Martin et al., "Synthesis and Anti-Herpes-Virus Activity of Acyclic 2'-Deoxyguanosine Analogues Related to 9-[(1, 3-Dihydroxy-2-propoxy) methyl] guanine," Journal of Medicinal Chemistry, 1986, 29(8):1384-1389.
Ogilvie et al., "Synthesis of Purine and Pyrimidine Trihydroxyacyclonucleosides," Nucleosides & Nucleotides, 1984, 3(5):537-547.
Pasternak et al., "Unlocked nucleic acid—an RNA modification with broad potential," Organic & Biomolecular Chemistry, 2011, 9:3591-3597.
European Extended Search Report in European Patent Application No. 18817223.3, dated Dec. 8, 2020, 9 pages.
Jin et al., "Nanoassemblies containing a fluorouracil/zidovudine glyceryl prodrug with phospholipase $A_2$-triggered drug release for cancer treatment," Colloids and Surfaces B: Biointerfaces, 2013, 112:421-428.
Office Action in Indian Patent Application No. 201947048761, dated Jun. 29, 2021, 5 pages (with English Translation).
Response to European Extended Search Report in European Patent Application No. 18817223.3, dated May 28, 2021, 23 pages.
Seela et al., "Oligodeoxyribonucleotides containing 1,3-propanediol as nucleoside substitute," Nucleic Acids Research, 1987, 15(7):3113-3129.

(Continued)

*Primary Examiner* — Kristin A Vajda
(74) *Attorney, Agent, or Firm* — Fish & Richardson P.C.

(57) ABSTRACT

The present invention provides a modified nucleic acid monomer compound having a specific backbone such as 2-ethylglycerol or methoxymethyl-1,3-propanediol backbone instead of a ribose or deoxyribose backbone of a nucleoside, and an oligonucleic acid analogue containing the monomer compound as at least one of building blocks. The oligonucleic acid analogue containing the nucleic acid monomer compound of the present invention allows provision of an oligonucleic acid analogue having excellent biological stability and/or target gene silencing activity.

7 Claims, 2 Drawing Sheets

Specification includes a Sequence Listing.

(56) References Cited

OTHER PUBLICATIONS

Search Report and Written Opinion in Singaporean Patent Application No. 11201911182X, dated Jan. 20, 2021, 10 pages.
Response to Written Opinion in Singaporean Appln. No. 11201911182X, dated May 12, 2021, 22 pages.
Office Action in European Patent Application No. 18817223.3, dated Oct. 22, 2021, 4 pages.

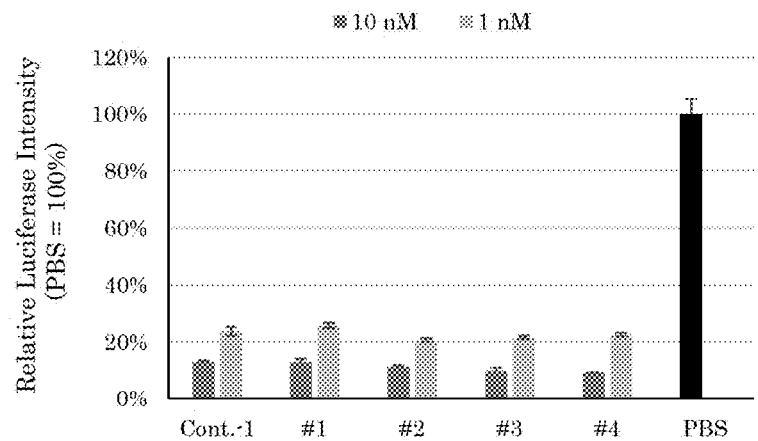
Fig. 1 Dual luciferase reporter assay using modified Luciferase siRNAs in HEK 293 cells
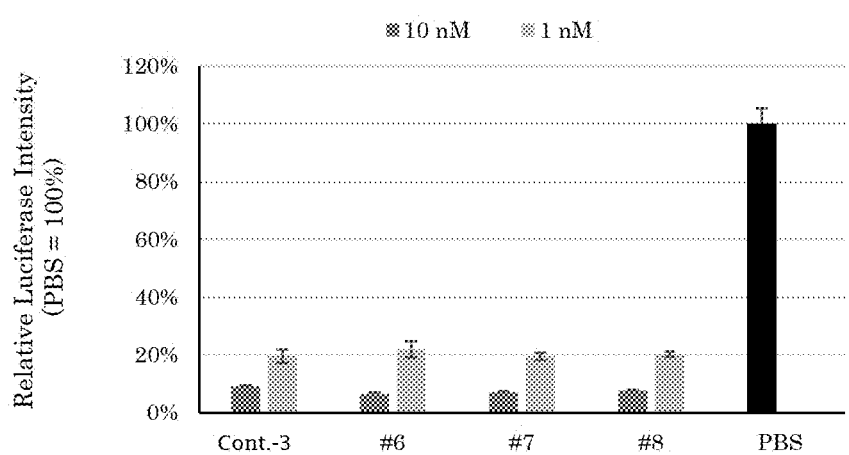
Fig. 2 Dual luciferase reporter assay using modified Luciferase siRNAs in HEK 293 cells

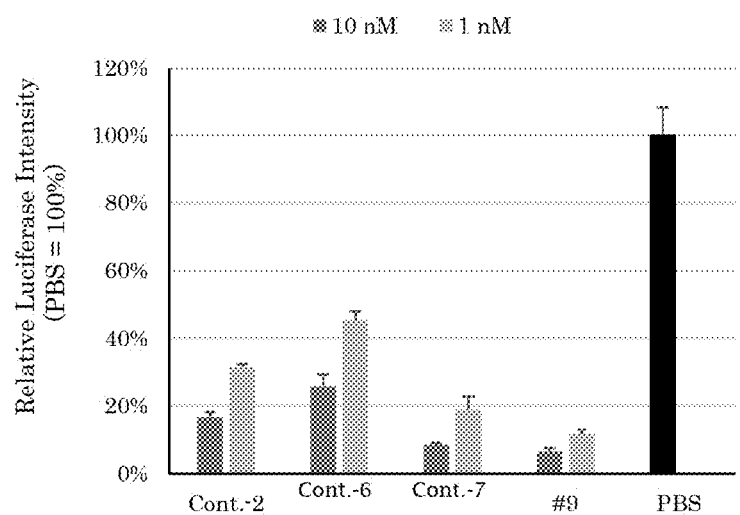
Fig. 3 Dual luciferase reporter assay using modified Luciferase siRNAs in HEK 293 cells
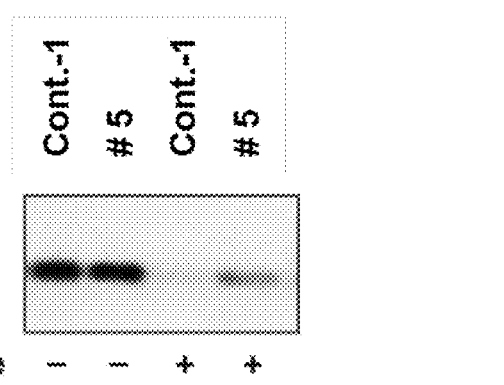
Fig. 4 3'-Exonuclease stability of modified Luciferase siRNA

SEQUENCE LISTING

```
<160> NUMBER OF SEQ ID NOS: 34

<210> SEQ ID NO 1
<211> LENGTH: 19
<212> TYPE: RNA
<213> ORGANISM: Artificial Sequence
<220> FEATURE:
<223> OTHER INFORMATION: #1 sense
<220> FEATURE:
<221> NAME/KEY: misc_feature
<222> LOCATION: (1)..(1)
<223> OTHER INFORMATION: n stands for a nucleotide unit derived from
      compound 22'

<400> SEQUENCE: 1
ncuaugggcu gaauacaaa                                                19

<210> SEQ ID NO 2
<211> LENGTH: 19
<212> TYPE: RNA
<213> ORGANISM: Artificial Sequence
<220> FEATURE:
<223> OTHER INFORMATION: #1 antisense
```

```
<400> SEQUENCE: 2
uuuguauuca gcccauagc                                                    19

<210> SEQ ID NO 3
<211> LENGTH: 19
<212> TYPE: RNA
<213> ORGANISM: Artificial Sequence
<220> FEATURE:
<223> OTHER INFORMATION: #2 sense
<220> FEATURE:
<221> NAME/KEY: misc_feature
<222> LOCATION: (19)..(19)
<223> OTHER INFORMATION: n stands for a nucleotide unit derived from
      compound 27'(b)

<400> SEQUENCE: 3
gcuaugggcu gaauacaan                                                    19

<210> SEQ ID NO 4
<211> LENGTH: 19
<212> TYPE: RNA
<213> ORGANISM: Artificial Sequence
<220> FEATURE:
<223> OTHER INFORMATION: #2 antisense

<400> SEQUENCE: 4
uuuguauuca gcccauagc                                                    19

<210> SEQ ID NO 5
<211> LENGTH: 19
<212> TYPE: RNA
<213> ORGANISM: Artificial Sequence
<220> FEATURE:
<223> OTHER INFORMATION: #3 sense
<220> FEATURE:
<221> NAME/KEY: misc_feature
<222> LOCATION: (1)..(1)
<223> OTHER INFORMATION: n stands for a nucleotide unit derived from
      compound 22'
<220> FEATURE:
<221> NAME/KEY: misc_feature
<222> LOCATION: (19)..(19)
<223> OTHER INFORMATION: n stands for a nucleotide unit derived from
      compound 27'(b)

<400> SEQUENCE: 5
ncuaugggcu gaauacaan                                                    19

<210> SEQ ID NO 6
<211> LENGTH: 19
<212> TYPE: RNA
<213> ORGANISM: Artificial Sequence
<220> FEATURE:
<223> OTHER INFORMATION: #3 antisense

<400> SEQUENCE: 6
uuuguauuca gcccauagc                                                    19

<210> SEQ ID NO 7
<211> LENGTH: 19
<212> TYPE: RNA
<213> ORGANISM: Artificial Sequence
<220> FEATURE:
<223> OTHER INFORMATION: #4 sense
<220> FEATURE:
<221> NAME/KEY: misc_feature
<222> LOCATION: (1)..(1)
<223> OTHER INFORMATION: n stands for a nucleotide unit derived from
```

```
        compound 22'
<220> FEATURE:
<221> NAME/KEY: misc_feature
<222> LOCATION: (2)..(2)
<223> OTHER INFORMATION: n stands for a nucleotide unit derived from
      compound 20'

<400> SEQUENCE: 7
nnuaugggcu gaauacaaa                                                    19

<210> SEQ ID NO 8
<211> LENGTH: 19
<212> TYPE: RNA
<213> ORGANISM: Artificial Sequence
<220> FEATURE:
<223> OTHER INFORMATION: #4 antisense

<400> SEQUENCE: 8
uuuguauuca gcccauagc                                                    19

<210> SEQ ID NO 9
<211> LENGTH: 19
<212> TYPE: RNA
<213> ORGANISM: Artificial Sequence
<220> FEATURE:
<223> OTHER INFORMATION: #5 sense
<220> FEATURE:
<221> NAME/KEY: misc_feature
<222> LOCATION: (18)..(18)
<223> OTHER INFORMATION: n stands for a nucleotide unit derived from
      comound 27'(a)
<220> FEATURE:
<221> NAME/KEY: misc_feature
<222> LOCATION: (19)..(19)
<223> OTHER INFORMATION: n stands for a nucleotide unit derived from
      compound 27'(b)

<400> SEQUENCE: 9
gcuaugggcu gaauacann                                                    19

<210> SEQ ID NO 10
<211> LENGTH: 19
<212> TYPE: RNA
<213> ORGANISM: Artificial Sequence
<220> FEATURE:
<223> OTHER INFORMATION: #5 antisense

<400> SEQUENCE: 10
uuuguauuca gcccauagc                                                    19

<210> SEQ ID NO 11
<211> LENGTH: 19
<212> TYPE: RNA
<213> ORGANISM: Artificial Sequence
<220> FEATURE:
<223> OTHER INFORMATION: #6 sense
<220> FEATURE:
<221> NAME/KEY: misc_feature
<222> LOCATION: (1)..(1)
<223> OTHER INFORMATION: n stands for a nucleotide unit derived from
      compound 20'
<220> FEATURE:
<221> NAME/KEY: misc_feature
<222> LOCATION: (19)..(19)
<223> OTHER INFORMATION: n stands for a nucleotide unit derived from
      compound 8'(b)

<400> SEQUENCE: 11
ngaucauaca aaagaucan                                                    19
```

```
<210> SEQ ID NO 12
<211> LENGTH: 19
<212> TYPE: RNA
<213> ORGANISM: Artificial Sequence
<220> FEATURE:
<223> OTHER INFORMATION: #6 antisense

<400> SEQUENCE: 12
augaucuuuu guaugaucg                                                    19

<210> SEQ ID NO 13
<211> LENGTH: 19
<212> TYPE: RNA
<213> ORGANISM: Artificial Sequence
<220> FEATURE:
<223> OTHER INFORMATION: #7 sense
<220> FEATURE:
<221> NAME/KEY: misc_feature
<222> LOCATION: (1)..(1)
<223> OTHER INFORMATION: n stands for a nucleotide unit derived from
      compound 20'
<220> FEATURE:
<221> NAME/KEY: misc_feature
<222> LOCATION: (2)..(2)
<223> OTHER INFORMATION: n stands for a nucleotide unit derived from
      compound 22'

<400> SEQUENCE: 13
nnaucauaca aaagaucau                                                    19

<210> SEQ ID NO 14
<211> LENGTH: 19
<212> TYPE: RNA
<213> ORGANISM: Artificial Sequence
<220> FEATURE:
<223> OTHER INFORMATION: #7 antisense

<400> SEQUENCE: 14
augaucuuuu guaugaucg                                                    19

<210> SEQ ID NO 15
<211> LENGTH: 19
<212> TYPE: RNA
<213> ORGANISM: Artificial Sequence
<220> FEATURE:
<223> OTHER INFORMATION: #8 sense
<220> FEATURE:
<221> NAME/KEY: misc_feature
<222> LOCATION: (1)..(1)
<223> OTHER INFORMATION: n stands for a nucleotide unit derived from
      compound 20'
<220> FEATURE:
<221> NAME/KEY: misc_feature
<222> LOCATION: (2)..(2)
<223> OTHER INFORMATION: n stands for a nucleotide unit derived from
      compound 22'
<220> FEATURE:
<221> NAME/KEY: misc_feature
<222> LOCATION: (18)..(18)
<223> OTHER INFORMATION: n stands for a nucleotide unit derived from
      compound 27'(a)
<220> FEATURE:
<221> NAME/KEY: misc_feature
<222> LOCATION: (19)..(19)
<223> OTHER INFORMATION: n stands for a nucleotide unit derived from
      compound 8'(b)

<400> SEQUENCE: 15
nnaucauaca aaagaucnn                                                    19
```

```
<210> SEQ ID NO 16
<211> LENGTH: 19
<212> TYPE: RNA
<213> ORGANISM: Artificial Sequence
<220> FEATURE:
<223> OTHER INFORMATION: #8 antisense

<400> SEQUENCE: 16
augaucuuuu guaugaucg                                                  19

<210> SEQ ID NO 17
<211> LENGTH: 21
<212> TYPE: DNA
<213> ORGANISM: Artificial Sequence
<220> FEATURE:
<223> OTHER INFORMATION: #9 sense
<220> FEATURE:
<221> NAME/KEY: misc_difference
<222> LOCATION: (1)..(19)
<223> OTHER INFORMATION: RNA
<220> FEATURE:
<221> NAME/KEY: misc_difference
<222> LOCATION: (20)..(21)
<223> OTHER INFORMATION: DNA

<400> SEQUENCE: 17
cgaucauaca aaagaucaut t                                               21

<210> SEQ ID NO 18
<211> LENGTH: 21
<212> TYPE: DNA
<213> ORGANISM: Artificial Sequence
<220> FEATURE:
<223> OTHER INFORMATION: #9 antisense
<220> FEATURE:
<221> NAME/KEY: misc_difference
<222> LOCATION: (1)..(19)
<223> OTHER INFORMATION: RNA
<220> FEATURE:
<221> NAME/KEY: misc_feature
<222> LOCATION: (7)..(7)
<223> OTHER INFORMATION: n stands for a nucleotide unit derived from
      compound 8'(a)
<220> FEATURE:
<221> NAME/KEY: misc_difference
<222> LOCATION: (20)..(21)
<223> OTHER INFORMATION: DNA

<400> SEQUENCE: 18
augaucnuuu guaugaucgt t                                               21

<210> SEQ ID NO 19
<211> LENGTH: 19
<212> TYPE: RNA
<213> ORGANISM: Artificial Sequence
<220> FEATURE:
<223> OTHER INFORMATION: #10 sense
<220> FEATURE:
<221> NAME/KEY: misc_feature
<222> LOCATION: (4)..(4)
<223> OTHER INFORMATION: n stands for 2'- fluorouridine
<220> FEATURE:
<221> NAME/KEY: misc_feature
<222> LOCATION: (5)..(5)
<223> OTHER INFORMATION: n stands for 2'- fluorocytidine
<220> FEATURE:
<221> NAME/KEY: misc_feature
<222> LOCATION: (7)..(7)
<223> OTHER INFORMATION: n stands for 2'- fluorouridine
<220> FEATURE:
<221> NAME/KEY: misc_feature
<222> LOCATION: (8)..(8)
<223> OTHER INFORMATION: n stands for 2'- fluorocytidine
```

```
<220> FEATURE:
<221> NAME/KEY: misc_feature
<222> LOCATION: (9)..(9)
<223> OTHER INFORMATION: n stands for 2'- fluorouridine
<220> FEATURE:
<221> NAME/KEY: misc_feature
<222> LOCATION: (10)..(10)
<223> OTHER INFORMATION: n stands for 2'- fluorocytidine
<220> FEATURE:
<221> NAME/KEY: misc_feature
<222> LOCATION: (14)..(14)
<223> OTHER INFORMATION: n stands for 2'- fluorouridine
<220> FEATURE:
<221> NAME/KEY: misc_feature
<222> LOCATION: (15)..(15)
<223> OTHER INFORMATION: n stands for 2'- fluorocytidine
<220> FEATURE:
<221> NAME/KEY: misc_feature
<222> LOCATION: (16)..(16)
<223> OTHER INFORMATION: n stands for 2'- fluorouridine
<220> FEATURE:
<221> NAME/KEY: misc_feature
<222> LOCATION: (17)..(17)
<223> OTHER INFORMATION: n stands for 2'- fluorouridine
<220> FEATURE:
<221> NAME/KEY: misc_feature
<222> LOCATION: (19)..(19)
<223> OTHER INFORMATION: n stands for 2'- fluorocytidine

<400> SEQUENCE: 19
ggannannnn aagnnnnan                                                 19

<210> SEQ ID NO 20
<211> LENGTH: 21
<212> TYPE: RNA
<213> ORGANISM: Artificial Sequence
<220> FEATURE:
<223> OTHER INFORMATION: #10 antisense
<220> FEATURE:
<221> NAME/KEY: misc_feature
<222> LOCATION: (2)..(2)
<223> OTHER INFORMATION: n stands for 2'- fluorouridine
<220> FEATURE:
<221> NAME/KEY: misc_feature
<222> LOCATION: (7)..(7)
<223> OTHER INFORMATION: n stands for 2'- fluorocytidine
<220> FEATURE:
<221> NAME/KEY: misc_feature
<222> LOCATION: (8)..(8)
<223> OTHER INFORMATION: n stands for 2'- fluorouridine
<220> FEATURE:
<221> NAME/KEY: misc_feature
<222> LOCATION: (9)..(9)
<223> OTHER INFORMATION: n stands for 2'- fluorouridine
<220> FEATURE:
<221> NAME/KEY: misc_feature
<222> LOCATION: (14)..(14)
<223> OTHER INFORMATION: n stands for 2'- fluorouridine
<220> FEATURE:
<221> NAME/KEY: misc_feature
<222> LOCATION: (17)..(17)
<223> OTHER INFORMATION: n stands for 2'- fluorouridine
<220> FEATURE:
<221> NAME/KEY: misc_feature
<222> LOCATION: (18)..(18)
<223> OTHER INFORMATION: n stands for 2'- fluorocytidine
<220> FEATURE:
<221> NAME/KEY: misc_feature
<222> LOCATION: (19)..(19)
<223> OTHER INFORMATION: n stands for 2'- fluorocytidine
<220> FEATURE:
<221> NAME/KEY: misc_feature
<222> LOCATION: (20)..(20)
<223> OTHER INFORMATION: n stands for a nucleotide unit derived from
      compound 18'(a)
<220> FEATURE:
<221> NAME/KEY: misc_feature
```

```
<222> LOCATION: (21)..(21)
<223> OTHER INFORMATION: n stands for a nucleotide unit derived from
      compound 18'(b)

<400> SEQUENCE: 20
gnaagannng agangannnn n                                              21

<210> SEQ ID NO 21
<211> LENGTH: 19
<212> TYPE: RNA
<213> ORGANISM: Artificial Sequence
<220> FEATURE:
<223> OTHER INFORMATION: Cont-1 sense

<400> SEQUENCE: 21
gcuaugggcu gaauacaaa                                                 19

<210> SEQ ID NO 22
<211> LENGTH: 19
<212> TYPE: RNA
<213> ORGANISM: Artificial Sequence
<220> FEATURE:
<223> OTHER INFORMATION: Cont-1 antisense

<400> SEQUENCE: 22
uuuguauuca gcccauagc                                                 19

<210> SEQ ID NO 23
<211> LENGTH: 21
<212> TYPE: DNA
<213> ORGANISM: Artificial Sequence
<220> FEATURE:
<223> OTHER INFORMATION: Cont-2 sense
<220> FEATURE:
<221> NAME/KEY: misc_difference
<222> LOCATION: (1)..(19)
<223> OTHER INFORMATION: RNA
<220> FEATURE:
<221> NAME/KEY: misc_difference
<222> LOCATION: (20)..(21)
<223> OTHER INFORMATION: DNA

<400> SEQUENCE: 23
cgaucauaca aaagaucaut t                                              21

<210> SEQ ID NO 24
<211> LENGTH: 21
<212> TYPE: DNA
<213> ORGANISM: Artificial Sequence
<220> FEATURE:
<223> OTHER INFORMATION: Cont-2 antisense
<220> FEATURE:
<221> NAME/KEY: misc_difference
<222> LOCATION: (1)..(19)
<223> OTHER INFORMATION: RNA
<220> FEATURE:
<221> NAME/KEY: misc_difference
<222> LOCATION: (20)..(21)
<223> OTHER INFORMATION: DNA

<400> SEQUENCE: 24
augaucuuuu guaugaucgt t                                              21

<210> SEQ ID NO 25
<211> LENGTH: 19
<212> TYPE: RNA
<213> ORGANISM: Artificial Sequence
<220> FEATURE:
<223> OTHER INFORMATION: Cont-3 sense
```

```
<400> SEQUENCE: 25
cgaucauaca aaagaucau                                                19

<210> SEQ ID NO 26
<211> LENGTH: 19
<212> TYPE: RNA
<213> ORGANISM: Artificial Sequence
<220> FEATURE:
<223> OTHER INFORMATION: Cont-3 antisense

<400> SEQUENCE: 26
augaucuuuu guaugaucg                                                19

<210> SEQ ID NO 27
<211> LENGTH: 21
<212> TYPE: RNA
<213> ORGANISM: Artificial Sequence
<220> FEATURE:
<223> OTHER INFORMATION: Cont-4 sense
<220> FEATURE:
<221> NAME/KEY: misc_binding
<222> LOCATION: (20)..(21)
<223> OTHER INFORMATION: phosphorothioate binding

<400> SEQUENCE: 27
gcuaugggcu gaauacaaau u                                             21

<210> SEQ ID NO 28
<211> LENGTH: 21
<212> TYPE: RNA
<213> ORGANISM: Artificial Sequence
<220> FEATURE:
<223> OTHER INFORMATION: Cont-4 antisense
<220> FEATURE:
<221> NAME/KEY: misc_binding
<222> LOCATION: (20)..(21)
<223> OTHER INFORMATION: phosphorothioate binding

<400> SEQUENCE: 28
uuuguauuca gcccauagcu u                                             21

<210> SEQ ID NO 29
<211> LENGTH: 19
<212> TYPE: RNA
<213> ORGANISM: Artificial Sequence
<220> FEATURE:
<223> OTHER INFORMATION: Cont-5 sense
<220> FEATURE:
<221> NAME/KEY: misc_feature
<222> LOCATION: (4)..(4)
<223> OTHER INFORMATION: n stands for 2'- fluorouridine
<220> FEATURE:
<221> NAME/KEY: misc_feature
<222> LOCATION: (5)..(5)
<223> OTHER INFORMATION: n stands for 2'- fluorocytidine
<220> FEATURE:
<221> NAME/KEY: misc_feature
<222> LOCATION: (7)..(7)
<223> OTHER INFORMATION: n stands for 2'- fluorouridine
<220> FEATURE:
<221> NAME/KEY: misc_feature
<222> LOCATION: (8)..(8)
<223> OTHER INFORMATION: n stands for 2'- fluorocytidine
<220> FEATURE:
<221> NAME/KEY: misc_feature
<222> LOCATION: (9)..(9)
<223> OTHER INFORMATION: n stands for 2'- fluorouridine
<220> FEATURE:
<221> NAME/KEY: misc_feature
<222> LOCATION: (10)..(10)
```

```
<223> OTHER INFORMATION: n stands for 2'- fluorocytidine
<220> FEATURE:
<221> NAME/KEY: misc_feature
<222> LOCATION: (14)..(14)
<223> OTHER INFORMATION: n stands for 2'- fluorouridine
<220> FEATURE:
<221> NAME/KEY: misc_feature
<222> LOCATION: (15)..(15)
<223> OTHER INFORMATION: n stands for 2'- fluorocytidine
<220> FEATURE:
<221> NAME/KEY: misc_feature
<222> LOCATION: (16)..(16)
<223> OTHER INFORMATION: n stands for 2'- fluorouridine
<220> FEATURE:
<221> NAME/KEY: misc_feature
<222> LOCATION: (17)..(17)
<223> OTHER INFORMATION: n stands for 2'- fluorouridine
<220> FEATURE:
<221> NAME/KEY: misc_feature
<222> LOCATION: (19)..(19)
<223> OTHER INFORMATION: n stands for 2'- fluorocytidine

<400> SEQUENCE: 29
ggannannnn aagnnnnan                                               19

<210> SEQ ID NO 30
<211> LENGTH: 21
<212> TYPE: RNA
<213> ORGANISM: Artificial Sequence
<220> FEATURE:
<223> OTHER INFORMATION: Cont-5 antisense
<220> FEATURE:
<221> NAME/KEY: misc_feature
<222> LOCATION: (2)..(2)
<223> OTHER INFORMATION: n stands for 2'- fluorouridine
<220> FEATURE:
<221> NAME/KEY: misc_feature
<222> LOCATION: (7)..(7)
<223> OTHER INFORMATION: n stands for 2'- fluorocytidine
<220> FEATURE:
<221> NAME/KEY: misc_feature
<222> LOCATION: (8)..(8)
<223> OTHER INFORMATION: n stands for 2'- fluorouridine
<220> FEATURE:
<221> NAME/KEY: misc_feature
<222> LOCATION: (9)..(9)
<223> OTHER INFORMATION: n stands for 2'- fluorouridine
<220> FEATURE:
<221> NAME/KEY: misc_feature
<222> LOCATION: (14)..(14)
<223> OTHER INFORMATION: n stands for 2'- fluorouridine
<220> FEATURE:
<221> NAME/KEY: misc_feature
<222> LOCATION: (17)..(17)
<223> OTHER INFORMATION: n stands for 2'- fluorouridine
<220> FEATURE:
<221> NAME/KEY: misc_feature
<222> LOCATION: (18)..(18)
<223> OTHER INFORMATION: n stands for 2'- fluorocytidine
<220> FEATURE:
<221> NAME/KEY: misc_feature
<222> LOCATION: (19)..(19)
<223> OTHER INFORMATION: n stands for 2'- fluorocytidine
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: um

<400> SEQUENCE: 30
gnaagannng agangannnu u                                            21
```

```
<210> SEQ ID NO 31
<211> LENGTH: 21
<212> TYPE: DNA
<213> ORGANISM: Artificial Sequence
<220> FEATURE:
<223> OTHER INFORMATION: Cont-6 sense
<220> FEATURE:
<221> NAME/KEY: misc_difference
<222> LOCATION: (1)..(19)
<223> OTHER INFORMATION: RNA
<220> FEATURE:
<221> NAME/KEY: misc_difference
<222> LOCATION: (20)..(21)
<223> OTHER INFORMATION: DNA

<400> SEQUENCE: 31
cgaucauaca aaagaucaut t                                              21

<210> SEQ ID NO 32
<211> LENGTH: 21
<212> TYPE: DNA
<213> ORGANISM: Artificial Sequence
<220> FEATURE:
<223> OTHER INFORMATION: Cont-6 antisense
<220> FEATURE:
<221> NAME/KEY: misc_difference
<222> LOCATION: (1)..(19)
<223> OTHER INFORMATION: RNA
<220> FEATURE:
<221> NAME/KEY: misc_feature
<222> LOCATION: (7)..(7)
<223> OTHER INFORMATION: n stands for a nucleotide unit derived from
      compound 43'
<220> FEATURE:
<221> NAME/KEY: misc_difference
<222> LOCATION: (20)..(21)
<223> OTHER INFORMATION: DNA

<400> SEQUENCE: 32
augaucnuuu guaugaucgt t                                              21

<210> SEQ ID NO 33
<211> LENGTH: 21
<212> TYPE: DNA
<213> ORGANISM: Artificial Sequence
<220> FEATURE:
<223> OTHER INFORMATION: Cont-7 sense
<220> FEATURE:
<221> NAME/KEY: misc_difference
<222> LOCATION: (1)..(19)
<223> OTHER INFORMATION: RNA
<220> FEATURE:
<221> NAME/KEY: misc_difference
<222> LOCATION: (20)..(21)
<223> OTHER INFORMATION: DNA

<400> SEQUENCE: 33
cgaucauaca aaagaucaut t                                              21

<210> SEQ ID NO 34
<211> LENGTH: 21
<212> TYPE: DNA
<213> ORGANISM: Artificial Sequence
<220> FEATURE:
<223> OTHER INFORMATION: Cont-7 antisense
<220> FEATURE:
<221> NAME/KEY: misc_difference
<222> LOCATION: (1)..(19)
<223> OTHER INFORMATION: RNA
<220> FEATURE:
<221> NAME/KEY: misc_feature
<222> LOCATION: (7)..(7)
<223> OTHER INFORMATION: n stands for a nucleotide unit derived from
```

```
           compound 44'
<220> FEATURE:
<221> NAME/KEY: misc_difference
<222> LOCATION: (20)..(21)
<223> OTHER INFORMATION: DNA

<400> SEQUENCE: 34
augaucnuuu guaugaucgt t                                                 21
```

MODIFIED NUCLEIC ACID MONOMER COMPOUND AND OLIGONUCLEIC ACID ANALOG

TECHNICAL FIELD

The present invention relates to a modified nucleic acid monomer compound and an oligonucleic acid analogue containing the monomer compound. More specifically, the present invention relates to a modified nucleic acid monomer compound having a specific backbone such as a 2-ethylglycerol or methoxymethyl-1,3-propanediol backbone instead of a ribose or deoxyribose backbone of a nucleoside, and an oligonucleic acid analogue containing the monomer compound as at least one of building blocks.

BACKGROUND ART

Numbering of atoms in a nucleic acid monomer sugar moiety as used herein follows the conventional numbering of atoms based on natural ribonucleosides (such as adenosine, cytidine, guanosine and uridine) (see chemical structural formula indicated below).

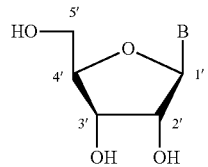

Nucleic acid medicines contain nucleic acids (oligonucleotides) such as DNA and RNA, and are expected to be applied to therapies of diseases which have been difficult to be treated by recognizing specific base sequences and specific proteins to suppress gene expression and inhibit functions of proteins.

Specific oligonucleic acids include antisense and nucleic acid aptamer. Recently, development of therapies utilizing RNA interference (RNAi) has been attracting attention.

RNA interference is a gene silencing phenomenon by double-stranded RNAs. When a double-stranded RNA having the same base sequence as a target gene is introduced into a cell, an enzyme called Dicer existing in the cytoplasm produces a double-stranded RNA having approximately 20 to 25 base pairs therefrom. The double-stranded RNA forms a protein-RNA complex called RNA-induced silencing complex (RISC) with multiple intracellular proteins, binds to a homologous sequence of messenger RNA (mRNA) synthesized from the target gene and specifically cleaves the mRNA, thereby suppressing translation reaction to a protein (NPL 1). It was reported later that RNAi could be induced with a short double-stranded RNA (small interfering RNA: siRNA) with 21 bases, and thus RNAi is attracting attention as a technique for effectively silencing only the target gene.

Meanwhile, in antisense or RNAi technology, natural-type oligonucleic acids are easily hydrolyzed by various nucleases in vivo, and thus biological stability is an issue. In order to solve the problem, nuclease resistance is sought to be improved by chemical modification such as introduction of 2'-OMe- or 2'-F-modified nucleic acid monomers and conversion of the phosphate binding sites to phosphorothioate bonds.

It is also reported that when, as a nucleic acid having a modified ribose moiety of RNA, a UNA (unlocked nucleic acid: 2',3'-seco-RNA) monomer represented by the following formula:

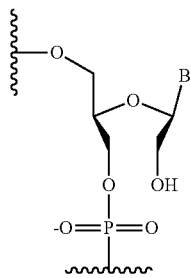

wherein B represents a nucleobase;

is introduced in a siRNA, the siRNA may have increased exonuclease resistance, the off-targeting effect may be suppressed and specificity of the target gene silencing effect may be improved (NPL 2). Further, it is suggested in PTL 1 that UNA monomers represented by the following formulae:

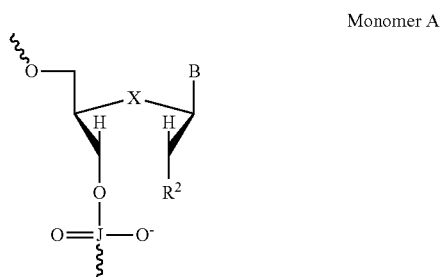

Monomer A

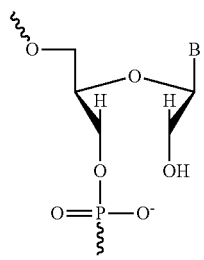

Monomer B

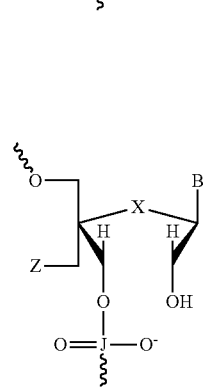

Monomer I

-continued

Monomer J

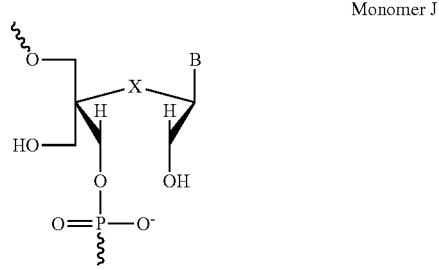

wherein X represents —O—, —S— or —CH$_2$—; J represents —P— or —S—; Z represents H, OH, CH$_2$OH, CH$_3$ or a C$_{2-22}$ alkyl chain; and R$^2$ represents H, OH, O-alkyl or the like;

are introduced into siRNA.

It is reported in NPL 3 that an oligomer containing a modified nucleoside (serinol nucleic acid: SNA) having a ribose moiety converted to a 2-amino-1',3'-propanediol (serinol) backbone represented by the following formula:

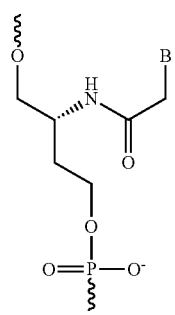

can provide a stable double-stranded structure.

CITATION LIST

Patent Literature

[PTL 1] WO 2011/139710

Non Patent Literature

[NPL 1] Fire et al., Nature, 391, 806-811 (1998)
[NPL 2] Pasternak et al., Org. Biomol. Chem., 9, 3591-3597, 2011
[NPL 3] KASHIDA Hiromu, et al., Angew. Chem. Int. Ed. 2011, 50, 1285-1288

SUMMARY OF INVENTION

Technical Problem

Although numerous modified nucleic acids have been suggested, no modified nucleic acid has yet been found that has sufficiently improved biological stability (such as stability in blood) and enhanced target gene silencing activity.

Thus, an object of the present invention is to provide a novel modified nucleic acid monomer compound that is useful upon application to medicines and allows at least one of excellent biological stability and target gene silencing activity, and an oligonucleic acid analogue containing the monomer compound as a building block.

Solution to Problem

In order to solve the problem, the inventors of the present invention conducted exhaustive study. As a result, the inventors found that when an oligonucleic acid analogue containing, as at least one of building blocks, a modified nucleic acid monomer compound that is a modified nucleoside having a specific backbone such as a 2-ethylglycerol or methoxymethyl-1,3-propanediol backbone instead of a ribose or deoxyribose backbone of a nucleoside is used as, for example, a siRNA, the obtained siRNA allows at least one of maintained or enhanced target gene silencing activity and improved biological stability, thereby completing the present invention.

The present invention, for example, relates to the following:

[1]. a compound represented by the following formula (I):

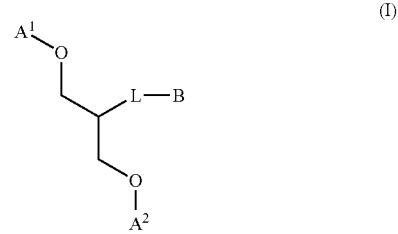

wherein A$^1$ represents a protective group of a hydroxy group;

A$^2$ represents a phosphorus functional group, a protective group of a hydroxy group or —C(=O)CH$_2$CH$_2$COOH;

B represents a nucleobase; and

L represents —OCH$_2$CH$_2$— or —CH$_2$OCH$_2$—;

or a salt thereof;

[2]. the compound according to [1] or a salt thereof, wherein B is a nucleobase selected from the following formulae (II), (III), (IV) and (V):

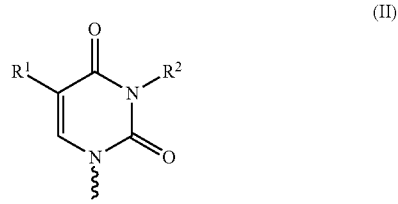

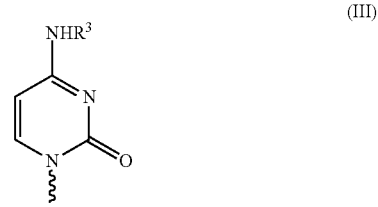

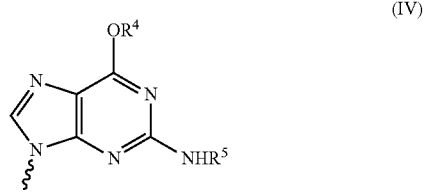

-continued

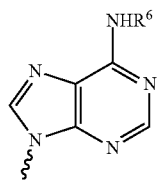
(V)

wherein $R^1$ represents a hydrogen atom or methyl;

$R^2$ and $R^4$ each independently represent a hydrogen atom, $C_{1-6}$ alkyl, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl, $C_{6-14}$ arylsulphonyl or a protective group; and $R^3$, $R^5$ and $R^6$ each independently represent $C_{1-6}$ alkyl, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl, $C_{6-14}$ arylsulphonyl or a protective group;

[3]. the compound according to [1] or [2] or a salt thereof, wherein L is —OCH$_2$CH$_2$—;

[4]. the compound according to any one of [1] to [3] or a salt thereof, wherein $A^1$ is a protective group of a hydroxy group selected from trityl, 4-methoxytrityl, 4,4'-dimethoxytrityl (DMTr) and 4,4',4"-trimethoxytrityl;

[5]. the compound according to any one of [1] to [4] or a salt thereof, wherein $A^2$ is a phosphorus functional group;

[6]. the compound according to any one of [1] to [5] or a salt thereof, wherein $A^2$ is —P(—OR$^7$)—NRR$^9$, wherein $R^7$ represents $C_{1-6}$ alkyl or 2-cyanoethyl; and $R^8$ and $R^9$ are each independently $C_{1-6}$ alkyl, or —NR$^8$R$^9$ is integrated to form

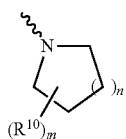

wherein $R^{10}$ represents $C_{1-3}$ alkyl; m represents an integer of 0 to 4; and n represents an integer of 1 to 3;

[7]. the compound according to any one of [1] to [4] or a salt thereof, wherein $A^2$ is —C(=O)CH$_2$CH$_2$COOH;

[8]. the compound according to any one of [2] to [7] or a salt thereof, wherein the protective groups in $R^2$, $R^3$, $R^5$ and $R^6$ are each independently selected from a carbamate protective group, an acyl protective group, an imide protective group and a benzyl protective group, and the protective group in $R^4$ is selected from a silyl protective group, a trityl protective group, a heterocyclic protective group, a benzyl protective group, an aliphatic acyl protective group, an aromatic acyl protective group, an ether protective group, a carbamoyl protective group and an alkoxycarbonyl protective group;

[9]. the compound according to [2] or a salt thereof, wherein the compound is represented by the following formula (VI):

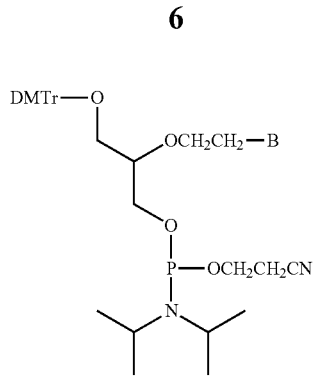
(VI)

wherein B is a nucleobase selected from above formulae (II), (III), (IV) and (V);

[10]. the compound according to [2] or a salt thereof, wherein the compound is represented by the following formula (VII):

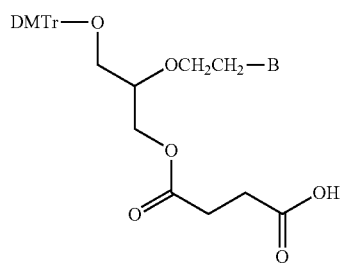
(VII)

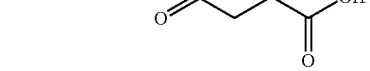

wherein B is a nucleobase selected from above formulae (II), (III), (IV) and (V);

[11]. a modified nucleic acid monomer-carrying substance, containing a monovalent group derived from a modified nucleic acid monomer compound represented by the following (VIII) supported on a solid carrier through an amino group on the carrier,

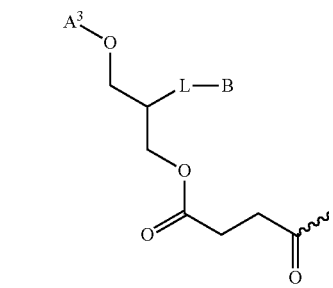
(VIII)

wherein:

$A^3$ is a hydrogen atom or a protective group of a hydroxy group selected from trityl, 4-methoxytrityl, 4,4'-dimethoxytrityl (DMTr) and 4,4',4"-trimethoxytrityl;

B represents a nucleobase; and

L represents —OCH$_2$CH$_2$— or —CH$_2$OCH$_2$— a modified nucleic acid monomer-carrying substance represented by the foregoing;

[12]. the modified nucleic acid monomer-carrying substance according to [11], wherein B is a nucleobase selected from the following formulae (II), (III), (IV) and (V):

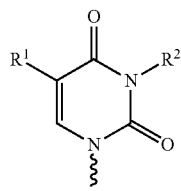
(II)

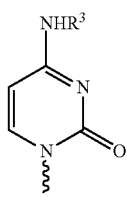
(III)

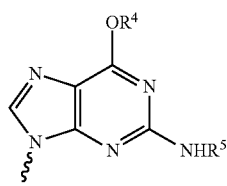
(IV)

(V)

wherein:

$R^1$ represents a hydrogen atom or methyl;

$R^2$ and $R^4$ each independently represent a hydrogen atom, $C_{1-6}$ alkyl, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl, $C_{6-14}$ arylsulphonyl or a protective group; and $R^3$, $R^5$ and $R^6$ each independently represent $C_{1-6}$ alkyl, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl, $C_{6-14}$ arylsulphonyl or a protective group;

[13]. the modified nucleic acid monomer-carrying substance according to [12], wherein the protective groups in $R^2$, $R^3$, $R^5$ and $R^6$ are each independently selected from a carbamate protective group, an acyl protective group, an imide protective group and a benzyl protective group, and the protective group of the hydroxy group in $R^4$ is selected from a silyl protective group, a trityl protective group, a heterocyclic protective group, a benzyl protective group, an aliphatic acyl protective group, an aromatic acyl protective group, an ether protective group, a carbamoyl protective group and an alkoxycarbonyl protective group;

[14]. an oligonucleic acid analogue containing one or more partial structures represented by the following formula (IX) or a salt thereof, (IX)

wherein:

B represents a nucleobase; and

L represents —OCH$_2$CH$_2$— or —CH$_2$OCH$_2$—; provided that when two or more partial structures are included, $B^3$ and L in the partial structures may be respectively the same or different;

[15]. the oligonucleic acid analogue according to [14] or a salt thereof, wherein $B^3$ is a nucleobase selected from the following formulae (II)', (III)', (IV)' and (V)':

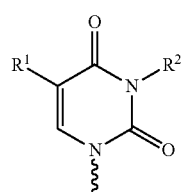
(II)'

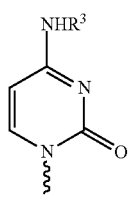
(III)'

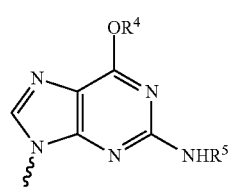
(IV)'

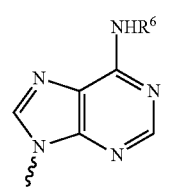
(V)' wherein:

$R^1$ represents a hydrogen atom or methyl;

$R^2$ and $R^4$ each independently represent a hydrogen atom, $C_{1-6}$ alkyl, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl, $C_{6-14}$ arylsulphonyl or a protective group; and $R^3$, $R^5$ and $R^6$ each independently represent a hydrogen atom, $C_{1-6}$ alkyl, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl, $C_{6-14}$ arylsulphonyl or a protective group;

[16]. the oligonucleic acid analogue according to [15] or a salt thereof, wherein the protective groups in $R^2$, $R^3$, $R^5$ and R[6] are each independently selected from a carbamate protective group, an acyl protective group, an imide protective group and a benzyl protective group, and the protective group of the hydroxy group in R[4] is selected from a silyl protective group, a trityl protective group, a heterocyclic protective group, a benzyl protective group, an aliphatic acyl protective group, an aromatic acyl protective group, an ether protective group, a carbamoyl protective group and an alkoxycarbonyl protective group;

[17]. the oligonucleic acid analogue according to [16] or a salt thereof, wherein B[3] is selected from the following formulae (X), (XI), (XII) and (XIII) and is a substituent selected from:

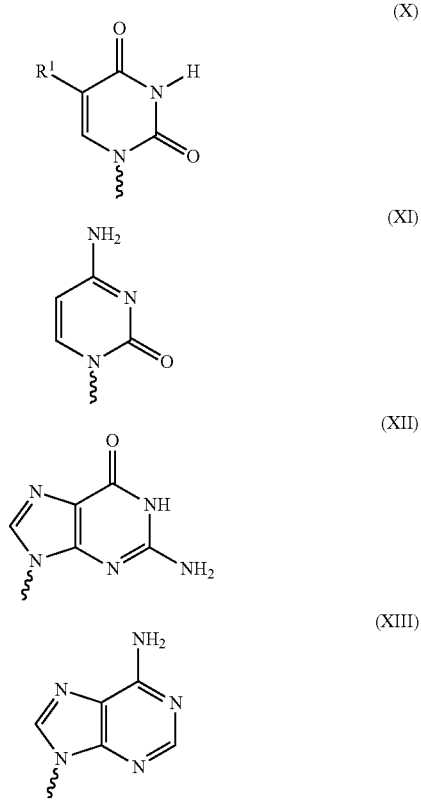

wherein R[1] is as defined above;

[18]. the oligonucleic acid analogue according to any one of [15] to [17] or a salt thereof, wherein L is —OCH$_2$CH$_2$—;

[19]. the oligonucleic acid analogue according to any one of [15] to [18] or a salt thereof, wherein the oligonucleic acid analogue contains 4 to 100 nucleobase units in total per strand; and

[20]. the oligonucleic acid analogue according to any one of [15] to [18] or a salt thereof, wherein the oligonucleic acid analogue contains 4 to 30 nucleobase units in total per strand.

Advantageous Effects of Invention

The present invention can provide an oligonucleic acid analogue having excellent biological stability (such as stability in blood) and/or target gene silencing activity.

BRIEF DESCRIPTION OF DRAWINGS

FIG. 1 is a view illustrating the result of the Luciferase activity inhibitory test using modified Luciferase siRNAs.

FIG. 2 is a view illustrating the result of the Luciferase activity inhibitory test using modified Luciferase siRNAs.

FIG. 3 is a view illustrating the result of the Luciferase activity inhibitory test using modified Luciferase siRNAs.

FIG. 4 is a view illustrating the result of the nuclease stability test using a Luciferase modified siRNA of an embodiment.

DESCRIPTION OF EMBODIMENTS

The definitions of the terms used in the present specification are hereinafter described and the present invention is specifically described.

As used herein, the halogen atom refers to, for example, a fluorine atom, a chlorine atom, a bromine atom and an iodine atom.

The $C_{1-6}$ alkyl group refers to, for example, methyl, ethyl, n-propyl, isopropyl, n-butyl, isobutyl, t-butyl, n-pentyl, isopentyl, neopentyl, n-hexyl, 1-methylpropyl, 1,2-dimethylpropyl, 1-ethylpropyl, 1-methyl-2-ethylpropyl, 1-ethyl-2-methylpropyl, 1,1,2-trimethylpropyl, 1-methylbutyl, 2-methylbutyl, 1,1-dimethylbutyl, 2,2-dimethylbutyl, 2-ethylbutyl, 1,3-dimethylbutyl, 2-methylpentyl or 3-methylpentyl. In one embodiment, the $C_{1-6}$ alkyl group is methyl, ethyl, n-propyl or isopropyl.

The $C_{2-6}$ alkenyl group refers to, for example, vinyl, allyl, 1-propenyl, isopropenyl, 1-buten-1-yl, 1-buten-2-yl, 1-buten-3-yl, 2-buten-1-yl or 2-buten-2-yl. The $C_{3-6}$ alkenyl group is a $C_{2-6}$ alkenyl group from which vinyl is eliminated.

The $C_{2-6}$ alkynyl group refers to, for example, ethynyl, 1-propynyl, 2-propynyl, butynyl, pentynyl or hexynyl. The $C_{3-6}$ alkynyl group is a $C_{2-6}$ alkynyl group from which ethynyl is eliminated.

The $C_{1-6}$ alkoxy group refers to, for example, methoxy, ethoxy, n-propoxy, isopropoxy, n-butoxy, isobutoxy, sec-butoxy, t-butoxy, n-pentoxy, isopentoxy, sec-pentoxy, t-pentoxy, n-hexoxy, isohexoxy, 1,2-dimethylpropoxy, 2-ethylpropoxy, 1-methyl-2-ethylpropoxy, 1-ethyl-2-methylpropoxy, 1,1,2-trimethylpropoxy, 1-dimethylbutoxy, 2,2-dimethylbutoxy, 2-ethylbutoxy, 1,3-dimethylbutoxy, 2-methylpentoxy, 3-methylpentoxy or hexyloxy. In one embodiment, the $C_{1-6}$ alkoxy group is methoxy.

The $C_{1-6}$ alkylthio group refers to, for example, methylthio, ethylthio, n-propylthio, isopropylthio, n-butylthio, isobutylthio, t-butylthio, n-pentylthio, isopentylthio, neopentylthio, n-hexylthio or 1-methylpropylthio.

The $C_{1-6}$ alkylsulphonyl group refers to, for example, methylsulphonyl, ethylsulphonyl, n-propylsulphonyl, isopropylsulphonyl, n-butylsulphonyl, isobutylsulphonyl, t-butylsulphonyl, n-pentylsulphonyl, isopentylsulphonyl, neopentylsulphonyl, n-hexylsulphonyl or 1-methylpropylsulphonyl.

The $C_{1-6}$ alkyl-carbonyl group refers to, for example, acetyl, propionyl or butyryl.

The $C_{6-14}$ aryloxy-carbonyl group refers to, for example, phenyloxycarbonyl or naphthyloxycarbonyl.

The $C_{6-14}$ aryl-carbonyl group refers to, for example, benzoyl or naphthoyl. In one embodiment, the $C_{6-14}$ aryl-carbonyl group is benzoyl.

The $C_{6-14}$ arylsulphonyl group refers to, for example, benzenesulphonyl or naphthylsulphonyl.

The mono-$C_{1-6}$ alkylamino group refers to, for example, monomethylamino, monoethylamino, mono-n-propylamino, mono-isopropylamino, mono-n-butylamino, mono-isobutylamino, mono-t-butylamino, mono-n-pentylamino, mono-isopentylamino or mono-neopentylamino.

The di-$C_{1-6}$ alkylamino group refers to, for example, dimethylamino, diethylamino, di-n-propylamino, di-isopropylamino, di-n-butylamino, di-isobutylamino, di-t-butylamino, di-n-pentylamino, di-isopentylamino or di-neopentylamino.

The "nucleobase" is not particularly limited as far as it is used for synthesis of nucleic acid, and is defined to encompass (i) nucleobases of natural-type nucleosides (cytosyl group, uracil group, thiminyl group, adenyl group and guanyl group), (ii) modified nucleobases or base analogues (such as those having a base moiety substituted by a halogen atom, a $C_{1-6}$ alkyl group, a $C_{1-6}$ alkoxy group, a $C_{2-6}$ alkenyl group, a $C_{2-6}$ alkynyl group, a $C_{1-6}$ alkyl-carbonyl group, a $C_{1-6}$ alkylthio group, a $C_{1-6}$ alkylsulphonyl group, a $C_{6-14}$ aryloxy-carbonyl group, a $C_{6-14}$ aryl-carbonyl group, a $C_{6-14}$ arylsulphonyl group, an amino group, a mono-$C_{1-6}$ alkylamino group, a di-$C_{1-6}$ alkylamino group, a nitro group, a hydroxy group, a cyano group, a carboxy group and the like) and (iii) nucleobases which may be protected (nucleobases in above (i) and (ii) in which an amino group or a hydroxy group is protected with a protective group). The base analogue is a chemical substance having a structure that is similar to a base of a natural-type nucleoside.

The "nucleoside" as used herein refers to a compound formed with a nucleobase covalently bound to a pentose sugar (ribose, deoxyribose or a modification thereof).

The "nucleotide" means a phosphate ester of a nucleoside as a monomer unit or in a nucleic acid.

The "nucleotide analogue" refers to a compound in which a pentose sugar and/or a nucleotide base and/or one or more phosphate esters in a nucleoside is arbitrarily substituted by an analogue thereof.

The "oligonucleic acid" or "oligonucleotide" generally refers to a nucleic acid molecule having a small number of nucleobases in a molecule or an analogue thereof. Meanwhile, a nucleic acid molecule having a large number of nucleobases or an analogue thereof is referred to as a polynucleic acid or polynucleotide. However, the boundary of the number of polymerization between polynucleic acid or polynucleotide and oligonucleic acid or oligonucleotide is not clearly defined. In the present specification, the oligonucleic acid or oligonucleotide refers to a nucleic acid molecule or an analogue thereof having 4 to 100 (particularly, 4 to 50) nucleobases in a molecule. The oligonucleic acid or oligonucleotide is a linear oligomer of monomer units (nucleotide subunits) which are nucleotides or nucleotide analogues.

The "analogue" in relation to oligonucleic acid or oligonucleotide may have, for example, at least one modified moiety selected from a modified or substituted sugar moiety, a modified or substituted base moiety and a modified or substituted sugar linkage moiety, or a combination thereof.

In the present specification, a chemical structural formula of a compound may represent an isomer. However, the compound of the present invention is not limited to the illustration by the chemical structural formula unless it is specified that the compound is limited to an isomer by, for example, representation by the name of the compound or unless a separation step of an isomer is specified, and the compound of the present invention encompasses isomers such as all geometric isomers that may be possible from the structure of the compound, optical isomers based on asymmetric carbons, stereoisomer and tautomers, and mixtures of the isomers. Therefore, when a compound may have an asymmetric carbon atom in a molecule and thus may have an optically-active substance and a racemic substance, the compound encompasses both the optically-active substance and the racemic substance unless particularly stated that the compound is limited to one of the isomers.

The present invention in one embodiment provides a modified nucleic acid monomer compound having a specific backbone such as a 2-ethylglycerol or methoxymethyl-1,3-propanediol backbone instead of a ribose or deoxyribose backbone of a nucleoside.

The modified nucleic acid monomer compound of the present invention and the oligonucleic acid analogue containing the same as at least one of building blocks thereof are hereinafter specifically described.

1. Modified Nucleic Acid Monomer Compound

The modified nucleic acid monomer compound of the present invention is represented by the following formula (I):

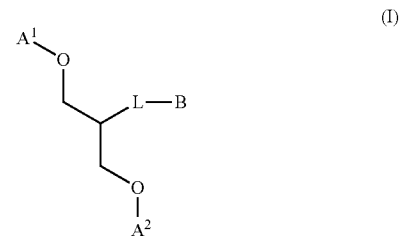

In the modified nucleic acid monomer compound of formula (I), the moieties —O-$A^1$ and —O-$A^2$ are involved in binding to nucleotides that form an oligonucleic acid analogue instead of the 5' position and the 3' position, respectively, of a ribose or a deoxyribose, and thus can be used for production of an oligonucleic acid derivative.

In formula (I), the numbers of carbon atoms in the propane backbone according to the IUPAC nomenclature may be different depending on the types of $A^1$ and $A^2$. However, for the convenience of description of the present invention, the numbers as indicated in the following formula are used:

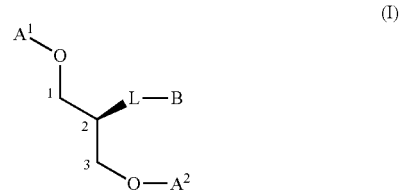

In formula (I), B is a nucleobase.

B in one embodiment is a nucleobase selected from the following formulae (II), (III), (IV) and (V):

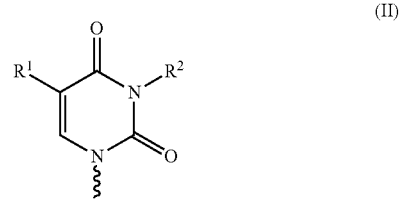

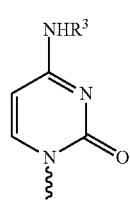

(III)

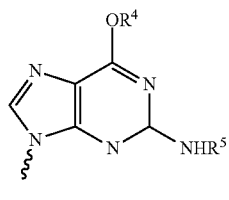

(IV)

(V)

In formulae (II) to (V), $R^1$ represents a hydrogen atom or methyl.

$R^2$ and $R^4$ each independently represent a hydrogen atom, $C_{1-6}$ alkyl, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl, $C_{6-14}$ arylsulphonyl or a protective group; and $R^3$, $R^5$ and $R^6$ each independently represent $C_{1-6}$ alkyl, $C_{3-6}$ alkenyl, $C_{3-6}$ alkynyl, $C_{1-6}$ alkyl-carbonyl, $C_{1-6}$ alkylthio, $C_{1-6}$ alkylsulphonyl, $C_{6-14}$ aryloxy-carbonyl, $C_{6-14}$ arylcarbonyl, $C_{6-14}$ arylsulphonyl or a protective group.

$R^2$, $R^3$, $R^4$, $R^5$ and $R^6$ may be the same or different each other.

The protective group serves as a protective group of an amino group or a protective group of a hydroxy group during production of a nucleotide oligomer (oligonucleic acid analogue) described hereinbelow. Namely, $R^2$, $R^3$, $R^5$ and $R^6$ are protective groups of amino groups and $R^4$ is a protective group of a hydroxy group. The protective group is not particularly limited as long as the protective group is stable during production of a nucleotide oligomer and can be deprotected after formation of the oligomer. Examples thereof include those listed hereinbelow.

Examples of the protective group of an amino group include carbamate protective groups such as t-butoxycarbonyl, benzyloxycarbonyl, 9-fluorenylmethyloxycarbonyl, 2,2,2-trichloroethoxycarbonyl and allyloxycarbonyl; acyl protective groups such as acetyl, chloroacetyl, fluoroacetyl, trifluoroacetyl, butyryl, isobutyryl, benzoyl and 2-nitrobenzoyl; imide protective groups such as phthaloyl; benzyl protective groups such as benzyl, 4-methoxybenzyl and 3,4-dimethoxybenzyl.

Examples of the protective group of a hydroxy group include similar protective groups to the protective groups of a hydroxy group in $A^1$ described hereinbelow other than sulphonyl protective groups.

Because of the stability during condensation reaction used in nucleic acid synthesis and ease of deprotection, $R^2$ and $R^6$ in B in one embodiment are respectively an acyl protective group such as acetyl, isobutyryl and benzoyl. For the same reason, $R^3$ and $R^5$ in one embodiment are an acyl protective group such as acetyl, isobutyryl and 2-methylpropanoyl. For the same reason, $R^4$ in one embodiment is a carbamoyl protective group such as dimethylcarbamoyl and diphenylcarbamoyl.

In formula (I), $A^1$ represents a protective group of a hydroxy group. —O-$A^1$ is involved in binding to a nucleotide instead of the 5' position of a ribose or a deoxyribose, and may form a nucleotide oligomer (oligonucleic acid analogue).

The protective group of a hydroxy group is not particularly limited and may be, for example, any protective group that is commonly used as a protective group of a hydroxy group in nucleic acid. Examples of the protective group include silyl protective groups such as trimethylsilyl (TMS), triisopropylsilyl, t-butyldimethylsilyl (TBS), (triphenylmethyl)dimethylsilyl, t-butyldiphenylsilyl (TBDPS), tribenzylsilyl and triphenylsilyl; trityl protective groups such as trityl, 4-monomethoxytrityl (MMTr), 4,4'-dimethoxytrityl (DMTr) and 4,4',4''-trimethoxytrityl; heterocyclic protective groups such as tetrahydropyranyl, 3-bromotetrahydropyranyl, tetrahydrothiopyranyl, 4-methoxytetrahydropyranyl, 4-methoxytetrahydrothiopyranyl, tetrahydrofuranyl and tetrahydrothiofuranyl; benzyl protective groups such as benzyl, 4-methoxybenzyl, 2-nitrobenzyl, 4-nitrobenzyl and 4-cyanobenzyl; aliphatic acyl protective groups such as acetyl, chloroacetyl, trichloroacetyl, trifluoroacetyl, butyryl, propionyl, pivaloyl, levulinyl, pentanoyl and valeryl; aromatic acyl protective groups such as benzoyl, 2,6-dichlorobenzoyl, 2-toluoyl, 4-methoxybenzoyl and 2,4,6-trimethylbenzoyl; ether protective groups such as t-butoxymethyl, methoxymethyl, 1-ethoxyethyl, 1-(2-chloroethoxy)ethyl, 2-trimethylsilylethoxyethyl (SEM), 2-(cyanoethoxy)ethyl (CEE), 2-naphthylmethoxymethyl (NAPOM) and diphenylmethyl; carbamoyl protective groups such as dimethylcarbamoyl and diphenylcarbamoyl; sulphonyl protective groups such as mesyl, tosyl and trifluoromethanesulphonyl; and alkoxycarbonyl protective groups such as 9-fluorenylmethoxycarbonyl.

For the protective groups of hydroxy groups, references such as Beaucage et al., Tetrahedron, Vol. 48, pp. 2223-2311, 1992; and Greene and Wuts, Protecting Groups in Organic Synthesis, Chapter, 3rd Ed., John Wiley & Sons, New York, 1999 (hereinafter also referred to as the "reference by Greene et al.") may be referred to.

$A^1$ in formula (I) is, because of the stability during condensation reaction used in nucleic acid synthesis and ease of deprotection, more preferably a trityl protective group such as 4,4'-dimethoxytrityl (DMTr) and 4-monomethoxytrityl (MMTr) or a silyl protective group, and still more preferably 4,4'-dimethoxytrityl (DMTr).

In formula (I), $A^2$ represents a phosphorus functional group, a protective group of a hydroxy group or —C(=O)CH$_2$CH$_2$COOH. —O-$A^2$ is involved in binding to a nucleotide instead of the 3' position of a ribose or a deoxyribose, and may form a nucleotide oligomer (oligonucleic acid analogue).

Examples of the protective group of a hydroxy group may include the protective groups of hydroxy groups in $A^1$ described above. The protective group is preferably deprotected under a different condition from that for the protective group of a hydroxy group in $A^1$. For example, when the protective group of a hydroxy group in $A^1$ is a trityl protective group, the protective group is preferably a silyl protective group and, among others, more preferably triisopropylsilyl, t-butyldimethylsilyl (TBS) and t-butyldiphenylsilyl (TBDPS) and still more preferably t-butyldiphenylsilyl (TBDPS) because of ease of deprotection and selectivity. When the protective group of a hydroxy group in $A^1$ is a silyl protective group, the protective group $A^2$ of a hydroxy group is preferably a heterocyclic protective group, an aliphatic acyl protective group or an aromatic acyl protective group.

Examples of the phosphorus functional group include phosphorus functional groups which are phosphoric acid reactive groups upon production of the oligonucleic acid analogue of formula (VII) using the modified nucleic acid monomer compound of formula (I) by the phosphoramidite method (S. L. Beaucage, M. H. Caruthers, Tetrahedron Lett., 22, 1859 (1981)), the triester method (R. L. Letsinger, K. K. Ogilvie, J. Am. Chem. Soc., 89, 4801 (1967)), the H-phosphonate method (P. J. Garegg, I. Lindh, T. Regberg, J. Stawinski, R. Stronberg, C. Henrichson, Tetrahedron Lett., 27, 4051 (1986)) and the like which are known nucleic acid synthesis methods.

Examples of the phosphorus functional group which is a phosphoric acid reactive group upon production by the phosphoramidite method include the phosphorus functional group represented by the following formula (i):

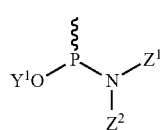

(i)

wherein $Y^1$ represents a protective group of a phosphoric acid; $Z^1$ and $Z^2$ each independently represent a $C_{1-6}$ alkyl or $Z^1$ and $Z^2$ form, together with a nitrogen atom to which $Z^1$ and $Z^2$ bind, a 5- to 7-membered nitrogen-containing heterocyclic ring which may further contain 1 to 3 heteroatoms.

Examples of the protective group of phosphoric acid in $Y^1$ include protective groups that can be eliminated by β-elimination such as 2-cyanoethyl, 2-(phenylsulphonyl)ethyl, 2,2,2-trichloroethyl (TCE) and 2,2,2-tribromoethyl; protective groups that can be eliminated with a fluoride ion such as 2-trimethylsilylethyl (TMSE) and 2-(diphenylmethylsilyl) ethyl (DPSE); protective groups that can be eliminated by cyclisation reaction such as 4-[N-methyl-N-(trifluoroacetyl) amino]butyl (TFAB), 2-[(1-naphthyl)carbamoyloxy]ethyl (NCE) and 4-oxopentyl; protective groups that can be eliminated by nucleophilic substitution reaction on a carbon atom such as alkyl (such as $C_{1-6}$ alkyl) such as methyl, and 2,4-dinitrobenzyl; protective groups that can be eliminated by hydrogenolysis such as benzyl; and protective groups that can be eliminated by substitution reaction using a palladium catalyst such as allyl. Among others, $C_{1-6}$ alkyl such as methyl, 2-cyanoethyl, 2-trimethylsilylethyl and the like are commonly used in the phosphoramidite method. $Y^1$ in one embodiment is 2-cyanoethyl because of excellent elimination conditions. Alternatively, $Y^1$ in another embodiment is methyl because of elimination ability.

Examples of $—NZ^1Z^2$ in formula (i) may include dimethylamino, diethylamino, di-n-propylamino, di-isopropylamino ($—N(i-Pr)_2$), di-n-butylamino, di-isobutylamino, di-t-butylamino, di-n-pentylamino, di-isopentylamino and di-neopentylamino. Examples of the 5- to 7-membered nitrogen-containing heterocyclic ring which may further contain a heteroatom and which is formed from $Z^1$ and $Z^2$ together with a nitrogen atom to which $Z^1$ and $Z^2$ bind include morpholin-1-yl, piperidin-1-yl and the like. Examples of the heteroatom include nitrogen atom, oxygen atom, sulphur atom and the like. Among others, diisopropylamino, dimethylamino and the like are commonly used in the phosphoramidite method. $—NZ^1Z^2$ in one embodiment is diisopropylamino. $—NZ^1Z^2$ in another embodiment is dimethylamino.

Examples of the phosphorus functional group which is a phosphoric acid reactive group upon production by the triester method include the phosphorus functional group represented by the following formula (ii):

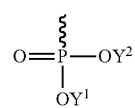

(ii)

wherein $Y^1$ represents a protective group of phosphoric acid; and $Y^2$ represents a hydrogen atom or a protective group of phosphoric acid.

Examples of the protective group of phosphoric acid in $Y^1$ and $Y^2$ in formula (ii) may include the protective groups of phosphoric acid described above for $Y^1$ in formula (i).

Examples of the phosphorus functional group which is a phosphoric acid reactive group upon production by the H-phosphonate method include the phosphorus functional group represented by the following formula (iii):

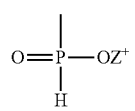

(iii)

wherein $Z^+$ represents a cation.

Examples of the cation of Z in formula (iii) include mono-$C_{1-6}$ alkylammonium ions such as methylammonium ion, ethylammonium ion and isobutylammonium ion; di-$C_{1-6}$ alkylammonium ions such as dimethylammonium ion, diethylammonium ion and diisobutylammonium ion; and metal ions such as potassium ion and lithium ion.

$A^2$ in formula (I) in one embodiment is $—C(=O)CH_2CH_2COOH$.

$A^2$ in another embodiment is $—P(—OR^7)—NRR^9$.

$R^7$ represents $C_{1-6}$ alkyl or 2-cyanoethyl. Preferably, $R^7$ is, because of selective elimination conditions, methyl or 2-cyanoethyl and more preferably 2-cyanoethyl.

$R^8$ and $R^9$ each independently are $C_{1-6}$ alkyl, or $—NR^8R^9$ is integrated to form

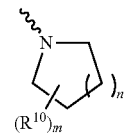

wherein $R^{10}$ represents $C_{1-3}$ alkyl; m represents an integer of 0 to 4; and n represents an integer of 1 to 3.

For example, $R^8$ and $R^9$ independently are $C_{1-3}$ alkyl, or $—NR^8R^9$ is integrated to form a group selected from morpholin-1-yl and piperidin-1-yl.

$A^2$ in another embodiment is $—P(OCH_2CH_2CN)N(i-Pr)_2$.

In formula (I), L represents $—OCH_2CH_2—$ or $—CH_2OCH_2—$. When L is $—OCH_2CH_2—$ in formula (I), the oxygen atom in L may bind to the carbon atom in the backbone of the compound and the carbon atom in L may bind to B, or the oxygen atom in L may bind to B and the carbon atom in L may bind to the carbon atom in the backbone of the compound. Preferably, the oxygen atom in —OCH$_2$CH$_2$— binds to the carbon atom in the backbone of the compound and the carbon atom in —OCH$_2$CH$_2$— binds to B.

The present invention in one embodiment is a compound represented by the following formula (VI) or a salt thereof. The compound can be used as a modified nucleic acid monomer instead of a natural nucleic acid monomer in the phosphoramidite method to produce an oligonucleic acid analogue containing the modified nucleic acid introduced in arbitrary position other than the 3'-terminal.

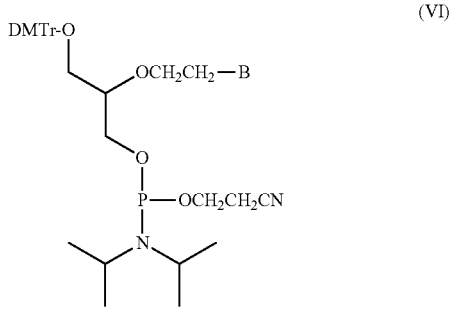

(VI)

wherein B is as defined above.

The present invention in another embodiment is a compound represented by the following formula (VII) or a salt thereof. The compound can be bound to a solid carrier having an amino group as a functional group to produce an oligonucleic acid analogue having a modified nucleic acid introduced at the 3' terminal by solid phase synthesis of the oligonucleic acid analogue.

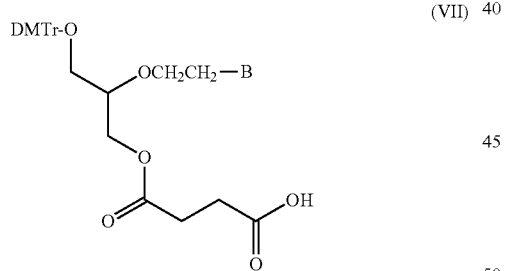

(VII)

wherein B is as defined above.

The modified nucleic acid monomer compound of formula (I) of the present invention may be in the form of salt. Examples of the salt include inorganic salts such as a sulphate salt, a nitrate salt, a perchlorate salt, a phosphate salt, a carbonate salt, a bicarbonate salt and a hydrochloride; organic carboxylate salts such as an acetate salt, an oxalate salt, a malate salt, a tartrate salt, a fumarate salt and a citrate salt; organic sulphonate salts such as a methanesulphonate salt, a trifluoromethanesulphonate salt, a toluenesulphonate salt and a camphorsulphonate salt; salts of amino acids such as an aspartate salt and a glutamate salt; quaternary amine salts; alkali metal salts such as a sodium salt and a potassium salt; and alkaline earth metal salts such as a magnesium salt and a calcium salt.

2. Production of Modified Nucleic Acid Monomer Compound

The method for producing the modified nucleic acid monomer compound of formula (I) of the present invention is hereinafter described.

Starting materials and production intermediates in the reactions indicated below may respectively be salts. Examples of the salts include those exemplified as salts of the modified nucleic acid monomer compound of formula (I) of the present invention.

In the reactions indicated below, products may be used as reaction solutions or as crude products in reactions that follow, except for the final steps. Alternatively, products may be isolated from reaction mixtures using known separation means (such as recrystallisation, distillation and chromatography) before being used in the reactions that follow. Products from final steps may be isolated and purified by similarly using known separation means and further by optionally combining the means.

2.1 Compound Wherein L is —OCH$_2$CH$_2$—

The compound of formula (I) (hereinafter also referred to as compound (I)) wherein L is —OCH$_2$CH$_2$— may be produced, for example, according to the process illustrated in reaction scheme 1 below:

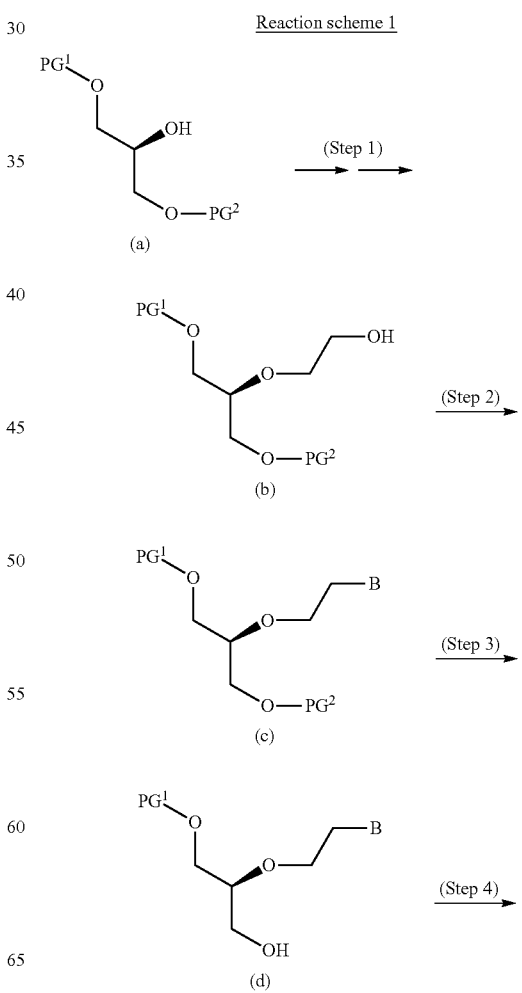

-continued

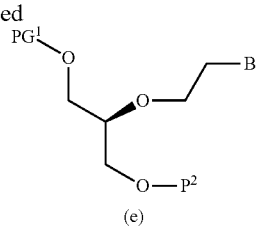

(e)

wherein B is as defined above; $PG^1$ and $PG^2$ each independently are a protective group of a hydroxy group; and $P^2$ represents a phosphorus functional group or —C(=O)CH$_2$CH$_2$COOH.

Step 1:

In the step 1, the hydroxy group in the 2-position of a glycerol compound (hereinafter referred to as compound (a)) represented by formula (a) of which 1- and 3-positions are protected as represented by $PG^1$ and $PG^2$ is converted to hydroxyethyl to produce a 2-hydroxyethyl ether compound (hereinafter referred to as compound (b)) represented by formula (b).

The compound (a) may be obtained by, for example, simultaneously or separately protecting two primary hydroxy groups of glycerol with protective groups. $PG^1$ and $PG^2$ are protective groups of hydroxy groups which may be the same or different and may be selected by referring to the reference by Greene et al. described above. When $PG^1$ and $PG^2$ are different substituents, a desired isomer having a conformation of the carbon atom in the 2-position may be obtained by a known means such as optical resolution or a chiral column.

The compound (a) may be alternatively obtained as an optically-active substance from a known optically-active 1- or 3-O-monosubstituted glycerol derivative by protecting the other 3- or 1-primary hydroxy group, respectively, with a protective group.

The compound (a) may alternatively obtained as an optically-active substance according to the method described in Examples herein, namely, from a known optically-active 1,2- or 2,3-O-disubstituted glycerol derivative by protecting 3- or 1-primary hydroxy group sequentially with a protective group followed by removal of the protective group of the hydroxy group in the 2-position and re-protecting the 1- or 3-position when needed, for example, when the protective group at the 1- or 3-position is also eliminated upon deprotection.

The step 1 may be performed by allowing reaction of, for example, the compound (a) with various 2-substituted ethylation reagent (such as 2-bromoethanol, ethylene oxide, bromoacetaldehyde dialkyl acetal or 2-haloacetate ester) in the presence of a base and then optionally converting the 2-substituted ethyl group to a 2-hydroxyethyl group.

Alternatively, when the step 1 is performed according to the method described in Examples herein, the step may be performed by allowing reaction with an allylation reagent to cleave the carbon-carbon double bond by oxidation followed by reduction treatment.

Specifically, allylation of the hydroxy group in the 2-position of the compound (a) is performed. Allylation may be performed by stirring the compound (a), an allylation reagent and a base in a solvent. Examples of the allylation reagent that may be used include allyl bromide, allyl methanesulphonate and allyl p-toluenesulphonate. Examples of the base that may be used include tertiary amines such as triethylamine and sodium hydride. The solvent is a solvent (non-reactive solvent) that is non-reactive toward the compound (a) or an alkylation reagent used and is non-reactive per se under the reaction conditions used. Examples of the non-reactive solvent include without limitation tetrahydrofuran, N,N-dimethylformamide, 1,4-dioxane, tert-butyl methyl ether, acetonitrile, benzene, toluene or mixtures thereof. The reaction temperature may be adjusted according to the reagents and solvents used, and is preferably in the range of −80° C. to 80° C. and more preferably room temperature to 50° C.

In order to obtain the compound (b), allylation is followed by cleavage of the carbon-carbon double bond by oxidation and then reduction treatment.

For cleavage of the carbon-carbon double bond by oxidation, a catalyst such as osmium tetroxide and a periodate salt, osmium tetroxide and lead tetraacetate or ruthenium tetroxide and a periodate salt may be used. In order to reoxidise the catalyst after the reaction, a reoxidising agent such as N-methylmorpholine N-oxide (NMO) may be used together with the catalyst.

The solvent used is a solvent (non-reactive solvent) that is non-reactive per se under the reaction conditions used. Examples of the non-reactive solvent include without limitation tetrahydrofuran, 1,4-dioxane, acetonitrile, carbon tetrachloride or mixtures thereof or mixtures thereof with tert-butanol and water. The reaction temperature may be adjusted according to the reagents and solvents used, and is preferably in the range of −30° C. to 80° C. and more preferably −10° C. to 50° C.

The reduction treatment is the step of producing from the produced O-substituted glutaraldehyde the compound (b), and may be performed by using a reducing agent which is a metal hydride such as sodium borohydride (NaBH$_4$), diborane (B$_2$H$_6$), diisobutylaluminium hydride (DIBAL-H), sodium cyanoborohydride (NaBH$_3$CN) and lithium triethylborohydride (LiBH(C$_2$H$_5$)$_3$) or another hydride or a complex compound thereof. The step may be performed by, for example, stirring in an organic solvent that does not inhibit the reaction such as tetrahydrofuran, diethyl ether, dichloromethane, chloroform, 1,4-dioxane, acetonitrile or toluene or in a mixed solvent of the organic solvent and water for some of the reducing agents in the presence of the reducing agent at 0° C. to 40° C. for 5 minutes to 24 hours.

Step 2:

In the step 2, a 2-heteroaryl ethyl ether compound (hereinafter referred to as compound (c)) represented by formula (c) is produced by converting the hydroxy group formed in the compound (b) to a nucleobase represented by formula B.

The step 2 may be performed by, for example, converting the hydroxy group of the 2-hydroxyethyl group introduced into the 2-position of the compound (b) to a leaving group such as a halogen, an alkylsulphonate ester or an arylsulphonate ester and allowing reaction with a heterocyclic compound represented by formula BH [wherein B is as defined above] in the presence of a base such as sodium hydride.

The step may alternatively be performed according to the method described in Examples herein, namely by treating the compound (b) and a heterocyclic compound selected from formula BH [wherein B is as defined above] with an azodicarboxylate ester such as diisopropyl azodicarboxylate (DIAD) or a triarylphosphine such as triphenylphosphine.

When the step 2 is performed according to the method described in Examples herein, the solvent used is a solvent (non-reactive solvent) that is non-reactive per se under the reaction conditions used. Examples of the non-reactive solvent include without limitation tetrahydrofuran, 1,4-dioxane, toluene, carbon tetrachloride or mixtures thereof. The reaction temperature may be adjusted according to the reagents and solvents used, and is preferably in the range of 0° C. to 100° C. and more preferably 10° C. to 80° C. The reaction atmosphere is not particularly limited and the reaction is preferably performed under an inert atmosphere such as a nitrogen atmosphere or an argon atmosphere.

The protective groups ($R^2$ to $R^6$) in the heterocyclic compound of formula BH may be converted to a desired protective group or a hydrogen atom by performing deprotection and/or protection after the reaction with the compound (b). As described in, for example, Example 6 hereinbelow, BH wherein the protective groups ($R^2$ to $R^6$) are Boc may be allowed to react with the compound (b) followed by deprotection of the Boc groups and protection with different protective groups ($R^2$ to $R^6$) such as Bz.

In the heterocyclic compound of formula BH, $R^2$ and $R^4$ may be each independently $C_{1-6}$ alkyl, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl or $C_{6-14}$ arylsulphonyl, and $R^3$, $R^5$ and $R^6$ may be each independently $C_{1-6}$ alkyl, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl or $C_{6-14}$ arylsulphonyl. The compound may be a commercially available material or may be produced according to methods known to a person skilled in the art. For example, examples of nucleobases modified with $R^2$ to $R^6$ are disclosed in references such as 1) Englisch, U. and Gauss, D. H., Angew. Chem. Int. Ed. 1991, 30, 613-622; and 2) Lee, S. H. et al., Nucleic Acids Research, 29, 1565-1573, 2001. For example, various modified bases are disclosed on page 623 of the reference 1), and more than one modified base and production method are disclosed on page 1569 of reference 2). A person skilled in the art can obtain BH having $R^2$ to $R^6$ as above by referring to and/or modifying the modified bases disclosed in the references.

The protective groups of, for example, $PG^1$ and/or $PG^2$ may be deprotected during reactions. In this case, after the reactions, $P^G$ and/or $PG^2$ may be again protected.

Step 3:

In the step 3, $PG^2$ that is protecting the hydroxy group in the 3-position of the compound (c) is deprotected to produce a compound (hereinafter referred to as compound (d)) represented by formula (d). The reaction conditions for eliminating the protective group vary according to the type of the protective group $PG^2$, and may be selected by referring to the reference by Greene et al. described above.

For example, when $PG^2$ is a silyl protective group such as TBDMS, deprotection may be performed with a fluoride salt or an adduct of hydrogen fluoride. Examples thereof include a process in which tetra-n-butylammonium fluoride (TBAF) is allowed to work in a solvent. The solvent used is a solvent (non-reactive solvent) that is non-reactive per se under the reaction conditions used. Examples of the non-reactive solvent include without limitation tetrahydrofuran, 1,4-dioxane, acetonitrile, toluene, methylene chloride or mixtures thereof.

Step 4 (1):

In the step 4, the hydroxy group in the 3-position of the compound (d) is converted to $P^2$ which is a phosphorus functional group or —C(=O)CH$_2$CH$_2$COOH to produce a compound (hereinafter referred to as compound (e)) represented by formula (e).

When $P^2$ is a phosphorus functional group, examples of the phosphorus functional group include phosphorus functional groups which are phosphoric acid reactive groups upon production of the oligonucleic acid analogue of formula (VII) using the modified nucleic acid monomer compound of formula (I) by the triester method, the phosphoramidite method, a method in which a dichlorophosphine derivative is used, the H-phosphonate method and the like which are known nucleic acid synthesis methods.

Conversion of the phosphoric acid reactive group to phosphoramidite that is described in Examples herein in the step 4 is specifically described.

The conversion reaction to the phosphorus functional group of formula (i) described above as the phosphorus functional group in $P^2$ may be performed by, for example, allowing reaction of a corresponding phosphorylation reagent represented by the following formula (i'):

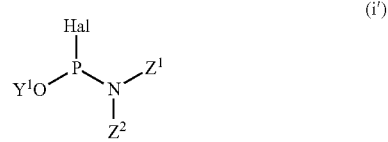

wherein Hal represents a halogen atom and $Y^1$, $Z^1$ and $Z^2$ are as defined above; with the compound (d). The reaction may be performed by, for example, dissolving in a solvent that does not inhibit the reaction such as tetrahydrofuran, N,N-dimethylformamide, chloroform, 1,4-dioxane, acetonitrile, toluene and methylene chloride and optionally stirring in the presence of, for example, triethylamine, tributylamine, N,N-diisopropylethylamine (DIPEA), collidine or 2,6-lutidine at room temperature for 5 minutes to 24 hours.

Step 4 (2):

When $P^2$ is —C(=O)CH$_2$CH$_2$COOH, the step 4 is a step in which the hydroxy group in the 3-position of the compound (d) is converted to a monoester compound (e) of succinic acid. For example, production may be carried out by allowing reaction of the compound (d) with succinic anhydride in the presence of a base. Production may alternatively be carried out by condensing the compound (d) and a derivative of succinic acid in which one of the carboxylic acids is protected such as a succinate monoester in the presence of an activating agent or condensation agent such as dicyclohexylcarbodiimide, 1-[3-(dimethylamino)propyl]-3-ethylcarbodiimide, N,N'-carbonyldiimidazole or triphenylphosphine-diethyl azodicarboxylate followed by elimination of the protective group. The reaction conditions for eliminating the protective group on succinic acid may vary according to the type of the protective group, and may be selected by referring to the reference by Greene et al. described above.

According to the method described above, the compound (e) may be produced.

The compound (e) may be labelled with an isotope (such as $^3$H, $^{11}$C, $^{14}$C, $^{18}$F, $^{35}$S or $^{125}$I) or the like, and the compound (e) also encompasses compounds labelled with the isotope or the like.

In the compound (e), $^1$H may further be converted to $^2$H(D), and the compound (e) also encompasses deuterium converted products which underwent such conversion.

The compound (e) may also be a solvate (such as hydrate) or a non-solvate both of which are encompassed by the compound (e).

2.2 Compound Wherein L is —CH$_2$OCH$_2$—

The compound (I) wherein L is —CH$_2$OCH$_2$— may be produced, for example, according to the process illustrated in reaction scheme 2 below:

Reaction scheme 2

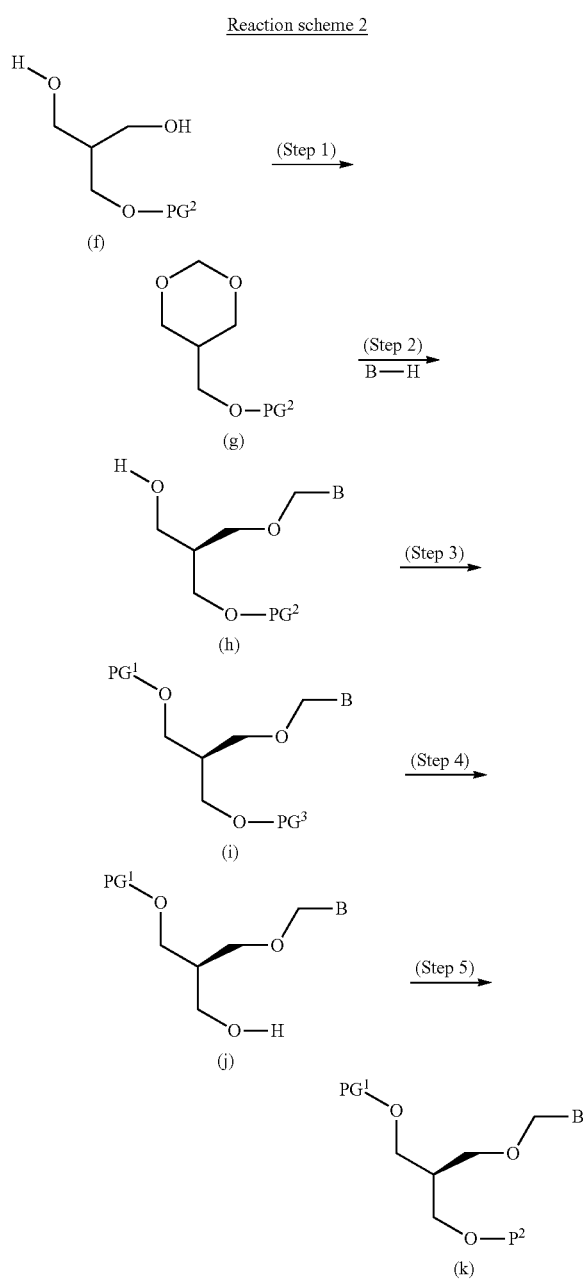

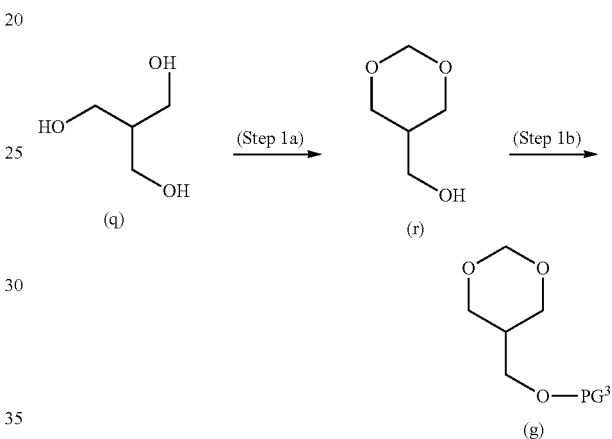

wherein B and PG$^1$ are as defined above; and PG$^3$ represents a protective group of a hydroxy group.

Step 1:

In the step 1, a ring is formed by dehydration through a methylene group with two unprotected hydroxy groups of 2-(protected)hydroxymethyl-1,3-propanediol (hereinafter referred to as compound (f)) represented by formula (f) in which one hydroxy group is protected with the protective group represented by PG$^3$ to produce a 1,3-dioxane compound (hereinafter referred to as compound (g)) represented by formula (g).

The compound (f) may be obtained by, for example, protecting one of three primary hydroxy groups of 2-hydroxymethyl-1,3-propanediol with a protective group PG$^3$. PG$^3$ can be selected by referring to the reference by Greene et al. described above.

The step 1 may be performed by, for example, allowing reaction of the compound (f) with a formaldehyde derivative (such as para-formaldehyde, trioxane or formaldehyde dialkyl acetal) in the presence of an acid. The acid that may be used is an inorganic acid such as hydrochloric acid and sulphuric acid; an organic acid such as p-toluenesulphonic acid and camphorsulphonic acid; or a Lewis acid such as tin(II) chloride and zinc chloride. In order to increase the reaction selectivity, lithium bromide may be used. The solvent used is a solvent (non-reactive solvent) that is non-reactive per se under the reaction conditions used. Examples of the non-reactive solvent include without limitation tetrahydrofuran, 1,4-dioxane, acetonitrile, toluene, methylene chloride or mixtures thereof.

As an alternative method to the above step 1, the compound (g) may be obtained by the following steps as, for example, described in Examples:

(Step 1')

In the step 1a, a ring is formed by dehydration through a methylene group with two hydroxy groups of 2-hydroxymethyl-1,3-propanediol (hereinafter referred to as compound (q)) to produce a 1,3-dioxane compound (hereinafter referred to as compound (r)) represented by formula (r). For example, the step may be performed by, for example, allowing reaction of the compound (q) with a formaldehyde derivative (such as para-formaldehyde, trioxane and formaldehyde dialkyl acetal) in the presence of an acid. The acid that may be used is an inorganic acid such as hydrochloric acid and sulphuric acid; an organic acid such as p-toluenesulphonic acid and camphorsulphonic acid; or a Lewis acid such as tin(II) chloride and zinc chloride. In order to increase the reaction selectivity, lithium bromide may be used. The solvent used is a solvent (non-reactive solvent) that is non-reactive per se under the reaction conditions used. Examples of the non-reactive solvent include without limitation tetrahydrofuran, 1,4-dioxane, acetonitrile, toluene, methylene chloride or mixtures thereof.

In the step 1b, a compound (hereinafter referred to as compound (g)) represented by formula (g) in which the remaining hydroxy group of the compound (r) is protected with a protective group PG$^3$ is produced. The reaction conditions for protecting the hydroxy group may vary according to the type of the protective group PG$^3$, and may be selected by referring to the reference by Greene et al. described above.

Step 2:

In the step 2, the compound (g) and a nucleobase or a derivative thereof are allowed to react in the presence of an acid to produce a compound (hereinafter referred to as compound (h)) represented by formula (h). The acid that may be used is an inorganic acid such as hydrochloric acid and sulphuric acid; an organic acid such as p-toluenesulphonic acid and camphorsulphonic acid; or a Lewis acid such as tin(II) chloride, zinc chloride, trialkylsilyl trifluoromethanesulphonate and tert-butyldiphenylsilyl triflate. The nucleobase may be used as it is, or may be preliminarily subjected to trialkylsilylation reaction with a silylating agent before reaction thereof with the compound (h) or may be allowed to react with the compound (h) in the presence of the silylating agent. The silylating agent that may be used is chlorotrimethylsilane, N,O-bis(trimethylsilyl)acetamide and the like. The solvent used is a solvent (non-reactive solvent) that is non-reactive per se under the reaction conditions used. Examples of the non-reactive solvent include without limitation tetrahydrofuran, 1,4-dioxane, acetonitrile, toluene, 1,2-dichloroethane or mixtures thereof.

Step 3:

In the step 3, a compound (hereinafter referred to as compound (i)) represented by formula (i) is produced by protecting the hydroxy group in the 1-position of the compound (h) with a protective group $PG^1$. The reaction conditions for protecting the hydroxy group may vary according to the type of the protective group $PG^1$, and may be selected by referring to the reference by Greene et al. described above.

Step 4:

In the step 4, $PG^3$ that is protecting the hydroxy group in the 3-position of the compound (i) is deprotected to produce a compound (hereinafter referred to as compound (j)) represented by formula (j). The reaction conditions for eliminating the protective group may vary according to the type of the protective group $PG^3$, and may be selected by referring to the reference by Greene et al. described above.

Step 5

In the step 5, the hydroxy group in the 3-position of the compound (j) is converted to $P^2$ which is a phosphorus functional group or $-C(=O)CH_2CH_2COOH$ to produce a compound (hereinafter refers to as compound (k)) represented by formula (k).

This step may be performed in the same manner as the step 4 in the scheme 1 by using the compound (j) as a starting substance.

The compound (I) wherein L is $-CH_2OCH_2-$ may alternatively be produced, for example, according to the process illustrated in reaction scheme 3 below:

Reaction scheme 3

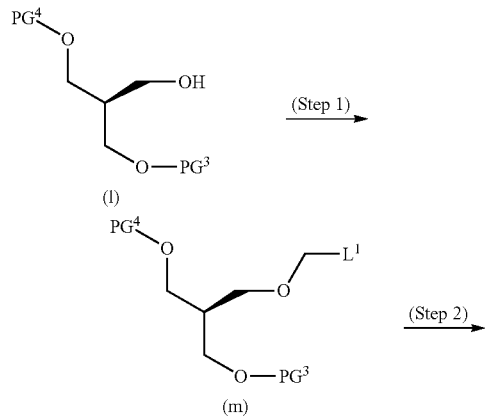

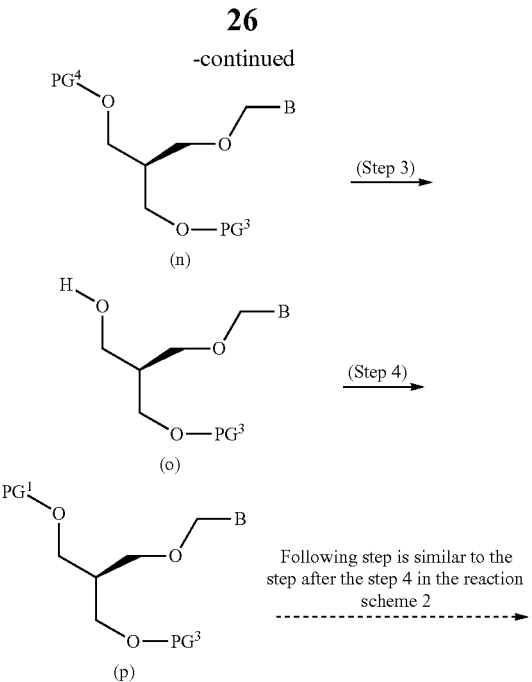

Following step is similar to the step after the step 4 in the reaction scheme 2 wherein B, $PG^1$ and $PG^3$ are as defined above; $L^1$ is alkoxy (such as methoxy or ethoxy) or a leaving group; and $PG^4$ represents a protective group of a hydroxy group.

Step 1:

In the step 1, a hydrogen atom of the remaining hydroxy group of 2-hydroxymethyl-1,3-propanediol (hereinafter referred to as compound (1)) represented by formula (I) in which hydroxy groups at the 1- and 3-positions are protected with protective groups represented by $PG^4$ and $PG^3$, respectively, is substituted by methyl substituted by $L^1$ to produce a compound (hereinafter referred to as compound (m)) represented by formula (m).

$PG^3$ and $PG^4$ are protective groups of hydroxy groups which may be the same or different, and may be selected by referring to the reference by Greene et al. described above.

$L^1$ is alkoxy (such as methoxy or ethoxy), acyloxy (such as acetoxy) or a leaving group. The leaving group is not particularly limited and examples thereof include a halogen atom, a tosyl group or the like.

The starting substance, compound (1), may be obtained by, for example, simultaneously or separately protecting two of three primary hydroxy groups of 2-hydroxymethyl-1,3-propanediol with protective groups. When $PG^3$ and $PG^4$ are different substituents, an isomer having a desired conformation of the carbon atom in the 2-position may be obtained by a known means such as optical resolution or a chiral column.

Alternatively, an optically active compound (1') which is 2-hydroxymethyl-1,3-propanediol in which two of three primary hydroxy groups are protected with different protective groups may be obtained by, for example, asymmetrical hydrolysis using an enzyme (Liebigs Ann. Chem. 1990, 379-388, Org. Process Res. Dev. 2012, 16, 1527-1537). The compound (1') may be used as it is as an optically active compound (1) depending on the reaction conditions in the following steps, or alternatively, an optically active compound (1) having a desired protective group may be obtained by known protection/deprotection means.

The step 1 may be performed by allowing reaction of the compound (1) with a formaldehyde derivative such as para-formaldehyde or trioxane in the presence of an acid, thereby obtaining the compound (m) wherein $L^1$ is a leaving group. The acid that may be used is hydrogen chloride or the like.

The solvent used in the step 1 a solvent (non-reactive solvent) that is non-reactive toward the compound (1), the formaldehyde derivative and the acid used and is non-reactive per se under the reaction conditions used. Examples of the non-reactive solvent include without limitation benzene, toluene, 1,4-dioxane or dichloromethane. The reaction temperature may be adjusted according to the reagents and solvents used, and is preferably in the range of −30° C. to 50° C. and more preferably −10° C. to 30° C.

The step 1 may alternatively performed by allowing reaction of the compound (1) with MOMCl in the presence of a trialkylamine and sodium iodide, thereby obtaining the compound (m) in which $L^1$ is a methoxy group. The solvent used is a solvent (non-reactive solvent) that is non-reactive per se under the reaction conditions used. Examples of the non-reactive solvent include without limitation tetrahydrofuran, 1,4-dioxane, 1,2-dimethoxyethane or mixtures thereof. The reaction temperature may be adjusted according to the reagents and solvents used, and is preferably in the range of 0° C. to the reflux temperature and more preferably room temperature to 100° C.

Step 2:

In the step 2, the compound (m) and a nucleobase BH are allowed to react to produce a compound (hereinafter referred to as compound (n)) represented by formula (n). When $L^1$ is a leaving group in the compound (m), the compound (m) and a nucleobase BH are allowed to react in the presence of a base to produce the compound (n). The base that may be used is an inorganic base such as sodium carbonate or an organic base such as triethylamine.

The solvent used in the step 2 is a solvent (non-reactive solvent) that is non-reactive toward the compound (m) and the base used and is non-reactive per se under the reaction conditions used. Examples of the non-reactive solvent include without limitation tetrahydrofuran, N,N-dimethylformamide, acetone, chloroform, 1,4-dioxane, benzene, toluene or dichloromethane. The reaction temperature may be adjusted according to the reagents and solvents used, and is preferably in the range of −30° C. to 80° C. and more preferably −10° C. to 50° C.

When $L^1$ is a methoxy group in the compound (m), the step 2 may be performed in the same manner as in synthesis of the compound (h) described above, namely the step 2 in the scheme 2.

Step 3:

In the step 3, the hydroxy group $PG^4$ in the 1-position of the compound (n) is deprotected to produce a 1-alcohol (hereinafter referred to as compound (o)) represented by formula (o). The reaction conditions for eliminating the protective group vary according to the type of the protective group $PG^4$, and may be selected by referring to the reference by Greene et al. described above.

Step 4:

In the step 4, a compound (hereinafter referred to as compound (p)) represented by formula (p) is produced by protecting the hydroxy group in the 1-position of the compound (o) with a protective group $PG^1$. The reaction conditions for protecting the hydroxy group may vary according to the type of the protective group $PG^1$, and may be selected by referring to the reference by Greene et al. described above.

From the compound (p) produced in the step 4, an object substance (k) may be obtained through the step after the step 4 in the reaction scheme 2.

3. Modified Nucleic Acid Monomer Compound-Carrying Substance

The present invention in one embodiment provides a modified nucleic acid monomer-carrying substance containing a monovalent group derived from the modified nucleic acid monomer compound represented by formula (I) supported on a solid carrier through an amino group on the carrier.

In one embodiment, a modified nucleic acid monomer-carrying substance is provided containing a monovalent group derived from the modified nucleic acid monomer compound represented by the following formula (VIII) supported on a solid carrier through an amino group on the carrier.

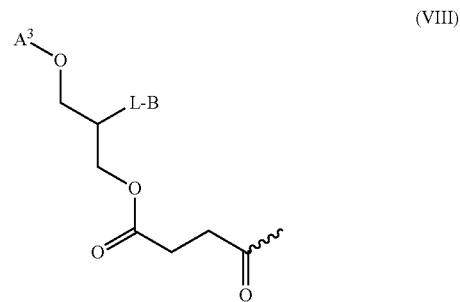

(VIII)

In formula (VIII), L and B are as defined above.

In formula (VIII), $A^3$ is a hydrogen atom or a protective group of a hydroxy group. $A^3$ is as defined above for $A^1$ except that $A^3$ may be a hydrogen atom, and specific embodiments described above for $A^1$ may be similarly applied to $A^3$. In one embodiment, $A^3$ is a protective group of a hydroxy group selected from trityl, 4-methoxytrityl, 4,4'-dimethoxytrityl (DMTr) and 4,4',4''-trimethoxytrityl.

The solid carrier used is, for example, an inorganic carrier such as CPG (controlled pore glass) or silica gel; or a polymer carrier such as HCP (highly cross-linked polystyrene).

The monovalent group represented by formula (VIII) above is derived from the modified nucleic acid monomer compound of formula (I) wherein $A^2$ is —C(=O)CH$_2$CH$_2$COOH. Through the binding reaction of the carboxyl group of $A^2$ and an amino group on the solid carrier, the monovalent group of formula (VIII) may be supported on the solid carrier through the amino group.

A modified nucleic acid monomer-carrying substance containing the modified nucleic acid monomer compound of formula (I) wherein $A^2$ is —C(=O)CH$_2$CH$_2$COOH supported on a solid carrier through an amino group on the carrier may be produced, for example, according to the process illustrated in reaction scheme 4 below:

Reaction scheme 4

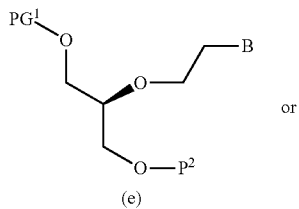

(e)

or

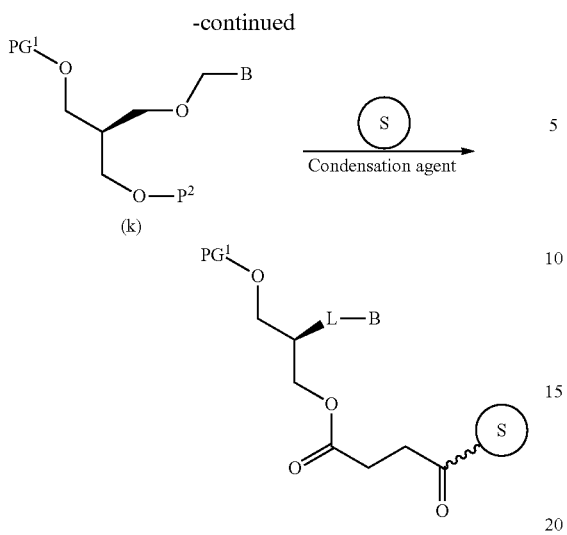

(k)

wherein B and L are as defined above; $PG^1$ is a protective group of a hydroxy group; $P^2$ is $-C(=O)CH_2CH_2COOH$; and S represents a carrier.

In the present step, a modified nucleic acid monomer-carrying substance that is a starting material for an oligo solid phase synthesis method is produced by binding reaction between the compound (e) or compound (k) wherein $P^2$ is $-C(=O)CH_2CH_2COOH$ and a solid carrier having an amino group as a functional group.

Specifically, the compound (e) or compound (k) is allowed to react with a solid carrier having an amino group as a functional group in a solvent in the presence of a condensation agent and a base to obtain a carrying substance containing a monovalent group derived from the modified nucleic acid monomer compound (compound of formula (VIII) wherein $A^3$ is a protective group (PG1) of a hydroxy group) immobilised on the carrier. The carrying substance may be introduced without treatment as a starting material for a nucleic acid oligomer to an automated nucleic acid synthesiser.

By subjecting $PG^1$ to deprotection reaction, a carrying substance containing the compound of formula (VIII) wherein $A^3$ is a hydrogen atom immobilised on the carrier may be obtained.

The solid carrier having an amino group as a functional group that may be used is a commercially available product such as Amino LCAA CPG support and TentaGel™ (R) N $NH_2$ manufactured by ChemGenes.

The solvent used is a solvent (non-reactive solvent) that is non-reactive per se under the reaction conditions used. Examples of the non-reactive solvent include without limitation tetrahydrofuran, 1,4-dioxane, acetonitrile, toluene, methylene chloride or mixtures thereof.

Examples of the condensation agent include 1-[3-(dimethylamino)propyl]-3-ethylcarbodiimide (EDC), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[bis(dimethylamino)methylene]-5-chloro-1H-benzobenzotriazolium-3-oxide hexafluorophosphate (HCTU) and hydrochlorides thereof.

Examples of the base include N,N-diisopropylethylamine (DIPEA), triethylamine, pyridine, 4-dimethylaminopyridine, N-methylimidazole or mixtures thereof.

The obtained modified nucleic acid monomer-carrying substance may be optionally subjected to capping treatment according to a known method. For example, an unreacted carboxy group may be capped by esterification with an alcohol such as methanol and ethanol in the solvent in the presence of the condensation agent and the base. An unreacted $-OH$ group or $-NH_2$ group may be capped by reaction with acetic anhydride for acetylation in the solvent in the presence of the base.

4. Oligonucleic Acid Analogue

The present invention in one embodiment provides an oligonucleic acid analogue containing the monomer compound as at least one of building blocks.

The oligonucleic acid analogue in one embodiment is an oligonucleic acid analogue containing one or more partial structures represented by formula (IX) or a salt thereof,

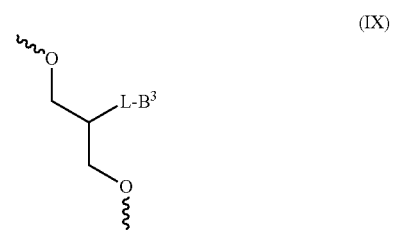

provided that when two or more partial structures are included, $B^3$ and L in the partial structures may be respectively the same or different.

In formula (IX), L is as defined above.
In formula (IX), $B^3$ is a nucleobase.

$B^3$ in one embodiment is a nucleobase selected from the following formulae (II)', (III)', (IV)' and (V)':

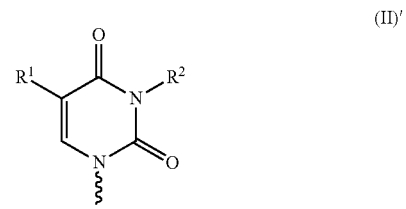

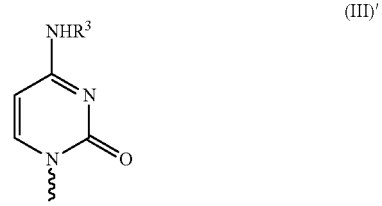

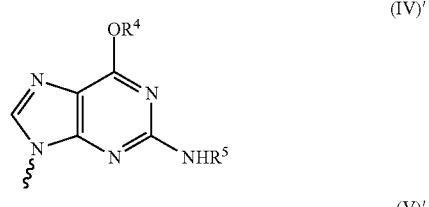

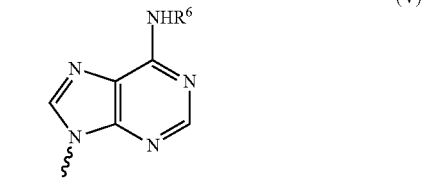

In formulae (II)' to (V)', $R^1$ represents a hydrogen atom or methyl.

In formulae (II)' to (V)', $R^2$ and $R^4$ each independently represent a hydrogen atom, $C_{1-6}$ alkyl, $C_{1-6}$ alkoxy, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl, $C_{6-14}$ arylsulphonyl or a protective group.

In formulae (II)' to (V)', $R^3$, $R^5$ and $R^6$ each independently represent a hydrogen atom, $C_{1-6}$ alkyl, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl, $C_{6-14}$ arylsulphonyl or a protective group.

$B^3$ above is as defined above for B except that $R^3$, $R^5$ and $R^6$ may be each independently a hydrogen atom. Specific embodiments described above for B and specific embodiments in which $R^3$, $R^5$ and $R^6$ are substituted by hydrogen atoms may be similarly applied. An oligonucleic acid analogue having a partial structure in which $R^3$, $R^5$ and $R^6$ are substituted by hydrogen atoms may be obtained by, for example, forming an oligomer comprising monomer compounds sequentially incorporated therein by the solid phase method described hereinafter and then eliminating protective groups using a known deprotection means before or after cleavage from the solid carrier.

In one embodiment, $B^3$ is selected from the following formulae (X), (XI), (XII) and (XIII):

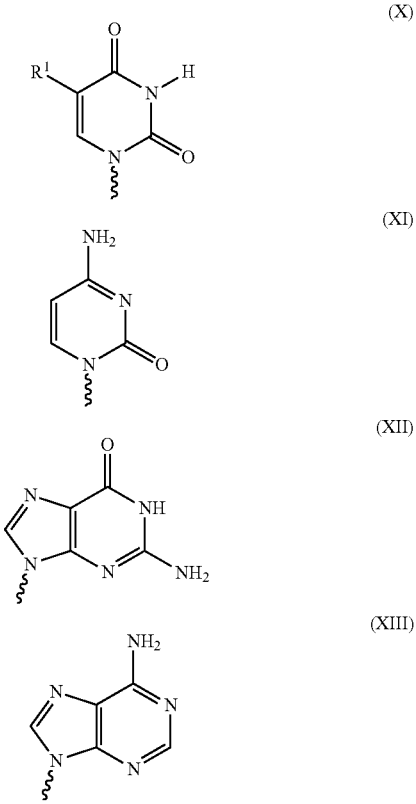

wherein $R^1$ is as defined above.

The oligonucleic acid analogue of the embodiment is an oligonucleic acid analogue containing one or more partial structures of formula (IX) corresponding to the modified nucleic acid monomer compound of formula (I). However, as stated above, in the oligonucleic acid analogue of the embodiment, at least one of $R^3$, $R^5$ and $R^6$ in formula (I) may be a hydrogen atom unlike the modified nucleic acid monomer compound of formula (I).

In one embodiment, the oligonucleic acid analogue of the present invention contains one partial structure of formula (IX). In another embodiment, the oligonucleic acid analogue of the present invention contains one partial structure as above wherein L is —$OCH_2CH_2$—. In still another embodiment, the oligonucleic acid analogue contains two or more partial structures as above respectively in which L is —$OCH_2CH_2$—. In another embodiment, the oligonucleic acid analogue contains two or more partial structures as above respectively in which L is —$OCH_2CH_2$— and respectively which have the same absolute configuration of the 2-position carbon.

The oligonucleic acid analogue of the present invention may contain one or more partial structures of formula (IX) and may further contain a nucleoside subunit (nucleobase unit) other than formula (IX).

The nucleoside subunit other than the partial structure of formula (IX) may be a ribonucleoside or a deoxyribonucleoside. The term "nucleoside subunit" as used herein encompasses a building block having the partial structure of formula (IX).

When the subunit is a ribonucleoside, the ribose moiety may be a known derivative such as 2'-O-methylribose or 2'-fluororibose.

The base moiety of the nucleoside subunit may be any of adenine, guanine, cytosine, uracil or thymine or may be a modified base. Examples of the modified base moiety include modified base moieties known to a person skilled in the art in which the base moiety is substituted by a halogen atom, a $C_{1-6}$ alkyl group, a $C_{1-6}$ alkoxy group, a $C_{2-6}$ alkenyl group, a $C_{2-6}$ alkynyl group, a $C_{1-6}$ alkyl-carbonyl group, a $C_{1-6}$ alkylthio group, a $C_{1-6}$ alkylsulphonyl group, a $C_{6-14}$ aryloxy-carbonyl group, a $C_{6-14}$ aryl-carbonyl group, a $C_{6-14}$ arylsulphonyl group, an amino group, a mono-$C_{1-6}$ alkylamino group, a di-$C_{1-6}$ alkylamino group, a nitro group, a hydroxy group, a cyano group, a carboxy group or the like.

The total number of nucleoside subunits (total number of nucleobase units) that form the oligonucleic acid analogue of the present invention in one embodiment is 4 to 100 per strand. In another embodiment, the total number is 4 to 30 per strand.

When, for example, the oligonucleic acid analogue is DNA, the total number in one embodiment is 4 to 100 per strand and in another embodiment 4 to 30 per strand.

When the oligonucleic acid analogue is RNA, the total number in one embodiment is 4 to 50 per strand and in another embodiment, 4 to 30 per strand. The partial structures of formula (IX) as subunits are included at an integer number corresponding to the range of 1% to 100% relative to the total number of the nucleic acid subunits in the oligonucleic acid analogue in one embodiment, at an integer number corresponding to the range of 2% to 80% relative to the total number of the subunits in another embodiment, at an integer number corresponding to the range of 2% to 50% in still another embodiment and at an integer number corresponding to 2% to 25% in yet another embodiment. In one embodiment, 1 to 10 (more preferably 1 to 8 and still more preferably 1 to 4) partial structures of formula (IX) are included relative to the total number of 4 to 30 (more preferably 4 to 25 and still more preferably 4 to 21) subunits per strand. The positions thereof in the oligonucleic acid analogue are not limited and may be arbitrarily selected according to the purpose of use.

Nucleosides in natural oligonucleotides and polynucleotides are linked through phosphodiester bonds illustrated in (XIV) below. In the oligonucleic acid analogue of the present invention, nucleoside subunits are linked through any of the phosphodiester bond (formula (XIV)) or phosphorothioate bond (formula (XV)) between nucleosides. The phosphorothioate may be present as tautomers of (a) and (b) in some solvents.

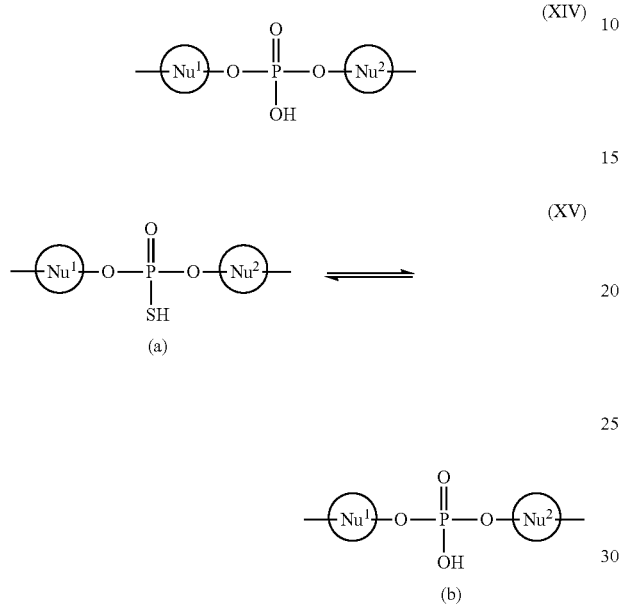

In each formula, Nu$^1$ and Nu$^2$ respectively represent a nucleoside subunit.

The oligonucleic acid analogue of the present invention may be in the form of salt. Examples of the salt include the salts of the modified nucleic acid monomer compound of formula (I) of the present invention as described above.

The oligonucleic acid analogue of the embodiment more specifically contains, in for example an oligonucleic acid analogue represented by the following formula (XVI):

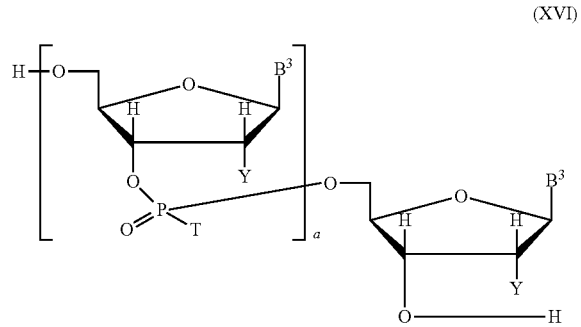

wherein Y represents H, OH, OMe or F; B$^3$ is as defined above; a represents an integer of 3 to 99; T represents OH or SH; and Y, B$^3$ and T in respective building blocks may be the same of different;

one or more structures (i.e., partial structures selected from the following formulae (XVII) and (XVIII)) containing the partial structure represented by the following formula (IX):

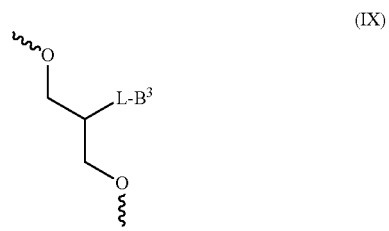

wherein L and B$^3$ are as defined above;
instead of one or more structural units at arbitrary positions.

The letter a in one embodiment is an integer of 3 to 49 and in another embodiment an integer of 3 to 29.

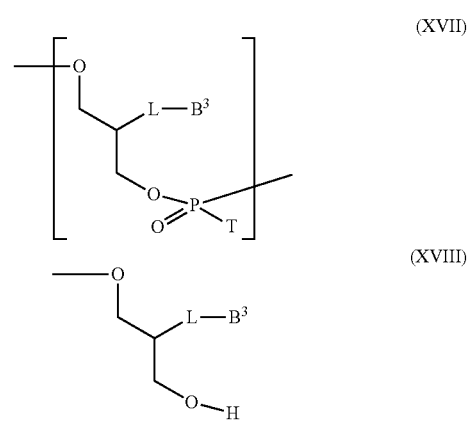

wherein T, B$^3$ and L are as defined above; when two or more partial structures above are included, B$^3$ and L in the partial structures may be the same or different.

The oligonucleic acid analogue of the present invention may be used as, for example, siRNA (small interfering RNA), miRNA (micro RNA), shRNA (short hairpin RNA or small hairpin RNA), antisense RNA, antisense DNA or the like.

Therefore, the oligonucleic acid analogue of the present invention may be, according to the application, a single-stranded oligonucleotide or a double-stranded oligonucleotide, and may be a single-stranded DNA, a double-stranded DNA, a single-stranded RNA, a double-stranded RNA, a DNA/RNA chimera or a DNA/RNA hybrid.

When the oligonucleic acid analogue of the present invention is used as, for example, siRNA, the oligonucleic acid analogue is preferably a double-stranded RNA consisting of sense and antisense strands of a target gene or modifications thereof, and the partial structure of formula (I) of the present invention may be included in either or both of the sense and antisense strands or modifications thereof. The modification in this context includes those containing modified base moieties, modified sugar moieties of nucleosides described hereinabove and various phosphodiester bonds that do not occur naturally siRNA may have a double strand formed from a sense strand and an antisense strand that are hybridised to have dangling ends made of 2 to 5 ribonucleotides or deoxyribonucleotides or known modified nucleotides at both 3'-termini.

5. Production of Oligonucleic Acid Analogue

The oligonucleic acid analogue of the present invention may be produced using the modified nucleic acid monomer compound of formula (VI) or formula (VII) by a solid phase or liquid phase method according to the triester method, the phosphoramidite method, a method in which a dichlorophosphine derivative is used, the H-phosphonate method and the like which are known nucleic acid synthesis methods. The production may be performed on an automated nucleic acid synthesiser (N. Usman et al., J. Am. Chem. Soc., 109(25), 7845-7854 (1987), Tetrahedron Lett., 25(7), 713-716 (1984)).

For example, the solid phase method according to the phosphoramidite method may be performed as indicated below:

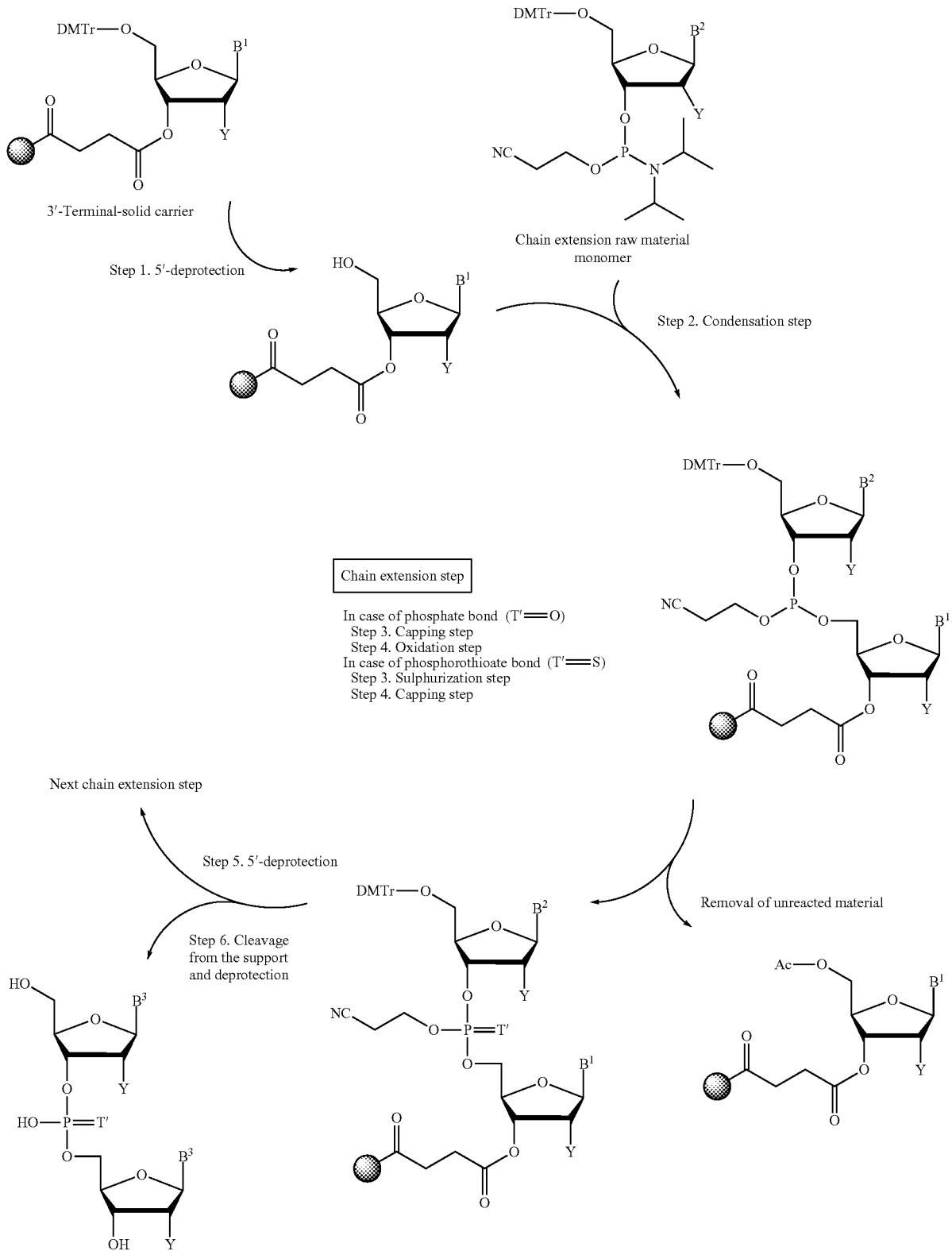

 = Solid carrier (such as CPG)

-continued wherein Y represents H, OH, OMe or F; $B^1$ and $B^2$ respectively have the same definitions as B; $B^3$ is as defined above; T' represents O or S; and Y and T in respective building blocks may be the same of different.

In the solid phase method, the hydroxy group (OH) in Y may be converted to a desired protective group using known protection/deprotection means to produce the oligonucleic acid analogue.

By using, for example, the modified nucleic acid monomer compound of formula (VI) of the present invention as the chain extension raw material in the above solid phase method and/or the modified nucleic acid monomer-carrying substance of formula (VIII) as the 3'-terminal polymer support, the oligonucleic acid analogue containing one or more partial structures represented by formula (IX) at an arbitrary position may be produced. The chain extension raw material that may be used is, in addition to the modified nucleic acid monomer compound of formula (VI), a compound of formula (I) wherein $A^2$ is a phosphorus functional group (preferably —P(—$OR^7$)—$NRR^9$).

The obtained crude oligonucleotide product may be isolated/purified according to a known method such as reverse phase or ion exchange chromatography, and deprotection and purification may be both performed by further combining known methods, if necessary.

When solid phase synthesis is performed, the solid carrier to which the oligonucleotide block binds that may be used is, for example, an inorganic carrier such as CPG (controlled pore glass) or silica gel; or a polymer carrier such as HCP (highly cross-linked polystyrene). The solid carrier that may be used alternatively is the polymer carrier described above to which a linker (such as a terminal amine linker and a succinate ester linker) is linked.

For example, the modified nucleic acid monomer-carrying substance containing a monovalent group derived from the modified nucleic acid monomer compound represented by formula (VIII) described above supported on the solid carrier through an amino group on the carrier may be used for production of an oligonucleic acid analogue (see example schemes 1 and 2):

Example Scheme 1

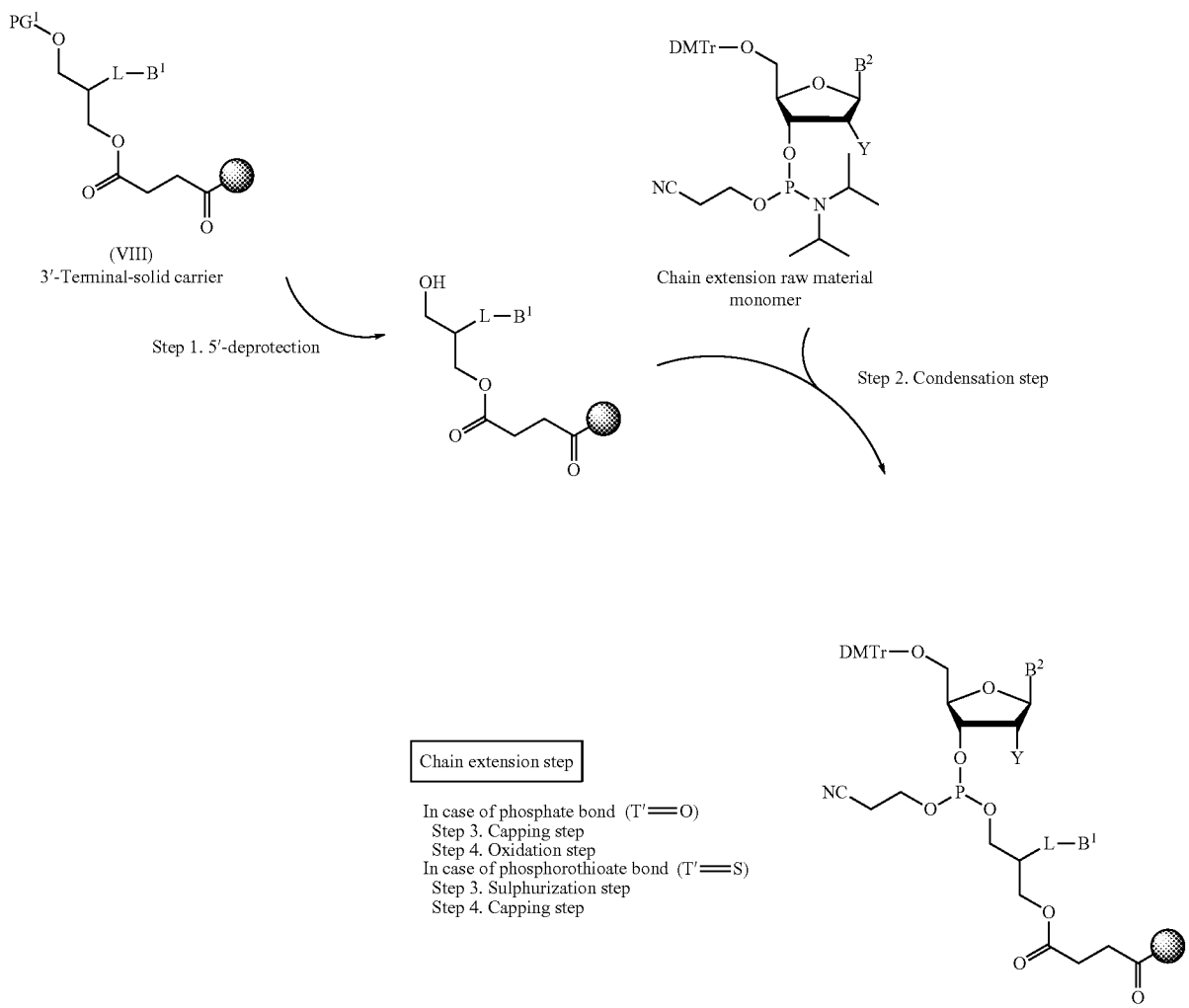

-continued

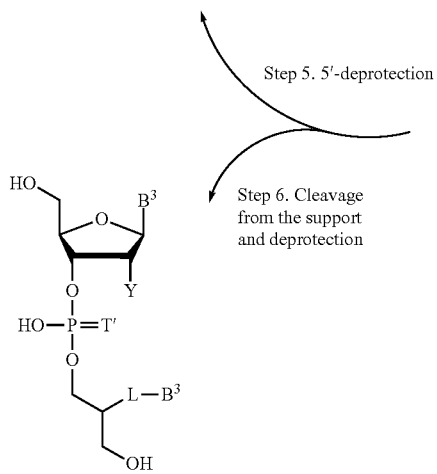
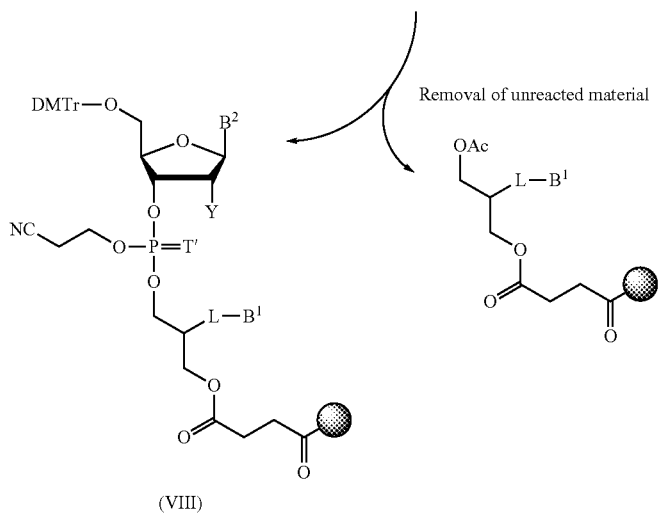

◉ = Solid carrier (such as CPG)

wherein $PG^1$, Y, $B^1$, $B^2$, $B^3$, T' and L are as defined above.

As illustrated in the example scheme 1, the modified nucleic acid monomer compound represented by formula (VIII) and the chain extension raw material monomer are subjected to condensation reaction followed by the oxidation or sulphurization step, thereby linking nucleoside subunits through a phosphodiester bond or a phosphorothioate bond. By repeating the chain extension step (steps 2 to 5 in the example scheme 1 above or steps 2 to 5 in the example scheme 2 below), an oligonucleotide block containing a plurality of nucleoside subunits linked together may be obtained. Production of the oligonucleotide block may be followed by cleavage from the support and deprotection reaction to obtain the oligonucleic acid analogue of the embodiment. By using the modified nucleic acid monomer compound represented by formula (VI) as the chain extension raw material monomer in an arbitrary number of times among the repetition of the chain extension step, the oligonucleic acid analogue containing one or more arbitrary number of partial structures represented by formula (IX) at the 3'-terminal and an arbitrary position other than the 3'-terminal may be obtained.

Example Scheme 2

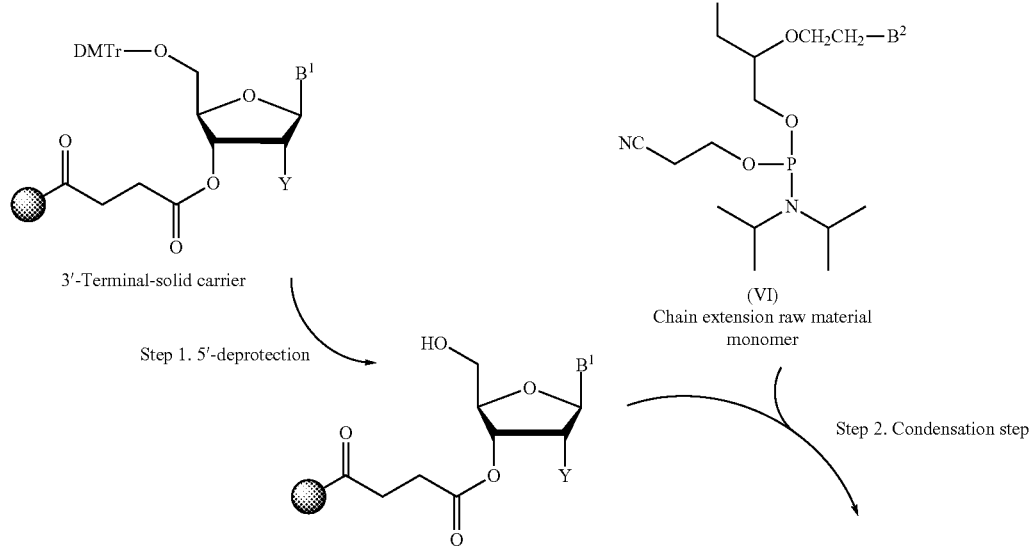

-continued

Chain extension step

In case of phosphate bond (T'═O)
  Step 3. Capping step
  Step 4. Oxidation step
In case of phosphorothioate bond (T'═S)
  Step 3. Sulphurization step
  Step 4. Capping step

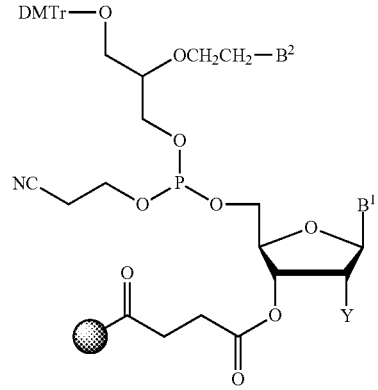

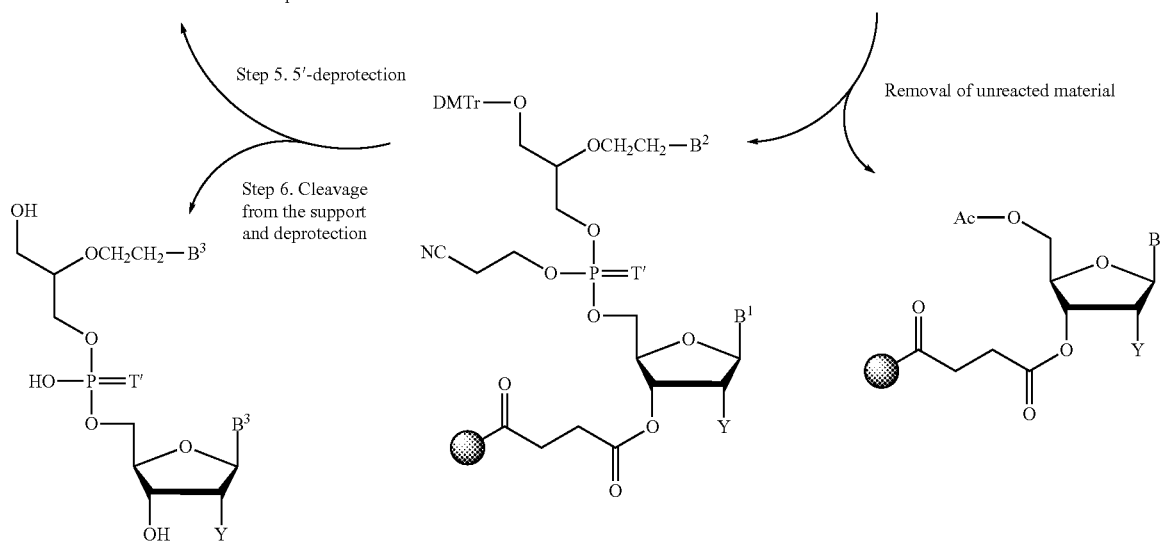

Next chain extension step
Step 5. 5'-deprotection
Step 6. Cleavage from the support and deprotection
Removal of unreacted material

 = Solid carrier (such as CPG)

wherein Y, $B^1$, $B^2$, $B^3$, T' and L are as defined above.

As illustrated in the example scheme 2, the 3'-terminal-solid carrier and the modified nucleic acid monomer compound (such as the modified nucleic acid monomer compound represented by formula (VI)) of formula (I) wherein $A^2$ is a phosphorus functional group (preferably —P(—$OR^7$)—$NRR^9$) as the chain extension raw material monomer are subjected to condensation reaction followed by oxidation or sulphurization step, thereby linking nucleoside subunits through a phosphodiester bond or a phosphorothioate bond. By repeating the chain extension step (steps 2 to 5 in the example scheme 1 above or steps 2 to 5 in the example scheme 2), an oligonucleotide block containing a plurality of nucleoside subunits linked together may be obtained. Production of the oligonucleotide block may be followed by cleavage from the support and deprotection reaction to obtain the oligonucleic acid analogue of the embodiment.

By using the modified nucleic acid monomer compound represented by formula (VI) as the chain extension raw material monomer in an arbitrary number of times among the repetition of the chain extension step, the oligonucleic acid analogue containing one or more arbitrary number of partial structures represented by formula (IX) at an arbitrary position other than the 3'-terminal may be obtained.

By using a solid phase synthesis carrier (universal support, e.g. Andrei P. Guzaev and Muthiah Manoharan, J. Amer. Chem. Soc., 2003, 125, 2380-2381) carrying a universal linker that does not require preparation of a special monomer for 3'-terminal introduction, the oligonucleic acid analogue containing one or more arbitrary number of partial structures represented by formula (IX) at an arbitrary position may be obtained from the modified nucleic acid monomer compound represented by formula (VI) as indicated below.

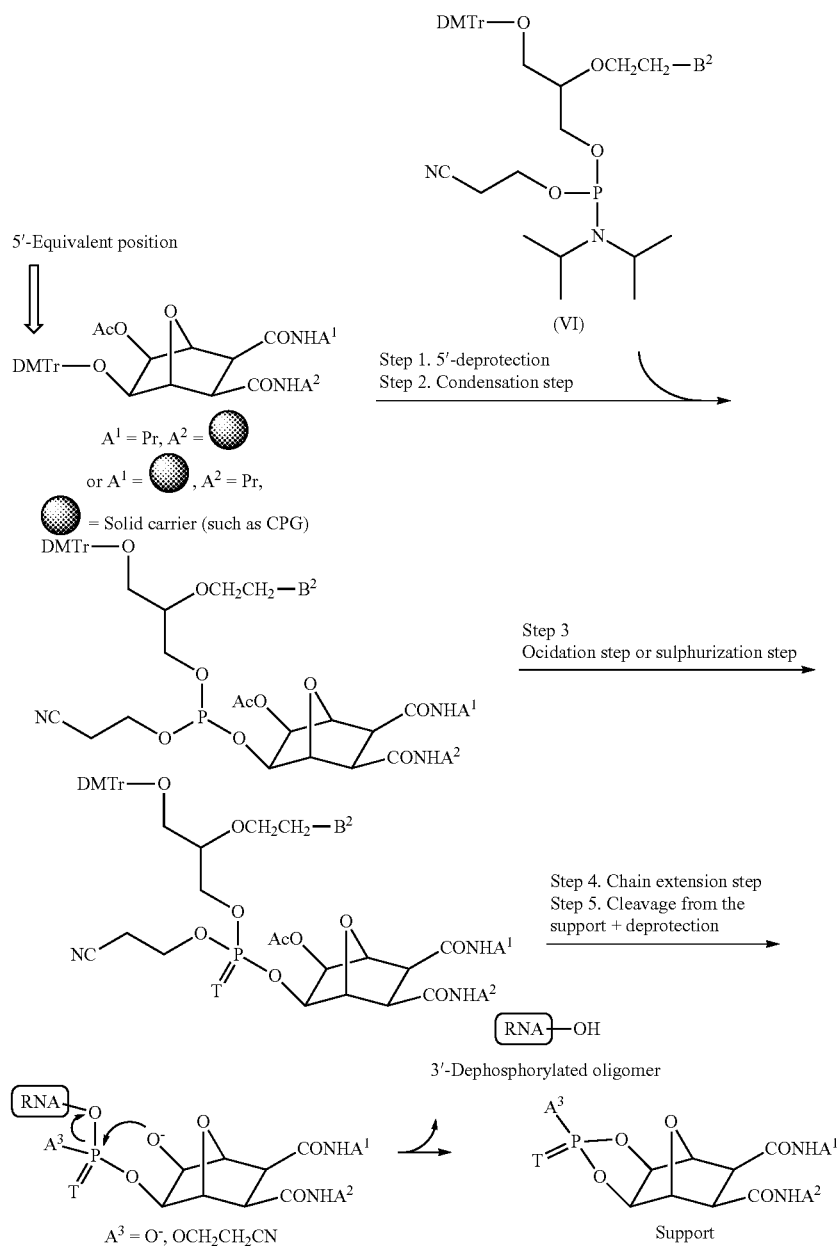

The oligonucleic acid analogue having a phosphorothioate bond may be prepared by performing the sulphurization step instead of oxidation step of a phosphorus atom. The sulphurization step may be sulphurization reaction that is generally used for synthesis of modified nucleic acid having a phosphorothioate bond. In sulphurization reaction, reagents such as, in addition to a suspension of sulphur in 2,6-lutidine, a solution of sulphur in carbon disulphide and Lawesson's reagent, Beaucage reagent (3H-1,2-benzodithiol-3-one 1,1-dioxide) (R. P. Iyer, W. Egan, J. B. Regan, and S. L. Beaucage, J. Amer. Chem. Soc., 1990, 112, 1253-1254), tetraethylthiuram disulphide (TETD) (H. Vu et al., Tetrahedron Lett., 32, 3005-3008 (1991), (3-((dimethylaminomethylidene)amino)-3H-1,2,4-dithiazole-3-thione) (DDTT) (M. Overhoff and G. Sczakiel, EMBO Rep, 2005, 6, 1176-81) may be used. Automated nucleic acid synthesisers are utilised in which in addition to an oxidizing agent of a phosphorus atom, a sulphurization reaction reagent is preliminarily provided so that a phosphorothioate bond may be introduced as an arbitrary position in the oligonucleic acid analogue.

In order to obtain a desired oligonucleic acid analogue or, for example, after production of oligonucleotide blocks, deprotection reaction may be performed. Deprotection reaction may be selected by referring to the reference by Greene et al. described above. The finally produced oligonucleic acid analogue may be treated with, for example, an alkaline aqueous solution such as concentrated aqueous ammonia and sodium hydroxide aqueous solution similar to the deprotection reaction, thereby cleaving the product from the solid carrier. For deprotection reaction and cleavage from the solid carrier, automated nucleic acid synthesisers are utilised.

As a method for constructing a phosphorodithioate structure represented by formula (XV), reference by Marshall et al. (Science 259: 1564-1570, 1993) or reference by Caruthers and Nielsen (WO 1989/011486) may be referred to.

By the above steps, one or two or more partial structures of formula (IX) may be incorporated in an arbitrary position in the oligonucleic acid analogue as a subunit (nucleobase unit).

The thus obtained single-stranded oligonucleic acid analogue may further be formed into a double-stranded oligonucleic acid analogue. Namely, for example, a single-stranded oligonucleic acid analogue having a complementary sequence to the obtained single-stranded oligonucleic acid analogue is produced. This additional single-stranded oligonucleic acid analogue may be a natural-type oligonucleotide or an oligonucleotide containing one or more partial structure of formula (IX) of the present invention or an oligonucleotide containing a building block of a nucleoside that contains a modified base moiety or sugar moiety. For example, by dissolving each of single-stranded oligonucleotide analogues in a common annealing buffer that is known to a person skilled in the art, mixing the same, subjecting the same to heat treatment and cooling, a double-stranded oligonucleic acid analogue may be produced.

The oligonucleic acid analogue containing the modified nucleic acid monomer compound of the present invention as at least one building block has excellent biological stability (such as stability in blood, more specifically the residual amount of the oligonucleic acid analogue in the serum) and/or target gene silencing activity. Therefore, when the oligonucleic acid analogue is used as, for example, siRNA, it is expected to show the value as a "medicament treating a disease by inhibiting an action of a gene" typically including antitumor agent and antiviral agent. The oligonucleic acid analogue containing the modified nucleic acid monomer compound of the present invention as at least one building block may be mixed with a conventional auxiliary agent such as a buffering agent and/or a stabiliser to make a parenteral administration preparation such as an injection. The oligonucleic acid analogue may be encapsulated in a liposome made of lipid or coated by a functional polymer film to prepare a preparation having increased stability in blood.

EXAMPLES

The present invention is hereinafter more specifically described by way of Examples and Reference Examples which do not limit the present invention. The abbreviations used hereinbelow are conventional and well-known to a person skilled in the art, some of which are indicated hereinbelow.

Bz: Benzoyl
CPG: Controlled pore glass
DIPEA: N,N-diisopropylethylamine
DIAD: Diisopropyl azodicarboxylate
DMAP: 4-(Dimethylamino)pyridine
DMF: N,N-dimethylformamide
DMTr: 4,4'-Dimethoxytrityl
DSPC: 1,2-Distearoyl-sn-glycero-3-phosphocholine
EDC: 1-Ethyl-3-(3-dimethylaminopropyl)carbodiimide hydrochloride
Et: Ethyl
HBTU: O-(benzotriazol-1-yl)-N,N,N',N'-tetramethyluronium hexafluorophosphate
LCAA: Long chain alkylamine
n-: Normal
NMO: N-methylmorpholine N-oxide
$NaBH_4$: Sodium borohydride
Ph: Phenyl
Pr: Propyl
iPr: Isopropyl
tert-: Tertiary
TBAF: Tetra-n-butylammonium fluoride
TEA: Triethylamine
TFA: Trifluoroacetic acid
THF: Tetrahydrofuran
TBDPS: Tert-butyldiphenylsilyl
$^1$H-NMR: Proton nuclear magnetic resonance spectrometry The chemical shifts and the coupling constants of proton nuclear magnetic resonance ($^1$H-NMR) spectra are recorded in δ unit (ppm) relative to tetramethylsilane and hertz (Hz), respectively. The patterns mean the following: s: singlet, d: doublet, br: broad and m: multiplet.

$^1$H-NMR was determined on Varian/Agilent Mercury 400 MHz system (400 MHz).

For chromatography, Parallel Prep manufactured by YAMAZEN {column:

manufactured by YAMAZEN, Hi-Flash™ Column (Silica gel), size: S (16×60 mm), M (20×75 mm), L (26×100 mm), 2 L (26×150 mm)} or silica gel manufactured by Merck (Silica gel 60, 70-230 mesh) or silica gel manufactured by Fuji Silysia Chemical Ltd. (BW-Silica gel, 200-400 mesh) was used.

Separation by supercritical fluid chromatography (SFC) was performed using Prep 100q manufactured by Waters.

For synthesis of solid carriers used for siRNA synthesis, amino LCAA CPG support 1000 Å manufactured by ChemGenes (loading amount: 103 µmol/g) was used.

In Examples below, "room temperature" generally represents approximately 10° C. to approximately 35° C. % represents percent by weight unless otherwise specified.

In the names of compounds described herein, (±)- and (RS)- indicates a racemic substance, and (+)-, (−)-, (R)- and (S)- indicate (+), (−), (R)- and (S)-enantiomer, respectively. The symbol "*" in a configuration represents the relative configuration and represents any one of the enantiomers unless otherwise specified.

Example 1

Synthesis of (R)-2-[2-(3-benzoyl-5-methyl-2,4-dioxo-3,4-dihydropyrimidin-1 (2H)-yl)ethoxy]-3-[bis (4-methoxyphenyl)(phenyl)methoxy]propyl(2-cyanoethyl)diisopropylphosphoramidite

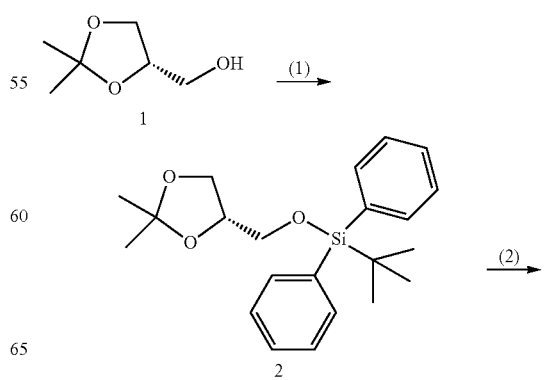

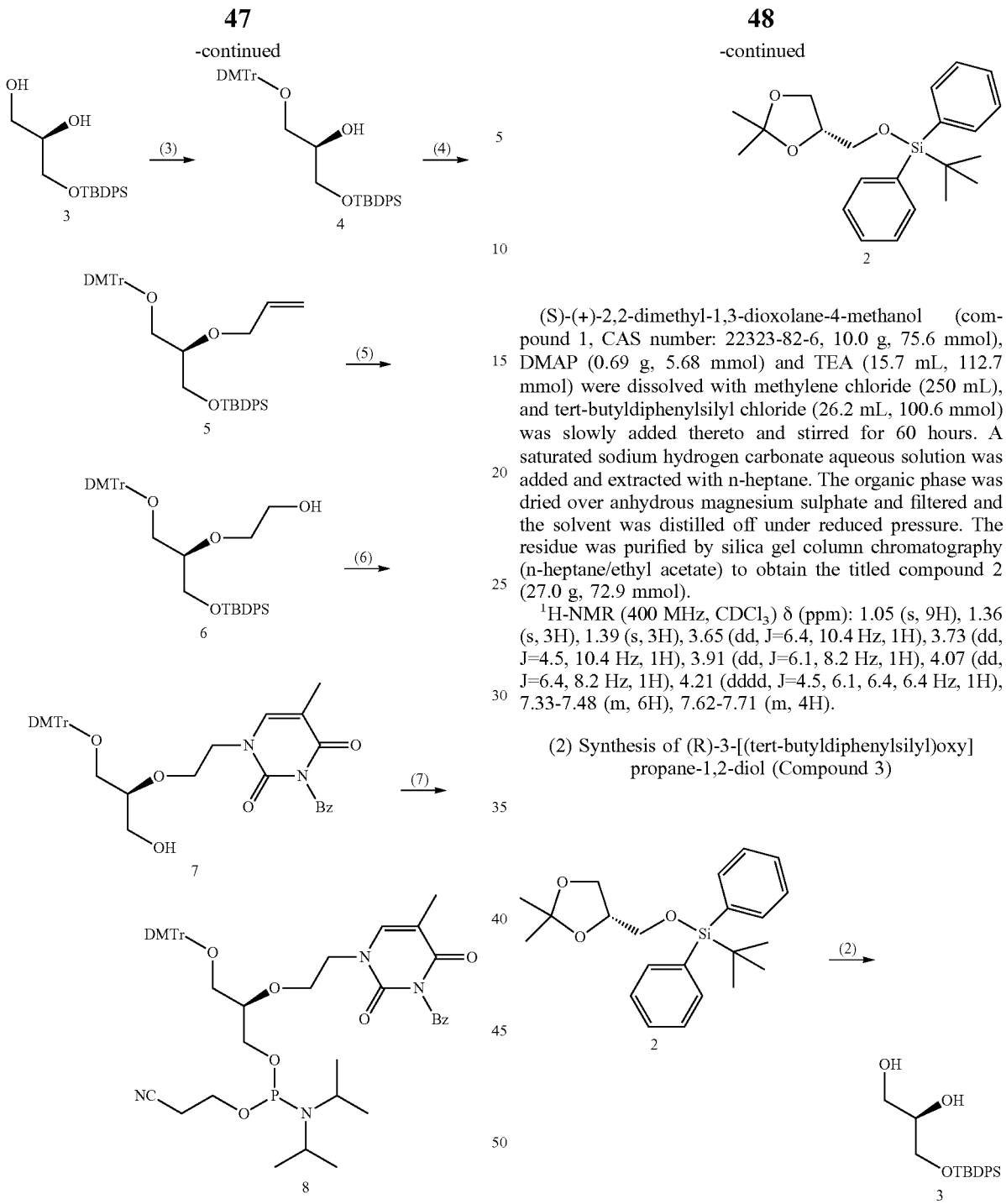

(1) Synthesis of (R)-tert-butyl[(2,2-dimethyl-1,3-dioxolan-4-yl)methoxy]diphenylsilane (Compound 2)

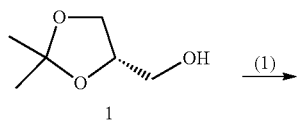

(S)-(+)-2,2-dimethyl-1,3-dioxolane-4-methanol (compound 1, CAS number: 22323-82-6, 10.0 g, 75.6 mmol), DMAP (0.69 g, 5.68 mmol) and TEA (15.7 mL, 112.7 mmol) were dissolved with methylene chloride (250 mL), and tert-butyldiphenylsilyl chloride (26.2 mL, 100.6 mmol) was slowly added thereto and stirred for 60 hours. A saturated sodium hydrogen carbonate aqueous solution was added and extracted with n-heptane. The organic phase was dried over anhydrous magnesium sulphate and filtered and the solvent was distilled off under reduced pressure. The residue was purified by silica gel column chromatography (n-heptane/ethyl acetate) to obtain the titled compound 2 (27.0 g, 72.9 mmol).

$^1$H-NMR (400 MHz, CDCl$_3$) δ (ppm): 1.05 (s, 9H), 1.36 (s, 3H), 1.39 (s, 3H), 3.65 (dd, J=6.4, 10.4 Hz, 1H), 3.73 (dd, J=4.5, 10.4 Hz, 1H), 3.91 (dd, J=6.1, 8.2 Hz, 1H), 4.07 (dd, J=6.4, 8.2 Hz, 1H), 4.21 (dddd, J=4.5, 6.1, 6.4, 6.4 Hz, 1H), 7.33-7.48 (m, 6H), 7.62-7.71 (m, 4H).

(2) Synthesis of (R)-3-[(tert-butyldiphenylsilyl)oxy]propane-1,2-diol (Compound 3)

The compound 2 (27.0 g, 72.9 mmol) obtained in Example 1-(1) and methylene chloride (260 mL) were dissolved with MeOH (60 mL), a mixed solution of concentrated hydrochloric acid (12 mL) and MeOH (200 mL) was added thereto at room temperature and stirred at room temperature for 30 minutes. The reaction mixture was cooled in an ice bath, a 5 N sodium hydroxide aqueous solution was added thereto to make the pH neutral and then alkaline with a small amount of saturated sodium hydrogen carbonate aqueous solution, and the solvent was distilled off under reduced pressure. To the obtained residue was added water and the mixture was extracted with ethyl acetate. The organic phase was washed with a saturated sodium chloride solution and dried over anhydrous magnesium sulphate. After filtration, the solvent was distilled off under reduced pressure. The residue was purified by silica gel column chromatography (n-heptane/ethyl acetate) to obtain the titled compound 3 (17.6 g, 53.3 mmol).

$^1$H-NMR (400 MHz, CDCl$_3$) δ (ppm): 1.07 (s, 9H), 1.99 (dd, J=5.3, 7.0 Hz, 1H), 2.59 (d, J=5.3 Hz, 1H), 3.57-3.90 (m, 5H), 7.35-7.49 (m, 6H), 7.62-7.70 (m, 4H).

(3) Synthesis of (R)-1-[bis(4-methoxyphenyl)(phenyl)methoxy]-3-[(tert-butyldiphenylsilyl)oxy]propan-2-ol (Compound 4)

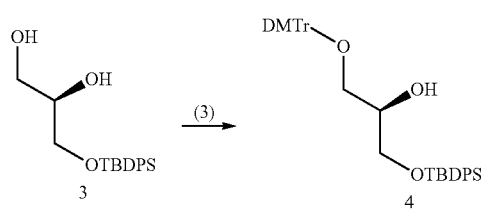

The compound 3 (9.0 g, 27.2 mmol) obtained in Example 1-(2) was dissolved with pyridine (225 mL), and DMAP (0.23 g, 1.9 mmol) and 4,4'-dimethoxytrityl chloride (11.1 g, 32.8 mmol) were added thereto under ice cooling and stirred at room temperature for 36 hours. The reaction mixture was concentrated under reduced pressure, and the obtained residue was dissolved with methylene chloride (150 mL) and washed with a saturated sodium hydrogen carbonate aqueous solution and a saturated sodium chloride solution in this order. The organic phase was dried over anhydrous sodium sulphate and filtered and the solvent was distilled off under reduced pressure. The residue was purified by silica gel column chromatography (n-heptane/ethyl acetate/0.5% TEA) to obtain the titled compound 4 (14.3 g, 22.6 mmol).

$^1$H-NMR (400 MHz, CDCl$_3$) δ (ppm): 0.99 (s, 9H), 2.44 (d, J=5.5 Hz, 1H), 3.13-3.33 (m, 2H), 3.70-3.81 (m, 2H), 3.78 (s, 6H), 3.83-3.93 (m, 1H), 6.74-6.85 (m, 4H), 7.09-7.49 (m, 15H), 7.56-7.67 (m, 4H).

(4) Synthesis of (R)-{2-(allyloxy)-3-[bis(4-methoxyphenyl)(phenyl)methoxy]propoxy}(tert-butyl)diphenylsilane (Compound 5)

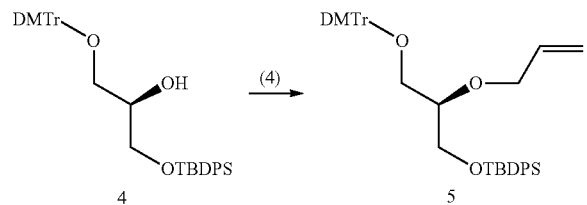

The compound 4 (11.6 g, 18.3 mmol) obtained in Example 1-(3) was dissolved with THF (90 mL), and 60% sodium hydride (2.2 g, 55.0 mmol) was slowly added thereto while cooling in a water bath and stirred at room temperature for 10 minutes. While cooling in a water bath, allyl bromide (7.8 mL, 91.6 mmol) was added. After stirring at room temperature for 1.5 hours, 60% sodium hydride (1.5 g, 36.7 mmol) and allyl bromide (7.8 mL, 91.6 mmol) were further added. After 1 hour and 2 hours, allyl bromide (7.8 mL, 91.6 mmol) was further added twice. The reaction mixture was cooled in an ice bath to which water was added and extracted with ethyl acetate. The organic phase was washed with a saturated sodium chloride solution and dried over anhydrous magnesium sulphate. After filtration, the solvent was distilled off under reduced pressure. The residue was purified by silica gel column chromatography (n-heptane/ethyl acetate/0.5% TEA) to obtain the titled compound 5 (9.7 g, 14.4 mmol).

$^1$H-NMR (400 MHz, CDCl$_3$) δ (ppm): 0.96 (s, 9H), 3.15-3.28 (m, 2H), 3.59-3.67 (m, 1H), 3.69-3.77 (m, 2H), 3.77 (s, 6H), 4.06-4.18 (m, 2H), 5.10-5.18 (m, 1H), 5.22-5.31 (m, 1H), 5.84-5.97 (m, 1H), 6.73-6.84 (m, 4H), 7.13-7.49 (m, 15H), 7.56-7.67 (m, 4H).

(5) Synthesis of (R)-2-({1-[bis(4-methoxyphenyl)(phenyl)methoxy]-3-[(tert-butyldiphenylsilyl)oxy]propan-2-yl}oxy)ethanol (Compound 6)

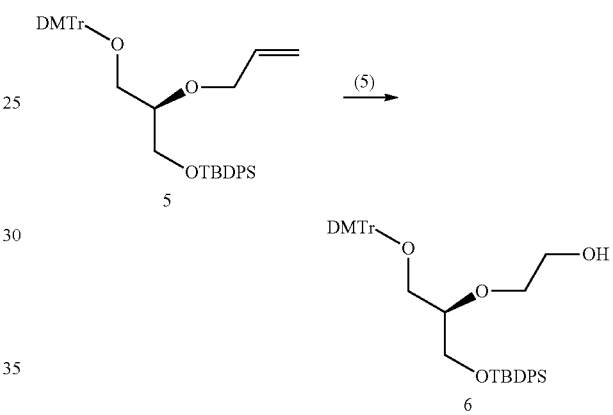

The compound 5 (9.0 g, 13.4 mmol) obtained in Example 1-(4) and NMO (2.4 g, 20.6 mmol) were dissolved with THF (45 mL), tert-butanol (15 mL) and water (7.5 mL), and a 2.5% osmium tetroxide/tert-butanol solution (1.8 mL, 0.144 mmol) was added thereto under ice cooling and stirred at room temperature for 18 hours. To the reaction solution, a 5% sodium hydrogen sulphite aqueous solution (20 mL) was added and stirred for 10 minutes. Methylene chloride (90 mL) and water (90 mL) were added thereto and the mixture was separated and then extracted twice with methylene chloride. The organic phase was dried over anhydrous sodium sulphate and filtered and the solvent was distilled off under reduced pressure.

The obtained residue was dissolved with THF (45 mL), and lead tetraacetate (6.2 g, 13.4 mmol) was gradually added thereto so that the inner temperature was 10° C. or lower, and stirred for 20 minutes under ice cooling and for 40 minutes at room temperature. Insoluble materials were separated by filtration and washed with THF (27 mL).

To the filtrate, a solution containing NaBH$_4$ (0.94 g, 24.9 mmol) dissolved with 1 N sodium hydroxide (45 mL) was added under ice cooling so that the inner temperature was 10° C. or lower, and stirred for 15 minutes under ice cooling and for 2 hours at room temperature. To the reaction solution, a saturated ammonium chloride aqueous solution was added to pH=8 and stirred for 5 minutes. Ethyl acetate (54 mL) was added and then separation and extraction with ethyl acetate was performed once. The organic phase was washed with a mixed solution of a 0.5 N sodium hydroxide aqueous solution (45 mL) and a saturated sodium chloride solution (36 mL) and then washed again with a saturated sodium chloride solution. The organic layer was dried over anhydrous magnesium sulphate and filtered and the solvent was distilled off under reduced pressure. The residue was purified by silica gel column chromatography (n-heptane/ethyl acetate/0.5% TEA) to obtain the titled compound 6 (7.6 g, 11.2 mmol).

$^1$H-NMR (400 MHz, CDCl$_3$) δ (ppm): 0.99 (s, 9H), 2.59-2.74 (m, 1H), 3.10-3.25 (m, 2H), 3.60-3.76 (m, 6H), 3.78 (s, 6H), 6.74-6.85 (m, 4H), 7.14-7.49 (m, 15H), 7.56-7.68 (m, 4H).

(6) Synthesis of (S)-3-benzoyl-1-[2-({1-[bis(4-methoxyphenyl)(phenyl)methoxy]-3-hydroxypropan-2-yl}oxy) ethyl]-5-methylpyrimidine-2,4(1H, 3H)-dione (Compound 7)

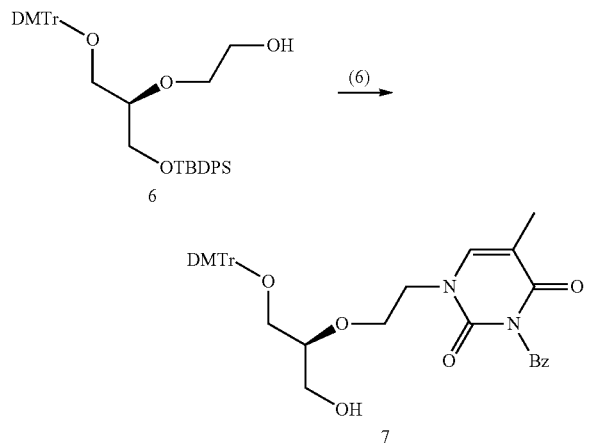

The compound 6 (1.0 g, 1.48 mmol) obtained in Example 1-(5), 3-benzoylthymine (0.68 g, 3.0 mmol) and triphenylphosphine (0.97 g, 3.70 mmol) were suspended in THF (15 mL), and DIAD (0.73 mL, 3.69 mmol) was added dropwise thereto under ice cooling and stirred under a nitrogen atmosphere at room temperature for 19 hours. The reaction solution was concentrated under reduced pressure, and the obtained residue was purified by column chromatography (n-heptane/ethyl acetate/0.5% TEA) to obtain a 3-benzoylthymine substituted substance (1.28 g).

The obtained crude substituted substance was dissolved with THF (1.4 mL), and a 1 M TBAF/THF solution (6.5 mL, 6.5 mmol) was added thereto under ice cooling and stirred at the same temperature for 2.5 hours. To the reaction mixture was added water and the mixture was extracted with ethyl acetate. The organic phase was washed with a mixed solution (1:1) of a saturated sodium hydrogen carbonate aqueous solution and a saturated sodium chloride solution and dried over anhydrous magnesium sulphate. After filtration, the solvent was distilled off under reduced pressure. The residue was purified by silica gel column chromatography (n-heptane/ethyl acetate/0.5% TEA) to obtain the titled compound 7 (772 mg, 1.19 mmol).

$^1$H-NMR (400 MHz, CDCl$_3$) δ (ppm): 1.86 (s, 3H), 1.95-2.03 (m, 1H), 3.18-3.28 (m, 2H), 3.47-3.92 (m, 6H), 3.78 (s, 6H), 3.94-4.06 (m, 1H), 6.79-6.86 (m, 4H), 7.18-7.34 (m, 9H), 7.36-7.47 (m, 3H), 7.55-7.65 (m, 1H), 7.83-7.94 (m, 2H).

(7) Synthesis of (R)-2-[2-(3-benzoyl-5-methyl-2,4-dioxo-3,4-dihydropyrimidin-1 (2H)-yl)ethoxy]-3-[bis(4-methoxyphenyl)(phenyl)methoxy]propyl(2-cyanoethyl)diisopropylphosphoramidite (Compound 8)

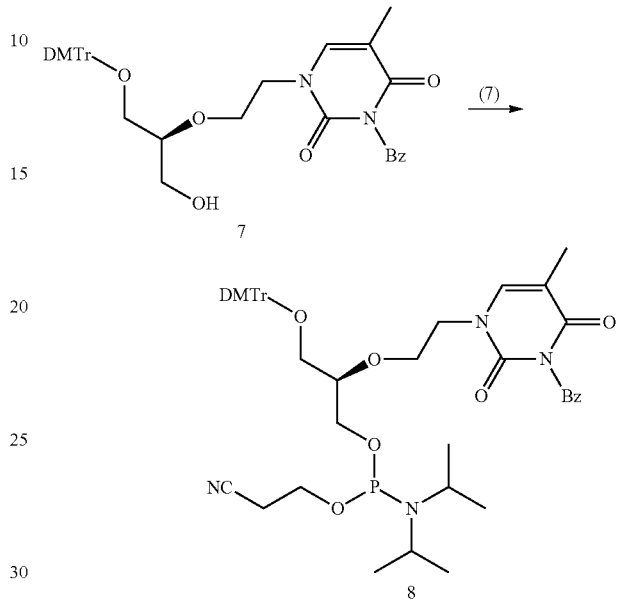

The compound 7 (294 mg, 0.45 mmol) obtained in Example 1-(6) and DIPEA (0.39 mL, 2.3 mmol) were dissolved with methylene chloride (4.6 mL), and 2-cyanoethyl N,N-diisopropylchlorophosphoramidite (0.25 mL, 1.1 mmol) was added thereto under ice cooling and stirred at room temperature for 3 hours. To the reaction solution was added a saturated sodium hydrogen carbonate aqueous solution and the mixture was extracted with ethyl acetate. The organic phase was dried over anhydrous magnesium sulphate and filtered and the solvent was distilled off under reduced pressure. The residue was purified by silica gel column chromatography (n-heptane/ethyl acetate/0.5% Et$_3$N) to obtain the titled compound 8 (200 mg, 0.235 mmol).

$^1$H-NMR (400 MHz, CDCl$_3$) δ (ppm): 1.07-1.21 (m, 12H), 1.78-1.84 (m, 3H), 2.48-2.62 (m, 2H), 3.13-3.27 (m, 2H), 3.43-4.01 (m, 11H), 3.77 (s, 6H), 6.77-6.86 (m, 4H), 7.16-7.34 (m, 8H), 7.35-7.46 (m, 4H), 7.54-7.64 (m, 1H), 7.83-7.92 (m, 2H).

Example 2

Synthesis of (S)-2-[2-(3-benzoyl-5-methyl-2,4-dioxo-3,4-dihydropyrimidin-1 (2H)-yl)ethoxy]-3-[bis(4-methoxyphenyl)(phenyl)methoxy]propyl(2-cyanoethyl)diisopropylphosphoramidite

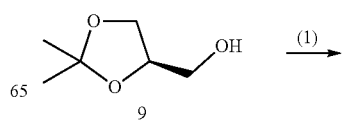

53
-continued

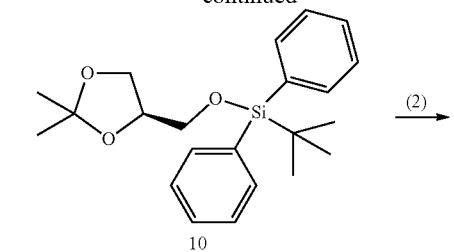

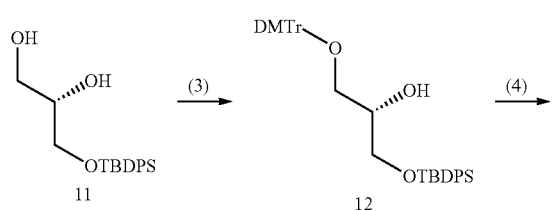

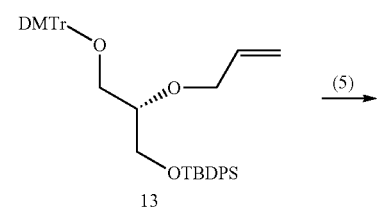

54

(1) Synthesis of (S)-tert-butyl[(2,2-dimethyl-1,3-dioxolan-4-yl)methoxy]diphenylsilane (Compound 10)

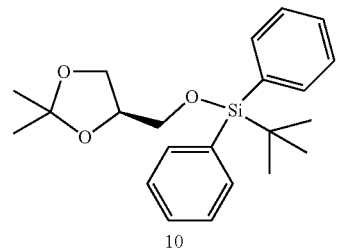

(R)-(−)-2,2-dimethyl-1,3-dioxolane-4-methanol (compound 9, CAS number: 14347-78-5, 1.0 g, 7.56 mmol) and imidazole (1.08 g, 15.9 mmol) were dissolved with DMF (7.6 mL), tert-butyldiphenylsilyl chloride (2.1 mL, 7.95 mmol) was slowly added thereto at 0° C. and stirred at room temperature for 16 hours. Tert-butyl methyl ether (15 mL) and water (15 mL) were added and separated. The organic phase was washed with a saturated sodium chloride solution and dried over anhydrous magnesium sulphate. After filtration, the solvent was distilled off under reduced pressure to obtain a crude product (2.8 g) of the titled compound 10.

(2) Synthesis of (S)-3-[(tert-butyldiphenylsilyl)oxy]propane-1,2-diol (Compound 11)

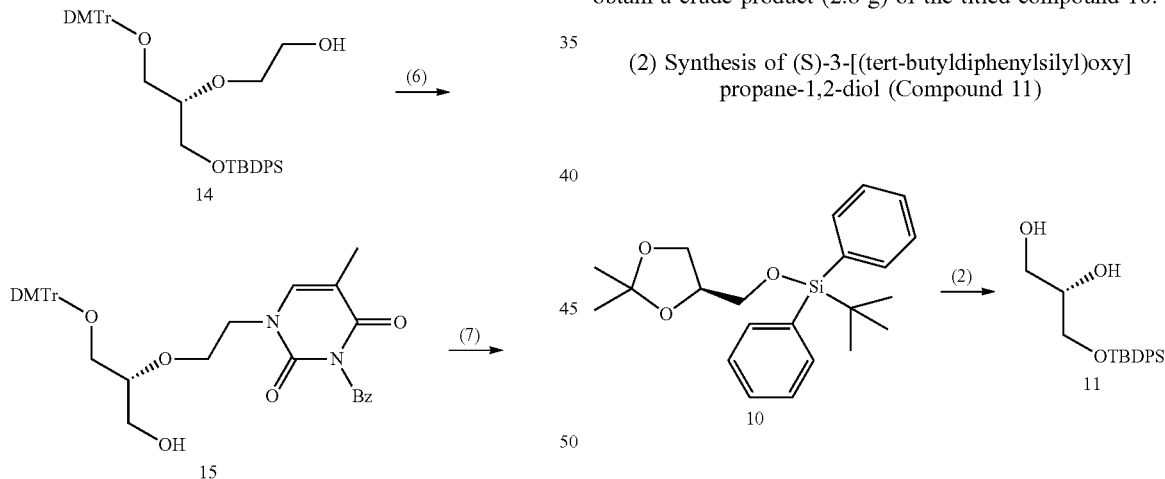

The crude product (2.8 g) of the compound 10 obtained in Example 2-(1) was dissolved with methylene chloride (28 mL) and MeOH (14 mL), and concentrated hydrochloric acid (1.3 mL, 15.1 mmol) was added thereto at room temperature and stirred for 30 minutes. The reaction mixture was cooled in an ice bath, a 5 N sodium hydroxide aqueous solution was added thereto to make the pH neutral and then alkaline with a small amount of saturated sodium hydrogen carbonate aqueous solution, and the solvent was distilled off under reduced pressure. To the obtained residue was added water and the mixture was extracted with ethyl acetate. The organic phase was washed with a saturated sodium chloride solution and dried over anhydrous magnesium sulphate. After filtration, the solvent was distilled off under reduced pressure to obtain a crude product (2.48 g) of the titled compound 11.

(3) Synthesis of (S)-1-[bis(4-methoxyphenyl)(phenyl)methoxy]-3-[(tert-butyldiphenylsilyl)oxy]propan-2-ol (Compound 12)

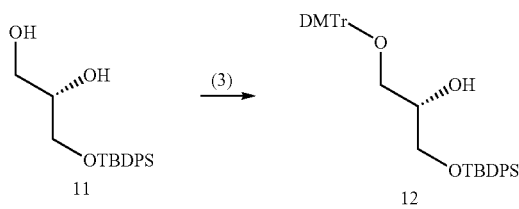

The crude product (2.48 g) of the compound 11 obtained in Example 2-(2) was dissolved with pyridine (30 mL), and 4,4'-dimethoxytrityl chloride (2.1 g, 6.05 mmol) was added thereto under ice cooling and stirred at room temperature for 1 hour. 4,4'-dimethoxytrityl chloride (0.13 g, 0.38 mmol) was further added and stirred at room temperature for 1 hour. The reaction mixture was concentrated under reduced pressure, and the obtained residue was suspended in tert-butyl methyl ether and filtered to remove insoluble materials. The filtrate was washed with a saturated sodium hydrogen carbonate aqueous solution and a saturated sodium chloride solution in this order. The organic phase was dried over anhydrous sodium sulphate and filtered and the solvent was distilled off under reduced pressure. The residue was purified by silica gel column chromatography (n-heptane/ethyl acetate/0.5% TEA) to obtain the titled compound 12 (2.68 g, 4.23 mmol).

$^1$H-NMR (400 MHz, CDCl$_3$) δ (ppm): 0.99 (s, 9H), 2.44 (d, J=5.5 Hz, 1H), 3.13-3.33 (m, 2H), 3.70-3.81 (m, 2H), 3.78 (s, 6H), 3.83-3.93 (m, 1H), 6.74-6.85 (m, 4H), 7.09-7.49 (m, 15H), 7.56-7.67 (m, 4H).

(4) Synthesis of (S)-{2-(allyloxy)-3-[bis(4-methoxyphenyl)(phenyl)methoxy]propoxy}(tert-butyl)diphenylsilane (Compound 13)

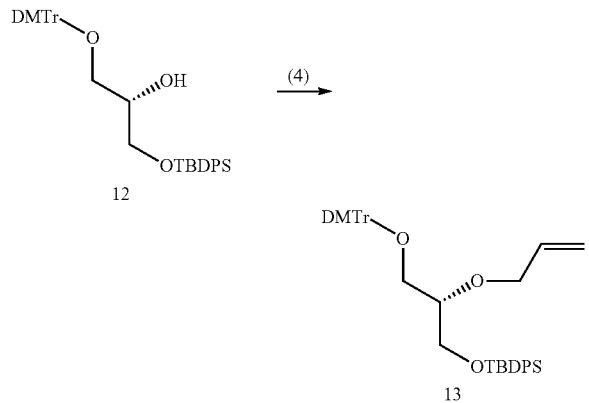

The compound 12 (1.0 g, 1.58 mmol) obtained in Example 2-(3) was dissolved with THF (2.3 mL), and 60% sodium hydride (0.11 g, 2.84 mmol) was slowly added thereto while cooling in a water bath and stirred at room temperature for 45 minutes. While cooling in a water bath, allyl bromide (0.15 mL, 1.82 mmol) was added thereto. After stirring at room temperature for 2 hours, 60% sodium hydride (0.24 g, 6.20 mmol) and allyl bromide (0.45 mL, 5.45 mmol) were further added and stirred for 2 hours. The reaction mixture was cooled in an ice bath to which water was added and extracted with ethyl acetate. The organic phase was washed with a saturated sodium chloride solution and dried over anhydrous magnesium sulphate. After filtration, the solvent was distilled off under reduced pressure. The residue was purified by silica gel column chromatography (n-heptane/ethyl acetate/0.5% TEA) to obtain the titled compound 13 (0.73 g, 1.09 mmol).

$^1$H-NMR (400 MHz, CDCl$_3$) δ (ppm): 0.96 (s, 9H), 3.15-3.28 (m, 2H), 3.59-3.67 (m, 1H), 3.69-3.77 (m, 2H), 3.77 (s, 6H), 4.06-4.18 (m, 2H), 5.10-5.18 (m, 1H), 5.22-5.31 (m, 1H), 5.84-5.97 (m, 1H), 6.73-6.84 (m, 4H), 7.13-7.49 (m, 15H), 7.56-7.67 (m, 4H).

(5) Synthesis of (S)-2-({1-[bis(4-methoxyphenyl)(phenyl)methoxy]-3-[(tert-butyldiphenylsilyl)oxy]propan-2-yl}oxy)ethanol (Compound 14)

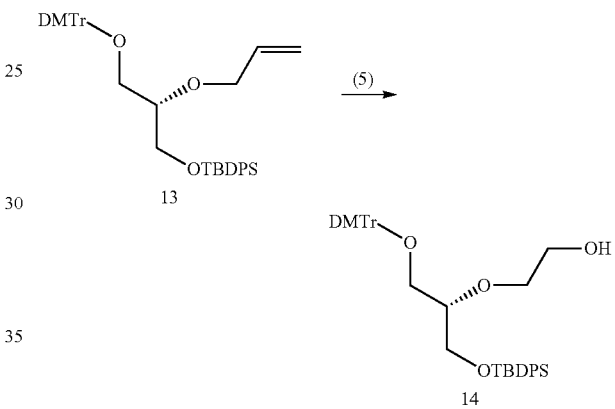

The compound 13 (0.53 g, 0.788 mmol) obtained in Example 2-(4) and NMO (0.14 g, 1.21 mmol) were dissolved with THF (2.6 mL), tert-butanol (0.90 mL) and water (0.45 mL), and a 2.5% osmium tetroxide/tert-butanol solution (0.10 mL, 7.8 μmol) was added thereto under ice cooling and stirred at room temperature for 18 hours. To the reaction solution, a 5% sodium hydrogen sulphite aqueous solution (2.6 mL) was added and stirred for 30 minutes, and water was added and then extracted three times with methylene chloride. The organic phase was dried over anhydrous sodium sulphate and filtered and the solvent was distilled off under reduced pressure.

The obtained residue was dissolved with THF (2.6 mL), and lead tetraacetate (0.39 g, 0.788 mmol) was gradually added thereto under ice cooling so that the inner temperature was 10° C. or lower, and stirred for 20 minutes under ice cooling and for 30 minutes at room temperature. The reaction solution was filtered to remove insoluble materials and washed with THF.

To the filtrate, a solution containing NaBH$_4$ (55 mg, 1.47 mmol) dissolved with 1 N sodium hydroxide (2.6 mL) was added under ice cooling so that the inner temperature was 10° C. or lower, and stirred for 20 minutes under ice cooling and for 1 hour at room temperature. To the reaction solution, a saturated ammonium chloride aqueous solution was added to pH=8 and stirred for 5 minutes. Ethyl acetate was added and separated and the water layer was extracted once with ethyl acetate. The organic phase was washed with a 1 N sodium hydroxide aqueous solution and a saturated sodium chloride solution and then dried over anhydrous magnesium sulphate. After filtration, the solvent was distilled off under reduced pressure. The residue was purified by silica gel column chromatography (n-heptane/ethyl acetate/0.5% TEA) to obtain the titled compound 14 (0.43 g, 0.635 mmol).

$^1$H-NMR (400 MHz, CDCl$_3$) δ (ppm): 0.99 (s, 9H), 2.59-2.74 (m, 1H), 3.10-3.25 (m, 2H), 3.60-3.76 (m, 6H), 3.78 (s, 6H), 6.74-6.85 (m, 4H), 7.14-7.49 (m, 15H), 7.56-7.68 (m, 4H).

(6) Synthesis of (R)-3-benzoyl-1-[2-({1-[bis(4-methoxyphenyl)(phenyl)methoxy]-3-hydroxypropan-2-yl}oxy) ethyl]-5-methylpyrimidine-2,4(1H, 3H)-dione (Compound 15)

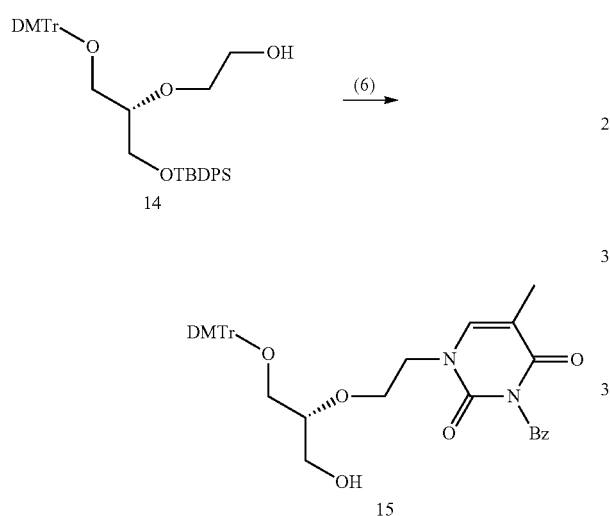

The compound 14 (430 mg, 0.635 mmol) obtained in Example 2-(5), 3-benzoylthymine (263 mg, 1.14 mmol) and triphenylphosphine (417 mg, 1.59 mmol) were suspended in THF (6.4 mL), and DIAD (0.31 mL, 1.59 mmol) was added dropwise thereto under ice cooling and stirred under a nitrogen atmosphere at room temperature for 19 hours. The reaction solution was concentrated under reduced pressure, and the obtained residue was purified by column chromatography (n-heptane/ethyl acetate/0.5% TEA) to obtain a 3-benzoylthymine substituted substance (830 mg).

The obtained crude substituted substance was dissolved with THF (1.7 mL), and a 1 M TBAF/THF solution (2.5 mL, 2.54 mmol) was added thereto under ice cooling and stirred for 20 minutes under ice cooling and for 1.5 hour at room temperature. The reaction solution was concentrated under reduced pressure, and the residue was purified by silica gel column chromatography (n-heptane/ethyl acetate/0.5% TEA) to obtain the titled compound 15 (206 mg, 0.320 mmol).

$^1$H-NMR (400 MHz, CDCl$_3$) δ (ppm): 1.86 (s, 3H), 1.95-2.03 (m, 1H), 3.18-3.28 (m, 2H), 3.47-3.92 (m, 6H), 3.78 (s, 6H), 3.94-4.06 (m, 1H), 6.79-6.86 (m, 4H), 7.18-7.34 (m, 9H), 7.36-7.47 (m, 3H), 7.55-7.65 (m, 1H), 7.83-7.94 (m, 2H).

(7) Synthesis of (S)-2-[2-(3-benzoyl-5-methyl-2,4-dioxo-3,4-dihydropyrimidin-1 (2H)-yl)ethoxy]-3-[bis(4-methoxyphenyl)(phenyl)methoxy]propyl(2-cyanoethyl)diisopropylphosphoramidite (Compound 16)

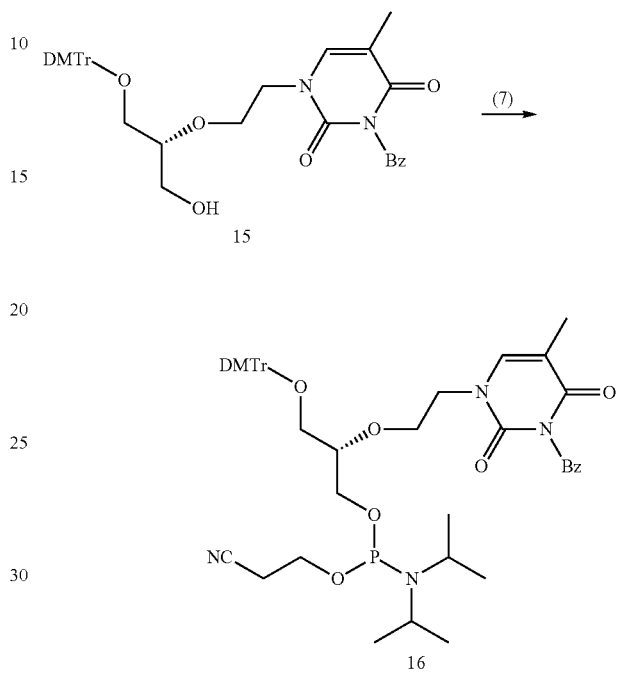

According to the method in Example 1-(7), the titled compound 16 (162 mg, 0.19 mmol) was obtained from the compound 15 (205 mg, 0.315 mmol) obtained in Example 2-(6), DIPEA (0.27 mL, 1.58 mmol), 2-cyanoethyl N,N-diisopropylchlorophosphoramidite (0.14 mL, 0.506 mmol) and methylene chloride (2.0 mL).

$^1$H-NMR (400 MHz, CDCl$_3$) δ (ppm): 1.07-1.21 (m, 12H), 1.78-1.84 (m, 3H), 2.48-2.62 (m, 2H), 3.13-3.27 (m, 2H), 3.43-4.01 (m, 11H), 3.77 (s, 6H), 6.77-6.86 (m, 4H), 7.16-7.34 (m, 8H), 7.35-7.46 (m, 4H), 7.54-7.64 (m, 1H), 7.83-7.92 (m, 2H).

Example 3

Synthesis of (R)-2-[2-(3-benzoyl-5-methyl-2,4-dioxo-3,4-dihydropyrimidin-1 (2H)-yl)ethoxy]-3-[bis(4-methoxyphenyl)(phenyl)methoxy]propyl(2-cyanoethyl)diisopropylphosphoramidite

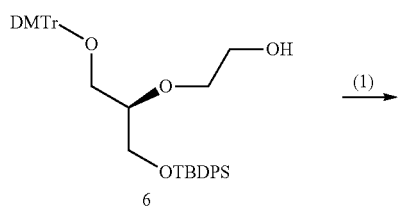

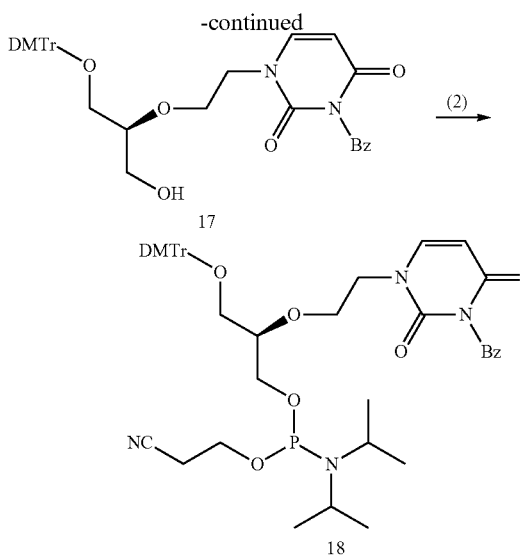

(1) Synthesis of (S)-3-benzoyl-1-[2-({1-[bis(4-methoxyphenyl)(phenyl)methoxy]-3-hydroxypropan-2-yl}oxy) ethyl]pyrimidine-2,4(1H,3H)-dione (Compound 17)

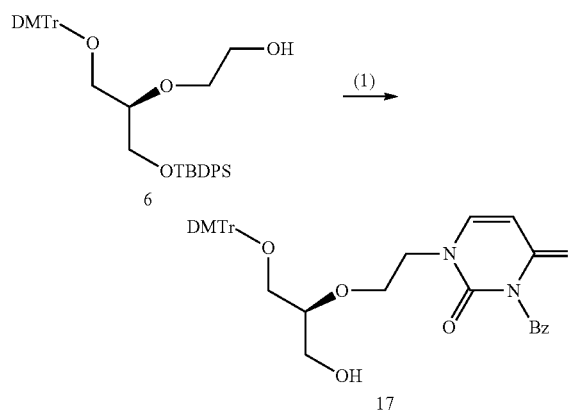

The compound 6 (1.77 g, 2.62 mmol) obtained in Example 1-(5), 3-benzoyluracil (1.13 g, 5.23 mmol) and triphenylphosphine (1.72 g, 6.54 mmol) were suspended in THF (26 mL), and DIAD (1.3 mL, 6.54 mmol) was added dropwise thereto under ice cooling and stirred under a nitrogen atmosphere at room temperature for 19 hours. The reaction solution was concentrated under reduced pressure and the obtained residue was purified by column chromatography (n-heptane/ethyl acetate/0.5% TEA) to obtain a 3-benzoyluracil substituted substance (3.7 g).

The obtained crude substituted substance was dissolved with THF (2.6 mL), and a 1 M TBAF/THF solution (13.1 mL, 13.1 mmol) was added thereto under ice cooling and stirred under ice cooling for 2.5 hours. To the reaction mixture was added water and the mixture was extracted with ethyl acetate. The organic phase was washed with a mixed solution (1:1) of a saturated sodium hydrogen carbonate aqueous solution and a saturated sodium chloride solution and dried over anhydrous magnesium sulphate. After filtration, the solvent was distilled off under reduced pressure. The residue was purified by silica gel column chromatography (n-heptane/ethyl acetate/0.5% TEA) to obtain the titled compound 17 (1.40 g, 2.20 mmol).

$^1$H-NMR (400 MHz, CDCl$_3$) δ (ppm): 1.89-2.03 (m, 1H), 3.15-3.33 (m, 2H), 3.48-3.58 (m, 1H), 3.58-3.93 (m, 5H), 3.78 (s, 6H), 3.94-4.06 (m, 1H), 5.69 (d, J=7.8 Hz, 1H), 6.77-6.89 (m, 4H), 7.18-7.34 (m, 9H), 7.36-7.47 (m, 3H), 7.42 (d, J=7.8 Hz, 1H), 7.55-7.65 (m, 1H), 7.83-7.94 (m, 2H).

(2) Synthesis of (R)-2-[2-(3-benzoyl-2,4-dioxo-3,4-dihydropyrimidin-1 (2H)-yl)ethoxy]-3-[bis(4-methoxyphen yl)(phenyl)methoxy]propyl(2-cyanoethyl)diisopropylphosphoramidite (Compound 18)

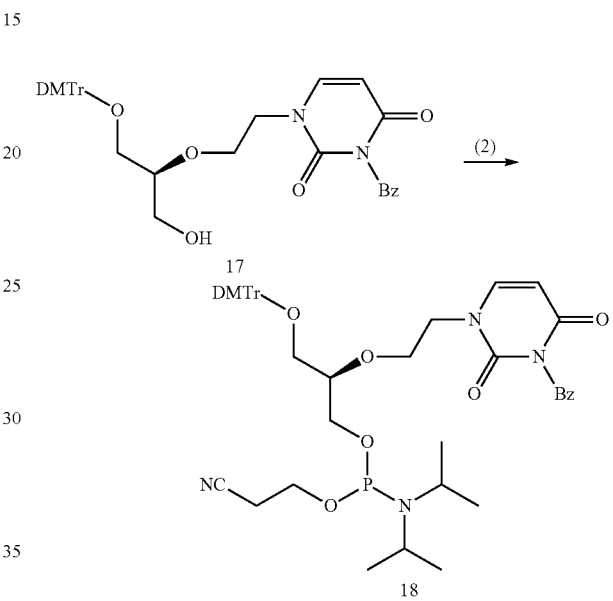

According to the method in Example 1-(7), the titled compound 18 (270 mg, 0.32 mmol) was obtained from the compound 17 (400 mg, 0.63 mmol) obtained in Example 3-(1), DIPEA (0.65 mL, 3.77 mmol), 2-cyanoethyl N,N-diisopropylchlorophosphoramidite (0.20 mL, 0.72 mmol) and methylene chloride (6.0 mL).

$^1$H-NMR (400 MHz, CDCl$_3$) δ (ppm): 1.05-1.24 (m, 12H), 2.48-2.63 (m, 2H), 3.12-3.30 (m, 2H), 3.43-4.04 (m, 11H), 3.77 (s, 6H), 5.58-5.69 (m, 1H), 6.75-6.88 (m, 4H), 7.16-7.34 (m, 8H), 7.35-7.46 (m, 3H), 7.47-7.55 (m, 1H), 7.55-7.63 (m, 1H), 7.83-7.93 (m, 2H).

Example 4

Synthesis of (R)-3-[bis(4-methoxyphenyl)(phenyl)methoxy]-2-[2-(4-isobutylamido-2-oxopyrimidin-1 (2H)-yl)ethoxy]propyl(2-cyanoethyl)diisopropylphosphoramidite

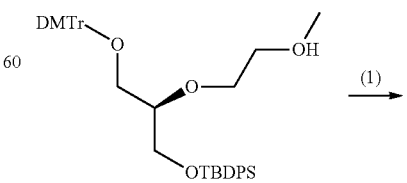

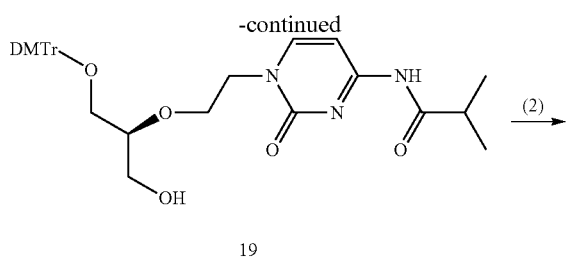

19

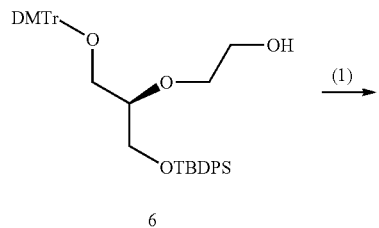

20

(1) Synthesis of (S)—N-{1-[2-({1-[bis(4-methoxy-phenyl)(phenyl)methoxy]-3-hydroxypropan-2-yl}oxy)ethyl]-2-oxo-1,2-dihydropyrimidin-4-yl}isobutylamide (Compound 19)

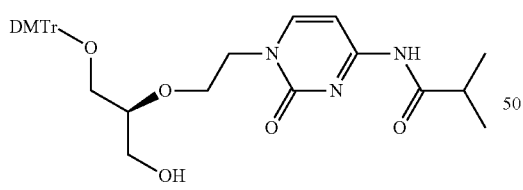

19

The compound 6 (1.1 g, 1.63 mmol) obtained in Example 1-(5), $N^4$-isobutyrylcytosine (0.59 g, 3.25 mmol) and triphenylphosphine (1.07 g, 6.54 mmol) were suspended in THF (16 mL), and DIAD (0.80 mL, 4.06 mmol) was added dropwise thereto under ice cooling and stirred under a nitrogen atmosphere at room temperature for 19 hours. The reaction solution was concentrated under reduced pressure, and the obtained residue was purified by column chromatography (n-heptane/ethyl acetate/0.5% TEA) to obtain an $N^4$-isobutyrylcytosine substituted substance (1.6 g).

The obtained crude substituted substance was dissolved with THF (1.6 mL), and a 1 M TBAF/THF solution (7.3 mL, 7.3 mmol) was added thereto under ice cooling and stirred under ice cooling for 2 hours. To the reaction mixture was added water and the mixture was extracted with ethyl acetate. The organic phase was washed with a mixed solution (1:1) of a saturated sodium hydrogen carbonate aqueous solution and a saturated sodium chloride solution and dried over anhydrous magnesium sulphate. After filtration, the solvent was distilled off under reduced pressure. The residue was purified by silica gel column chromatography (n-heptane/ethyl acetate/0.5% TEA) to obtain the titled compound 19 (489 mg, 0.81 mmol).

$^1$H-NMR (400 MHz, CDCl$_3$) δ (ppm): 1.20-1.26 (m, 6H), 1.88-1.98 (m, 1H), 2.45-2.49 (m, 1H), 3.11-3.26 (m, 2H), 3.43-3.53 (m, 1H), 3.54-3.73 (m, 2H), 3.77-3.91 (m, 2H), 3.80 (s, 6H), 3.92-4.03 (m, 1H), 4.07-4.18 (m, 1H), 6.79-6.86 (m, 4H), 7.18-7.34 (m, 8H), 7.35-7.42 (m, 2H), 7.66-7.72 (m, 1H), 7.87 (br s, 1H).

(2) Synthesis of (R)-3-[bis(4-methoxyphenyl)(phenyl)methoxy]-2-[2-(4-isobutylamido-2-oxopyrimidin-1(2H)-yl)ethoxy]propyl(2-cyanoethyl)diisopropylphosphoramidite (Compound 20)

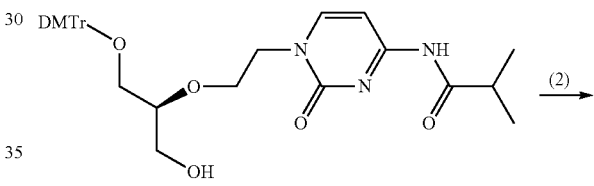

19

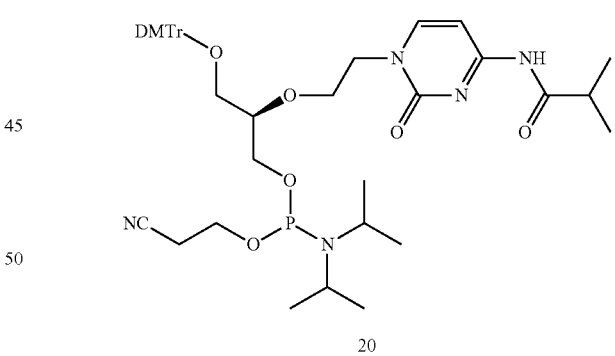

20

According to the method in Example 1-(7), the titled compound 20 (288 mg, 0.36 mmol) was obtained from the compound 19 (450 mg, 0.75 mmol) obtained in Example 4-(1), DIPEA (0.58 mL, 3.38 mmol), 2-cyanoethyl N,N-diisopropylchlorophosphoramidite (0.25 mL, 1.12 mmol) and methylene chloride (7.5 mL).

$^1$H-NMR (400 MHz, CDCl$_3$) δ (ppm): 1.05-1.19 (m, 12H), 1.19-1.25 (m, 6H), 2.44-2.66 (m, 3H), 3.05-3.25 (m, 2H), 3.41-4.18 (m, 11H), 3.80 (s, 6H), 6.77-6.87 (m, 4H), 7.16-7.33 (m, 8H), 7.34-7.43 (m, 2H), 7.72-7.81 (m, 1H), 7.87 (br s, 1H).

Example 5

Synthesis of 9-{2-[((2R)-1-[bis(4-methoxyphenyl)(phenyl)methoxy]-3-{[(2-cyanoethoxy)(diisopropylamido)phosphino]oxy}propan-2-yl)oxy]ethyl}-2-isobutylamido-9H-purin-6-yl diphenylcarbamate

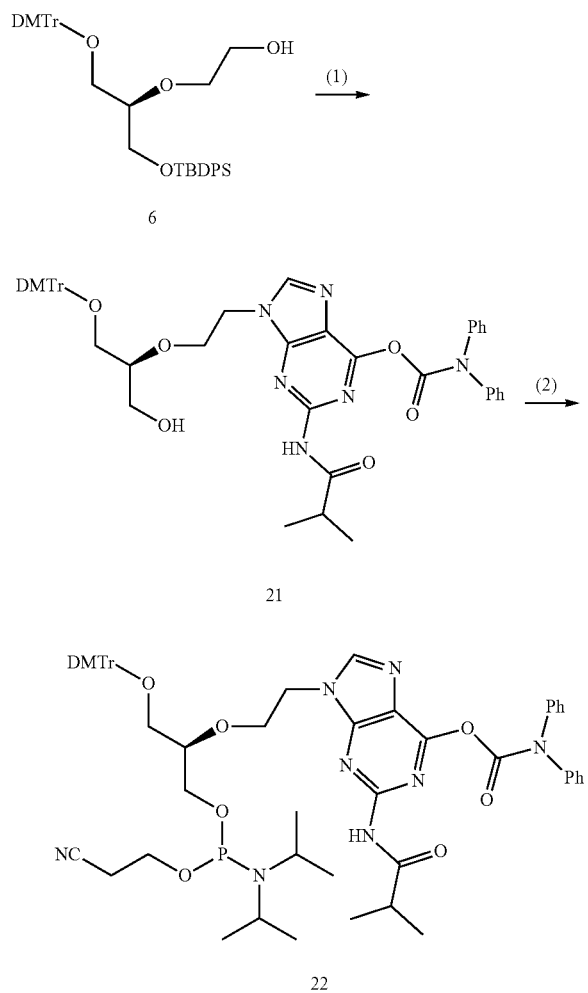

(1) Synthesis of (S)-9-[2-({1-[bis(4-methoxyphenyl)(phenyl)methoxy]-3-hydroxypropan-2-yl}oxy)ethyl]-2-diisopropylamido-9H-purin-6-yl diphenylcarbamate (Compound 21)

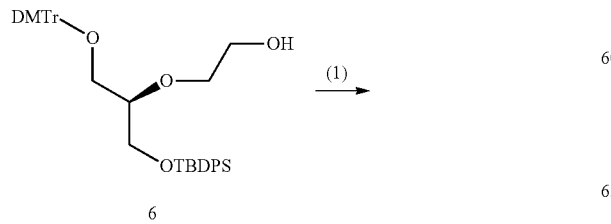

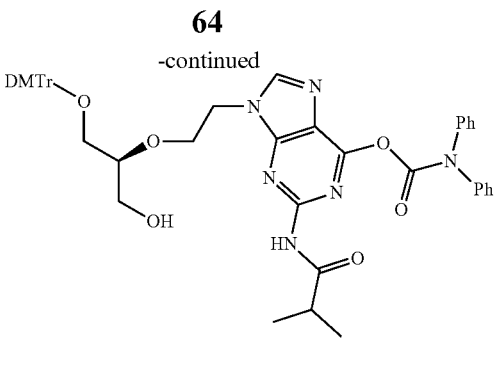

The compound 6 (0.86 g, 1.27 mmol) obtained in Example 1-(5), $N^2$-isobutyryl-$O^6$-diphenylcarbamoylguanine (0.90 g, 2.16 mmol) and triphenylphosphine (0.73 g, 2.80 mmol) were suspended in THF (13 mL), and DIAD (0.55 mL, 2.80 mmol) was added dropwise thereto under ice cooling and stirred under a nitrogen atmosphere at room temperature for 2 hours. The reaction solution was concentrated under reduced pressure, and the obtained residue was purified by column chromatography (n-heptane/ethyl acetate/0.5% TEA) to obtain an $N^2$-isobutyryl-$O^6$-diphenylcarbamoylguanine substituted substance (1.3 g). The obtained crude substituted substance was dissolved with THF (1.2 mL), and a 1 M TBAF/THF solution (4.8 mL, 4.8 mmol) was added thereto under ice cooling and stirred under ice cooling for 2 hours. To the reaction mixture was added water and the mixture was extracted with ethyl acetate. The organic phase was washed with a mixed solution (1:1) of a saturated sodium hydrogen carbonate aqueous solution and a saturated sodium chloride solution and dried over anhydrous magnesium sulphate. After filtration, the solvent was distilled off under reduced pressure. The residue was purified by silica gel column chromatography (n-heptane/ethyl acetate/0.5% TEA) to obtain the titled compound 21 (680 mg, 0.81 mmol).

$^1$H-NMR (400 MHz, CDCl$_3$) δ (ppm): 1.21-1.30 (m, 6H), 2.39-2.49 (m, 1H), 2.75-2.98 (m, 1H), 3.11-3.22 (m, 2H), 3.46-3.71 (m, 3H), 3.77 (s, 6H), 3.82-3.92 (m, 1H), 3.92-4.03 (m, 1H), 4.25-4.36 (m, 1H), 4.38-4.51 (m, 1H), 6.76-6.85 (m, 4H), 7.15-7.52 (m, 19H), 7.99 (s, 1H), 8.06 (s, 1H).

(2) Synthesis of 9-{2-[((2R)-1-[bis(4-methoxyphenyl)(phenyl)methoxy]-3-{[(2-cyanoethoxy)(diisopropylamido)phosphino]oxy}propan-2-yl)oxy]ethyl}-2-isobutylamido-9H-purin-6-yl diphenylcarbamate (Compound 22)

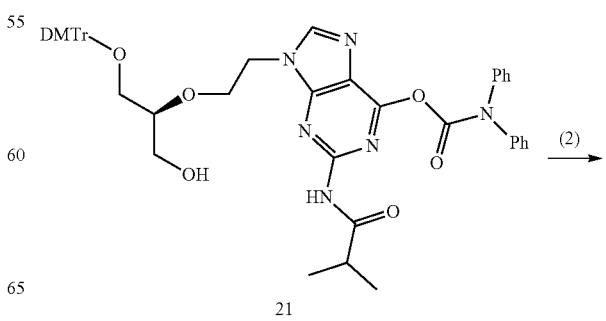

-continued

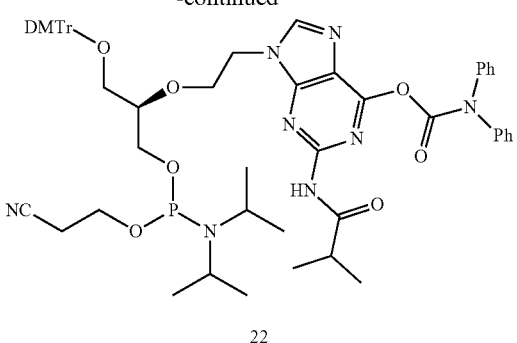

22

The compound 21 (400 mg, 0.478 mmol) obtained in Example 5-(1) and DIPEA (0.45 mL, 2.63 mmol) were dissolved with methylene chloride (4.8 mL), and 2-cyanoethyl N,N-diisopropylchlorophosphoramidite (0.13 mL, 0.574 mmol) was added thereto under ice cooling and stirred for 2 hours. Under ice cooling, 2-cyanoethyl N,N-diisopropylchlorophosphoramidite (0.064 mL, 0.287 mmol) was further added and stirred for 10 minutes. To the reaction solution, a saturated sodium hydrogen carbonate aqueous solution was added and extracted with ethyl acetate. The organic phase was dried over anhydrous magnesium sulphate and filtered and the solvent was distilled off under reduced pressure. The residue was purified by silica gel column chromatography (n-heptane/ethyl acetate/0.5% TEA) to obtain the titled compound 22 (260 mg, 0.25 mmol).

$^1$H-NMR (400 MHz, CDCl$_3$) δ (ppm): 1.04-1.18 (m, 12H), 1.22-1.30 (m, 6H), 2.44-2.55 (m, 2H), 2.83-3.02 (m, 1H), 3.11-3.26 (m, 2H), 3.40-3.82 (m, 7H), 3.76 (s, 6H), 3.82-4.01 (m, 2H), 4.24-4.47 (m, 2H), 6.76-6.85 (m, 4H), 7.15-7.52 (m, 19H), 7.99 (s, 1H), 8.06 (s, 1H).

Example 6

Synthesis of (R)-2-(2-(6-benzamide-9H-purin-9-yl)ethoxy)-3-(bis(4-methoxyphenyl)(phenyl)methoxy)propyl(2-cyanoethyl)diisopropylphosphoramide

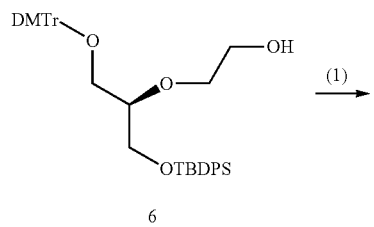

6

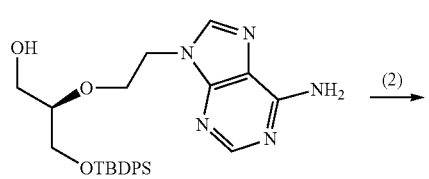

23

-continued

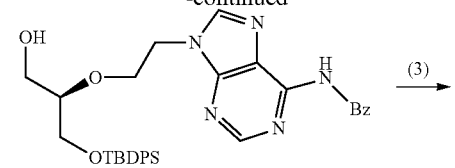

24

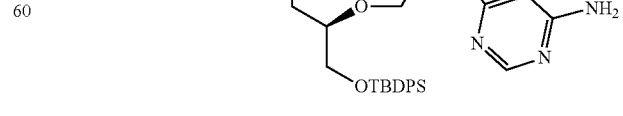

25

26

27

(1) Synthesis of (R)-2-[2-(6-amino-9H-purin-9-yl)ethoxy]-3-[(tert-butyldiphenylsilyl)oxy]propan-1-ol (Compound 23)

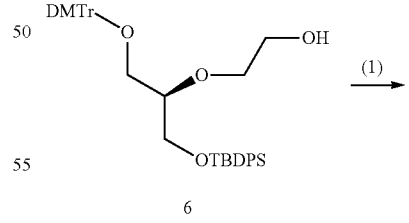

6

23

The compound 6 (2.5 g, 3.69 mmol) obtained in Example 1-(5), $N^6,N^6$-di-Boc-adenine (2.48 g, 7.39 mmol) and triphenylphosphine (2.23 g, 8.49 mmol) were dissolved with THF (37 mL), and DIAD (1.7 mL, 8.49 mmol) was added dropwise thereto under ice cooling and stirred under a nitrogen atmosphere at room temperature for 3 hours. The reaction solution was concentrated under reduced pressure, and the obtained residue was purified by column chromatography (n-heptane/ethyl acetate/0.5% TEA) to obtain an $N^6,N^6$-di-Boc-adenine substituted substance (5.06 g). The obtained crude substituted substance was dissolved with methylene chloride (37 mL), and a 1 M TFA (10 mL, 130.7 mmol) was added dropwise thereto under ice cooling and stirred at room temperature for 4 hours. Under ice cooling, a 5 N sodium hydroxide aqueous solution (26 mL) was added to the reaction mixture and stirred at room temperature for 15 minutes and a saturated sodium chloride solution was added thereto. The obtained mixture was extracted with chloroform and dried over anhydrous magnesium sulphate. After filtration, the solvent was distilled off under reduced pressure. The residue was purified by silica gel column chromatography (MeOH/ethyl acetate) to obtain the titled compound 23 (1.45 g, 2.94 mmol).

$^1$H-NMR (400 MHz, CDCl$_3$) δ (ppm): 1.03 (s, 9H), 3.46-3.74 (m, 5H), 3.76-4.00 (m, 3H), 4.14-4.26 (m, 1H), 4.38-4.52 (m, 1H), 5.59 (br s, 2H), 7.33-7.47 (m, 6H), 7.58-7.67 (m, 4H), 7.83 (s, 1H), 8.34 (s, 1H).

(2) Synthesis of (R)—N-{9-[2-({1-[(tert-butyldiphenylsilyl)oxy]-3-hydroxypropan-2-yl}oxy)ethyl]-9H-purin-6-yl}benzamide (Compound 24)

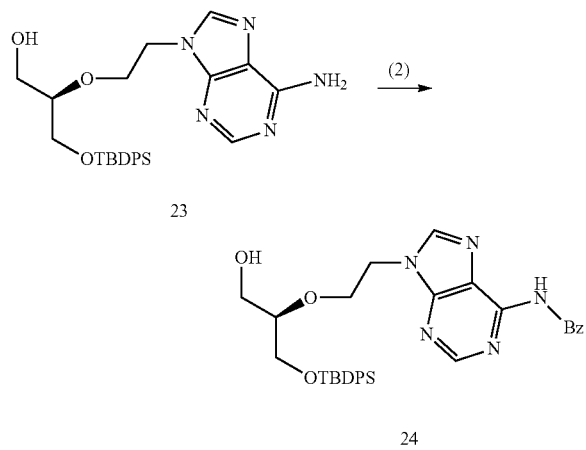

The compound 23 (1.45 g, 2.95 mmol) obtained in Example 6-(1) was dissolved with pyridine (14.8 mL) and benzoyl chloride (2.7 mL, 23.6 mmol) was added dropwise thereto under ice cooling and stirred at room temperature for 16 hours. After addition of MeOH (8.3 mL), the reaction solution was concentrated under reduced pressure. Water was added to the obtained residue and the mixture was extracted with ethyl acetate. The organic phase was dried over anhydrous magnesium sulphate and filtered and the solvent was distilled off under reduced pressure to obtain a crude product (3.3 g).

The obtained crude product was dissolved with THF (28 mL) and EtOH (13 mL), and a 1 N sodium hydroxide aqueous solution (5.9 mL, 5.9 mmol) was added thereto under ice cooling and stirred at room temperature for 1.5 hours. To the reaction mixture was added a saturated ammonium chloride aqueous solution (50 mL) and the mixture was extracted with ethyl acetate. The organic phase was dried over anhydrous magnesium sulphate and filtered and the solvent was distilled off under reduced pressure. The residue was purified by silica gel column chromatography (MeOH/ethyl acetate) to obtain the titled compound 24 (900 mg, 1.51 mmol).

$^1$H-NMR (400 MHz, CDCl$_3$) δ (ppm): 1.03 (s, 9H), 2.91-3.03 (m, 1H), 3.42-3.77 (m, 6H), 3.78-4.01 (m, 2H), 4.25-4.38 (m, 1H), 4.43-4.57 (m, 1H), 7.32-7.48 (m, 6H), 7.49-7.57 (m, 2H), 7.58-7.67 (m, 5H), 7.99-8.06 (m, 2H), 8.09 (s, 1H), 8.80 (s, 1H), 8.99 (s, 1H).

(3) Synthesis of (R)—N-{9-[2-({1-[bis(4-methoxyphenyl)(phenyl)methoxy]-3-[(tert-butyldiphenylsilyl)oxy]propan-2-yl}oxy)ethyl]-9H-purin-6-yl}benzamide (Compound 25)

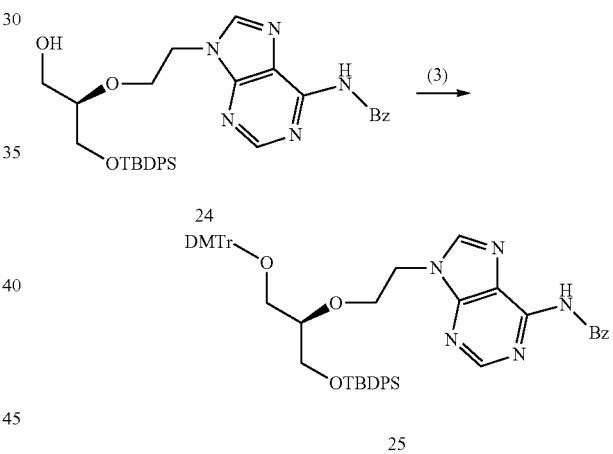

The compound 24 (900 mg, 1.51 mmol) obtained in Example 6-(2) was dissolved with pyridine (9 mL), and 4,4'-dimethoxytrityl chloride (768 mg, 2.26 mmol) was added thereto under ice cooling. After stirring at room temperature for 4 hours. 4,4'-dimethoxytrityl chloride (113 mg, 0.33 mmol) was further added and stirred at room temperature for 2 hours. Under ice cooling, to the reaction mixture was added ice water and extracted with ethyl acetate. The organic phase was dried over anhydrous magnesium sulphate and filtered and the solvent was distilled off under reduced pressure. The residue was purified by silica gel column chromatography (n-heptane/ethyl acetate/0.5% TEA) to obtain the titled compound 25 (1.17 g, 1.30 mmol).

$^1$H-NMR (400 MHz, CDCl$_3$) δ (ppm): 0.94 (s, 9H), 2.91-3.03 (m, 1H), 3.42-3.77 (m, 6H), 3.78-4.01 (m, 2H), 4.25-4.38 (m, 1H), 4.43-4.57 (m, 1H), 6.71-6.81 (m, 4H), 7.15-7.27 (m, 7H), 7.28-7.45 (m, 8H), 7.47-7.67 (m, 7H), 7.99-8.05 (m, 2H), 8.06 (s, 1H), 8.80 (s, 1H), 8.99 (s, 1H).

(4) Synthesis of (S)—N-{9-[2-({1-[bis(4-methoxyphenyl)(phenyl)methoxy]-3-hydroxypropan-2-yl}oxy)ethyl]-9H-purin-6-yl}benzamide (Compound 26)

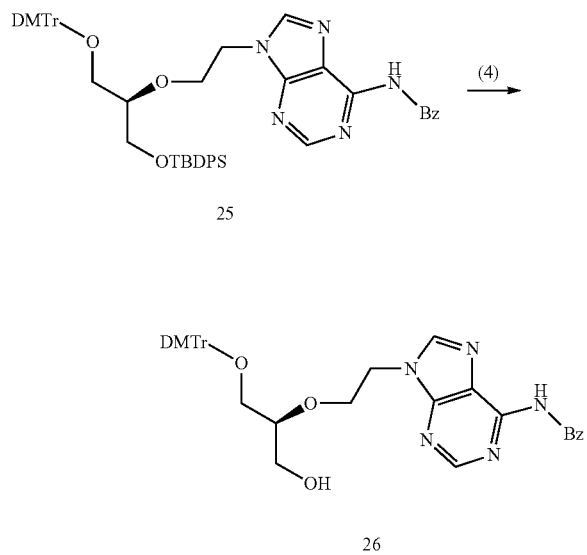

The compound 25 (1.17 g, 1.30 mmol) obtained in Example 6-(3) was dissolved with THF (1.3 mL), and a 1 M TBAF/THF solution (6.5 mL, 6.5 mmol) was added dropwise thereto under ice cooling and stirred at the same temperature for 4 hours. To the reaction mixture was added water and the mixture was extracted with ethyl acetate. The organic phase was dried over anhydrous magnesium sulphate and filtered and the solvent was distilled off under reduced pressure. The residue was purified by silica gel column chromatography (methanol/ethyl acetate/0.5% TEA) to obtain the titled compound 26 (810 mg, 1.23 mmol).

$^1$H-NMR (400 MHz, CDCl$_3$) δ (ppm): 2.95-3.04 (m, 1H), 3.10-3.20 (m, 2H), 3.48-3.71 (m, 3H), 3.88 (s, 6H), 3.86-3.97 (m, 1H), 3.98-4.09 (m, 1H), 4.32-4.43 (m, 1H), 4.48-4.60 (m, 1H), 6.76-6.85 (m, 4H), 7.15-7.32 (m, 7H), 7.33-7.41 (m, 2H), 7.49-7.57 (m, 2H), 7.58-7.66 (m, 1H), 7.99-8.07 (m, 2H), 8.11 (s, 1H), 8.80 (s, 1H), 9.01 (s, 1H).

(5) Synthesis of (R)-2-(2-(6-benzamide-9H-purin-9-yl)ethoxy)-3-(bis(4-methoxyphenyl)(phenyl)methoxy)propyl(2-cyanoethyl)diisopropylphosphoramide (Compound 27)

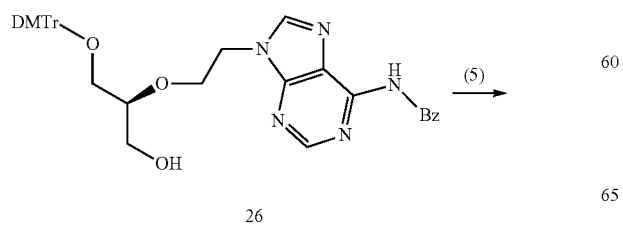

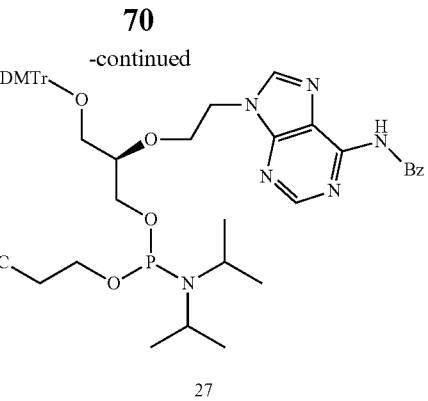

According to the method in Example 1-(7), the titled compound 27 (242 mg, 0.28 mmol) was obtained from the compound 26 (450 mg, 0.68 mmol) obtained in Example 6-(4), DIPEA (0.70 mL, 4.1 mmol), 2-cyanoethyl N,N-diisopropylchlorophosphoramidite (0.23 mL, 1.0 mmol) and methylene chloride (6.8 mL).

$^1$H-NMR (400 MHz, CDCl$_3$) δ (ppm): 1.02-1.20 (m, 12H), 2.50-2.65 (m, 2H), 3.08-3.26 (m, 2H), 3.43-3.77 (m, 7H), 3.77 (s, 6H), 3.90-4.05 (m, 2H), 4.39-4.50 (m, 2H), 6.75-6.85 (m, 4H), 7.15-7.33 (m, 7H), 7.33-7.42 (m, 2H), 7.48-7.58 (m, 2H), 7.58-7.66 (m, 1H), 7.99-8.08 (m, 2H), 8.20 (s, 1H), 8.81 (s, 1H), 9.05 (s, 1H).

Example 7

Synthesis of (R)-4-{3-[bis(4-methoxyphenyl)(phenyl)methoxy]-2-[2-(2,4-dioxo-3,4-dihydropyrimidin-1(2H)-yl)ethoxy]propoxy}-4-oxobutanoate-CPG support

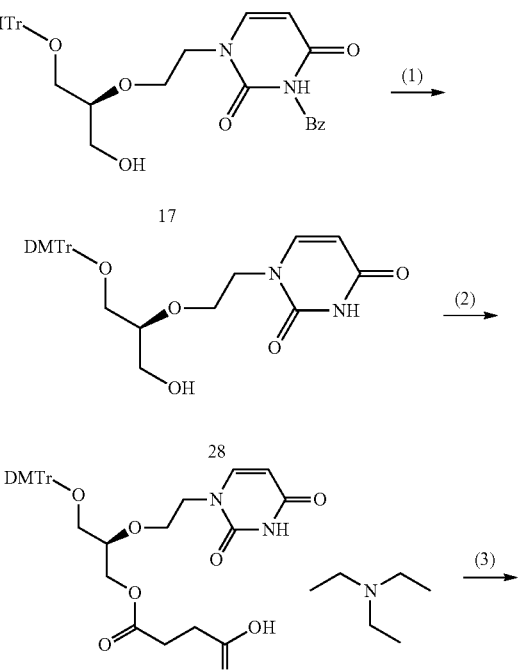

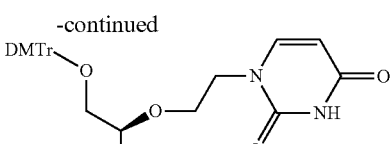

(1) Synthesis of (S)-1-[2-({1-[bis(4-methoxyphenyl)(phenyl)methoxy]-3-hydroxypropan-2-yl}oxy)ethyl]pyrimidine-2,4(1H,3H)-dione (Compound 28)

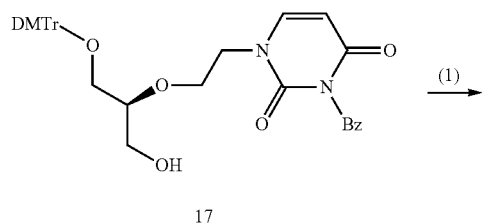

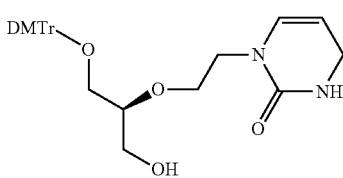

The compound 17 (100 mg, 0.157 mmol) obtained in Example 3-(1) was dissolved at room temperature in a 2 M dimethylamine/THF solution (2.0 mL, 2.0 mmol) and stirred for 1 hour. The reaction solution was distilled off under reduced pressure. The residue was purified by silica gel column chromatography (methanol/ethyl acetate/0.5% TEA) to obtain the titled compound 28 (83 mg, 0.156 mmol).

$^1$H-NMR (400 MHz, CDCl$_3$) δ (ppm): 1.93-2.00 (m, 1H), 3.13-3.25 (m, 2H), 3.46-3.55 (m, 1H), 3.57-4.00 (m, 6H), 3.80 (s, 6H), 5.54-5.60 (m, 1H), 6.83 (d, J=9.0 Hz, 4H), 7.18-7.34 (m, 4H), 7.28 (d, J=9.0 Hz, 4H), 7.35-7.42 (m, 2H), 8.03 (br s, 1H).

(2) Synthesis of triethylamine (R)-4-{3-[bis(4-methoxyphenyl)(phenyl)methoxy]-2-[2-(2,4-dioxo-3,4-dihydropyrimidin-1(2H)-yl)ethoxy]propoxy}-4-oxobutanoate (Compound 29)

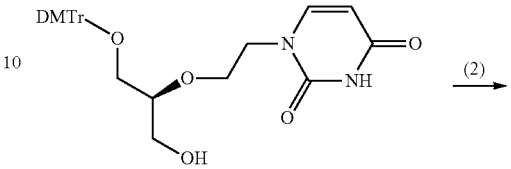

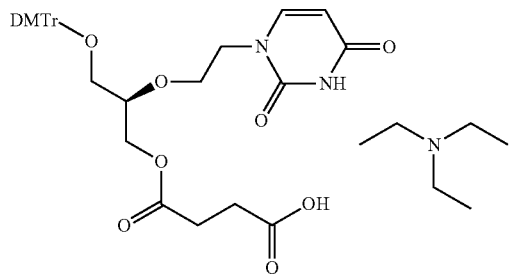

The compound 28 (40 mg, 0.075 mmol) obtained in Example 7-(1) and DMAP (27.5 mg, 0.225 mmol) were dissolved with methylene chloride (0.80 mL), and succinic anhydride (15 mg, 0.15 mmol) was added thereto at room temperature and stirred for 16 hours. The reaction solution was purified by silica gel column chromatography (chloroform/methanol/0.5% TEA) to obtain the titled compound 29 (38 mg, 0.052 mmol).

$^1$H-NMR (400 MHz, CDCl$_3$) δ (ppm): 1.27 (t, J=7.4 Hz, 9H), 2.58 (s, 4H), 3.00 (q, J=7.4 Hz, 6H) 3.10-3.21 (m, 2H), 3.56-3.68 (m, 1H), 3.70-3.85 (m, 2H), 3.80 (s, 6H), 3.89-4.01 (m, 1H), 4.05-4.18 (m, 2H), 4.22-4.33 (m, 1H), 5.54-5.60 (m, 1H), 6.83 (d, J=9.0 Hz, 4H), 7.18-7.34 (m, 4H), 7.28 (d, J=9.0 Hz, 4H), 7.35-7.42 (m, 2H).

(3) Synthesis of (R)-4-{3-[bis(4-methoxyphenyl)(phenyl)methoxy]-2-[2-(2,4-dioxo-3,4-dihydropyrimidin-1(2H)-yl)ethoxy]propoxy}-4-oxobutanoate-CPG support (CPG support 30)

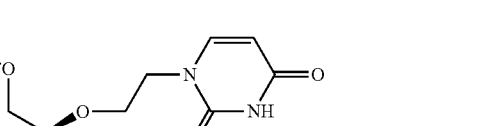

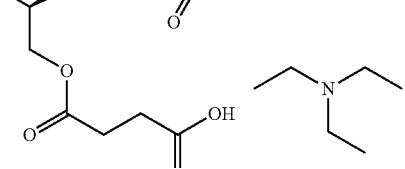

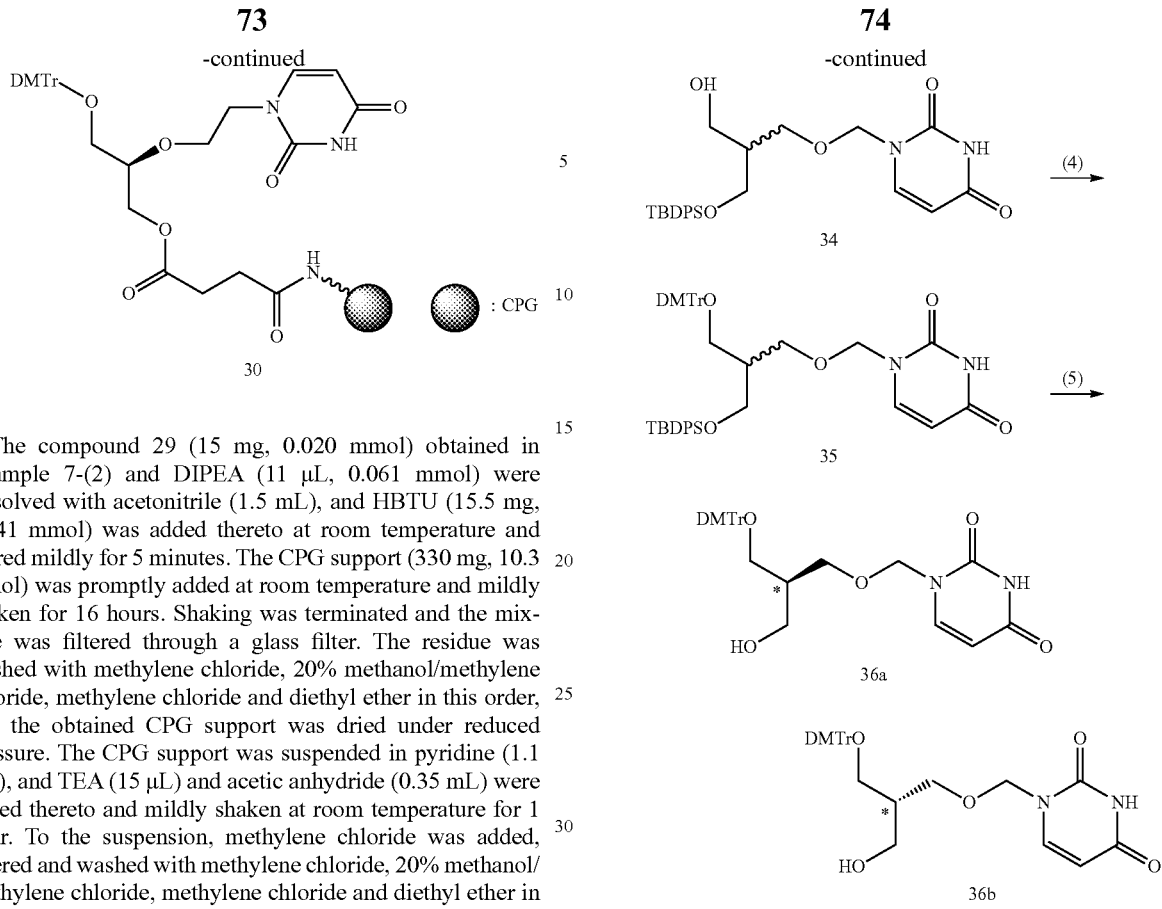

The compound 29 (15 mg, 0.020 mmol) obtained in Example 7-(2) and DIPEA (11 µL, 0.061 mmol) were dissolved with acetonitrile (1.5 mL), and HBTU (15.5 mg, 0.041 mmol) was added thereto at room temperature and stirred mildly for 5 minutes. The CPG support (330 mg, 10.3 mmol) was promptly added at room temperature and mildly shaken for 16 hours. Shaking was terminated and the mixture was filtered through a glass filter. The residue was washed with methylene chloride, 20% methanol/methylene chloride, methylene chloride and diethyl ether in this order, and the obtained CPG support was dried under reduced pressure. The CPG support was suspended in pyridine (1.1 mL), and TEA (15 µL) and acetic anhydride (0.35 mL) were added thereto and mildly shaken at room temperature for 1 hour. To the suspension, methylene chloride was added, filtered and washed with methylene chloride, 20% methanol/methylene chloride, methylene chloride and diethyl ether in this order and the obtained CPG support was dried under reduced pressure to obtain the titled CPG support 30 (310 mg). The loading amount calculated from the absorbance after treatment with 5% dichloroacetic acid/1,2-dichloroethane was 61.6 µmol/g.

Synthesis Example 8

Synthesis of (R*)-1-({3-[bis(4-methoxyphenyl)(phenyl)methoxy]-2-(hydroxymethyl)propoxy}methyl)pyrimidine-2,4(1H,3H)-dione and (S*)-1-({3-[bis(4-methoxyphenyl)(phenyl)methoxy]-2-(hydroxymethyl)propoxy}methyl)pyrimidine-2,4(1H,3H)-dione

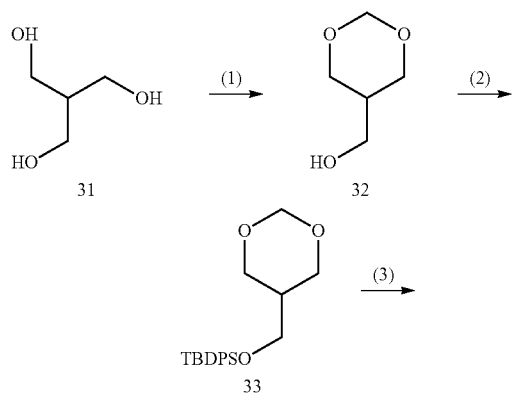

(1) Synthesis of (1,3-dioxan-5-yl)methanol (Compound 32)

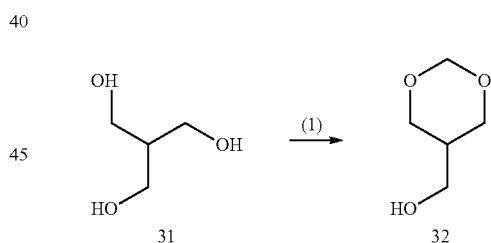

2-(Hydroxymethyl)-1,3-propanediol (Compound 31, CAS number: 4704-94-3, 3.0 g, 28.3 mmol), formaldehyde dimethyl acetal (8.7 mL, 98.9 mmol) and lithium bromide (0.49 g, 5.7 mmol) were suspended in methylene chloride (14.1 mL), and p-toluenesulphonic acid monohydrate (0.54 g, 2.83 mmol) was added thereto at room temperature and stirred for 40 hours. To the reaction solution was added TEA (3 mL) and concentrated under reduced pressure. The obtained residue was purified by column chromatography (n-heptane/ethyl acetate) to obtain the titled compound 32 (1.48 g, 12.5 mmol).

$^1$H-NMR (400 MHz, CDCl$_3$) δ (ppm): 1.53 (t, J=5.1 Hz, 1H), 1.96 (ddddd, J=3.9, 5.9, 6.6, 11.3, 11.7 Hz 1H), 3.76 (dd, J=5.1, 6.6 Hz, 1H), 3.80 (dd, J=5.9, 11.7 Hz, 1H), 4.02 (dd, J=3.9, 11.3 Hz, 2H), 4.81 (d, J=6.3 Hz, 1H), 4.87 (d, J=6.3 Hz, 1H).

(2) Synthesis of [(1,3-dioxan-5-yl)methoxy](tert-butyl)diphenylsilane (Compound 33)

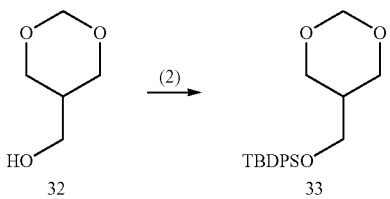

The compound 32 (1.48 g, 12.5 mmol) obtained in Synthesis Example 8-(1) and imidazole (1.71 g, 25.1 mmol) were dissolved with DMF (25 mL) and tert-butyldiphenylsilyl chloride (3.9 mL, 15.0 mmol) was slowly added thereto at room temperature and stirred for 15 hours. To the reaction solution was added water and the mixture was extracted with diethyl ether. The organic phase was dried over anhydrous magnesium sulphate and filtered and the solvent was distilled off under reduced pressure. The residue was purified by silica gel column chromatography (n-heptane/ethyl acetate) to obtain the titled compound 33 (3.9 g, 10.9 mmol).

$^1$H-NMR (400 MHz, CDCl$_3$) δ (ppm): 2.07 (ddddd, J=4.1, 6.6, 7.4, 11.3, 11.5 Hz, 1H), 3.65 (d, J=6.6 Hz, 2H), 3.72 (dd, J=7.4, 11.3 Hz, 1H), 4.01 (dd, J=4.1, 11.5 Hz, 1H), 4.81 (d, J=6.0 Hz, 1H), 4.87 (d, J=6.0 Hz, 1H), 7.34-7.47 (m, 6H), 7.60-7.68 (m, 4H).

(3) Synthesis of (RS)-1-({3-[(tert-butyldiphenylsilyl)oxy]-2-(hydroxymethyl)propoxy}methyl)pyrimidine-2,4(1H,3H)-dione (Compound 34)

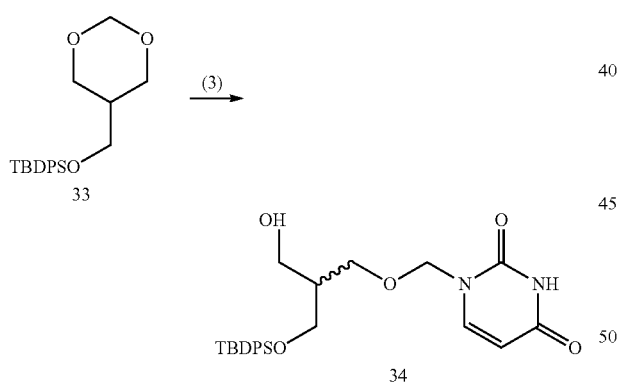

Uracil (1.89 g, 16.8 mmol) was suspended in 1,2-dichloroethane (28 mL) and N,O-bis(trimethylsilyl)acetamide (8.2 mL, 33.7 mmol) was added thereto at room temperature and refluxed under heating for 1 hour. After being left to cool to room temperature, the reaction solution was concentrated under reduced pressure. The obtained residue was dissolved with 1,2-dichloroethane (42 mL) and added to the compound 33 (2.0 g, 5.61 mmol) obtained in Synthesis Example 8-(2). Tert-butyldiphenylsilyltriflate (2.6 mL, 11.2 mmol) was added at room temperature and stirred at 80° C. for 1 hour. The reaction solution was left to cool to room temperature and poured under ice cooling to a saturated sodium hydrogen carbonate aqueous solution containing ice. The mixture was extracted with ethyl acetate and dried over anhydrous magnesium sulphate. After filtration, the solvent was distilled off under reduced pressure. The residue was purified by silica gel column chromatography (n-heptane/ethyl acetate) to obtain the titled compound 34 (1.9 g, 4.05 mmol).

$^1$H-NMR (400 MHz, CDCl$_3$) δ (ppm): 1.05 (s, 9H), 1.96-2.09 (m, 1H), 2.11-2.20 (m, 1H), 3.57-3.84 (m, 6H), 5.08 (s, 2H), 5.72 (d, J=8.2 Hz, 1H), 7.21 (d, J=8.2 Hz, 1H), 7.36-7.49 (m, 6H), 7.60-7.67 (m, 4H), 8.37 (br s, 1H).

(4) Synthesis of (RS)-1-({3-[bis(4-methoxyphenyl)(phenyl)methoxy]-2-{[(tert-butyldiphenylsilyl)oxy]methyl}propoxy}methyl)pyrimidine-2,4(1H,3H)-dione (Compound 35)

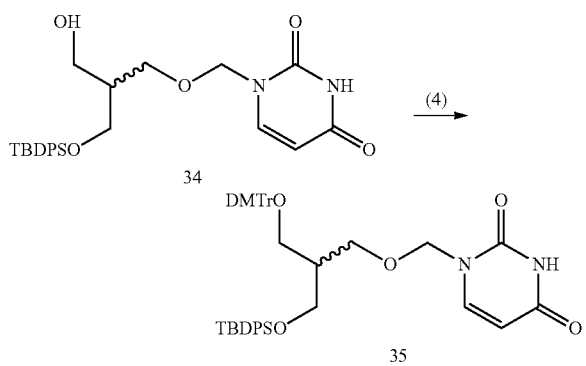

According to the method in Example 1-(7), the titled compound 35 (2.9 g, 3.76 mmol) was obtained from the compound 34 (1.9 g, 4.05 mmol) obtained in Synthesis Example 8-(3), pyridine (25 mL) and 4,4'-dimethoxytrityl chloride (1.79 g, 5.27 mmol).

$^1$H-NMR (400 MHz, CDCl$_3$) δ (ppm): 0.95 (s, 9H), 2.07-2.21 (m, 1H), 3.06-3.25 (m, 2H), 3.57-3.66 (m, 2H), 3.69-3.76 (m, 2H), 3.78 (s, 6H), 4.99 (s, 2H), 5.61 (d, J=8.2 Hz, 1H), 6.75-6.84 (m, 4H), 7.07 (d, J=8.2 Hz, 1H), 7.15-7.47 (m, 15H), 7.54-7.63 (m, 4H), 7.97 (br s, 1H).

(5) Synthesis of (R*)-1-({3-[bis(4-methoxyphenyl)(phenyl)methoxy]-2-(hydroxymethyl)propoxy}methyl)pyrimidine-2,4(1H,3H)-dione (Compound 36a) and (S*)-1-({3-[bis(4-methoxyphenyl)(phenyl)methoxy]-2-(hydroxymethyl)propoxy}methyl)pyrimidine-2,4(1H,3H)-dione (Compound 36b)

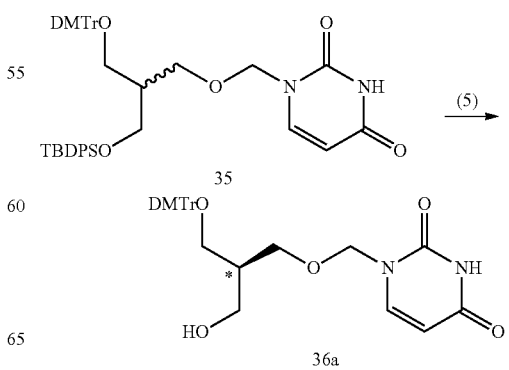

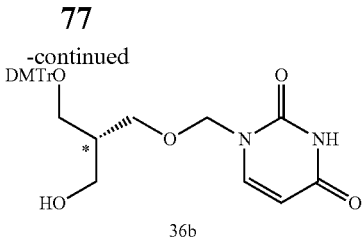

36b

According to the method in Example 6-(4), an enantiomer mixture (1.65 g, 3.10 mmol) of the titled compounds was obtained from the compound 35 (2.9 g, 3.76 mmol) obtained in Synthesis Example 8-(4), THF (3.8 mL) and a 1 M TBAF/THF solution (20.7 mL, 20.7 mmol).

The obtained mixture (260 mg) was subjected to supercritical fluid chromatography (mobile phase: $CO_2$:2-propanol:acetonitrile (70:15:15), 120 bar, 40° C., flow rate: 100 mL/min) using CHIRALPAK (registered trademark) AD-H (2 cm×25 cm) manufactured by Daicel Corporation to collect fractions of 12 mg each, and the titled compound (36a: 113 mg, >99% ee) having a retention time at 4.4 minutes as analysed with CHIRALPAK (registered trademark) AD-H (4.6 mm×150 mm, mobile phase: 2-propanol: n-hexane (50:50), flow rate: 1 mL/min) manufactured by Daicel Corporation and the titled compound (36b: 123 mg, >99% ee) having a retention time of 4.9 minutes were obtained.

36a:
$^1$H-NMR (400 MHz, CDCl$_3$) δ (ppm): 2.02-2.15 (m, 1H), 3.13-3.28 (m, 2H), 3.62-3.76 (m, 4H), 3.79 (s, 6H), 5.08 (s, 2H), 5.71 (d, J=8.2 Hz, 1H), 6.78-6.88 (m, 4H), 7.15-7.43 (m, 9H), 7.19 (d, J=8.2 Hz, 1H), 8.29 (br s, 1H).

36b:
$^1$H-NMR (400 MHz, CDCl$_3$) δ (ppm): 2.02-2.15 (m, 1H), 3.13-3.28 (m, 2H), 3.62-3.76 (m, 4H), 3.79 (s, 6H), 5.08 (s, 2H), 5.71 (d, J=8.2 Hz, 1H), 6.78-6.88 (m, 4H), 7.15-7.43 (m, 9H), 7.19 (d, J=8.2 Hz, 1H), 8.29 (br s, 1H).

Example 9

Synthesis of (S*)-3-[bis(4-methoxyphenyl)(phenyl)methoxy]-2-{[(2,4-dioxo-3,4-dihydropyrimidin-1(2H)-yl)methoxy]methyl}propyl(2-cyanoethyl)diisopropylphosphoramidite (Compound 37)

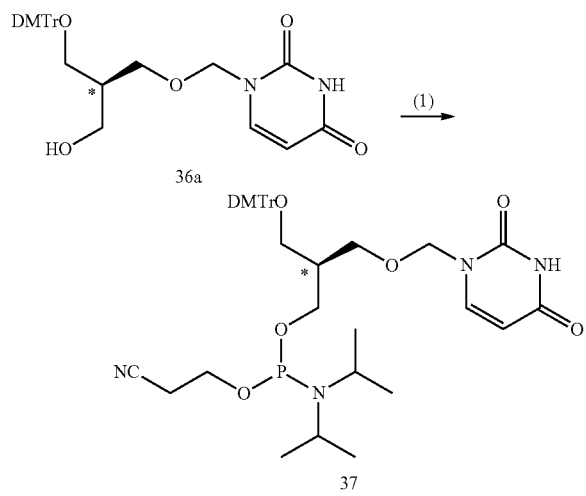

The compound 36a (120 mg, 0.225 mmol) obtained in Synthesis Example 8-(5) and DIPEA (0.23 mL, 1.35 mmol) were dissolved with methylene chloride (2.0 mL), and 2-cyanoethyl N,N-diisopropylchlorophosphoramidite (0.075 mL, 0.270 mmol) was added thereto under ice cooling and stirred for 1 hour. 2-Cyanoethyl N,N-diisopropylchlorophosphoramidite (0.013 mL, 0.045 mmol) was further added under ice cooling and stirred for 30 minutes. To the reaction solution was added a saturated sodium hydrogen carbonate aqueous solution and extracted with ethyl acetate. The organic phase was dried over anhydrous magnesium sulphate and filtered and the solvent was distilled off under reduced pressure. The residue was purified by silica gel column chromatography (n-heptane/ethyl acetate/0.5% TEA) to obtain the titled compound 37 (90 mg, 0.123 mmol).

$^1$H-NMR (400 MHz, CDCl$_3$) δ (ppm): 1.04-1.20 (m, 12H), 2.12-2.27 (m, 1H), 2.50-2.61 (m, 2H), 3.02-3.23 (m, 2H), 3.42-3.84 (m, 8H), 3.79 (s, 6H), 5.06 (s, 2H), 5.69 (d, J=8.2 Hz, 1H), 6.77-6.86 (m, 4H), 7.15-7.44 (m, 9H), 7.20 (d, J=8.2 Hz, 1H), 8.05 (br s, 1H).

Example 10

Synthesis of (R*)-3-[bis(4-methoxyphenyl)(phenyl)methoxy]-2-{[(2,4-dioxo-3,4-dihydropyrimidin-1(2H)-yl)methoxy]methyl}propyl(2-cyanoethyl)diisopropylphosphoramidite (Compound 38)

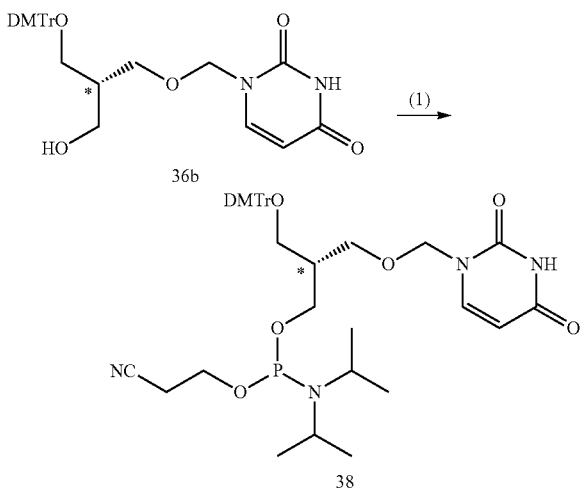

The compound 36b (135 mg, 0.253 mmol) obtained in Synthesis Example 8-(5) and DIPEA (0.26 mL, 1.52 mmol) were dissolved with methylene chloride (2.2 mL), and 2-cyanoethyl N,N-diisopropylchlorophosphoramidite (0.085 mL, 0.304 mmol) was added thereto under ice cooling and stirred for 1 hour. 2-Cyanoethyl N,N-diisopropylchlorophosphoramidite (0.011 mL, 0.051 mmol) was further added under ice cooling and stirred for 30 minutes. To the reaction solution was added a saturated sodium hydrogen carbonate aqueous solution and extracted with ethyl acetate. The organic phase was dried over anhydrous magnesium sulphate and filtered and the solvent was distilled off under reduced pressure. The residue was purified by silica gel column chromatography (n-heptane/ethyl acetate/0.5% TEA) to obtain the titled compound 38 (75 mg, 0.102 mmol).

$^1$H-NMR (400 MHz, CDCl$_3$) δ (ppm): 1.04-1.20 (m, 12H), 2.12-2.27 (m, 1H), 2.50-2.61 (m, 2H), 3.02-3.23 (m, 2H), 3.42-3.84 (m, 8H), 3.79 (s, 6H), 5.06 (s, 2H), 5.69 (d, J=8.2 Hz, 1H), 6.77-6.86 (m, 4H), 7.15-7.44 (m, 9H), 7.20 (d, J=8.2 Hz, 1H), 8.05 (br s, 1H).

Example 11

Synthesis of (S*)-4-(3-[bis(4-methoxyphenyl)(phenyl)methoxy]-2-{[(2,4-dioxo-3,4-dihydropyrimidin-1(2H)-yl)methoxy]methyl}propoxy)-4-oxobutanoate-CPG support

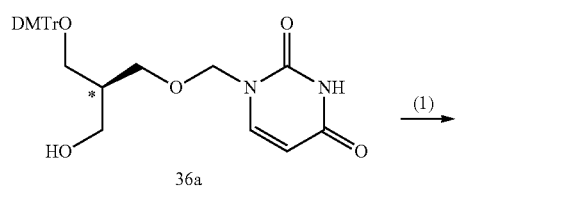

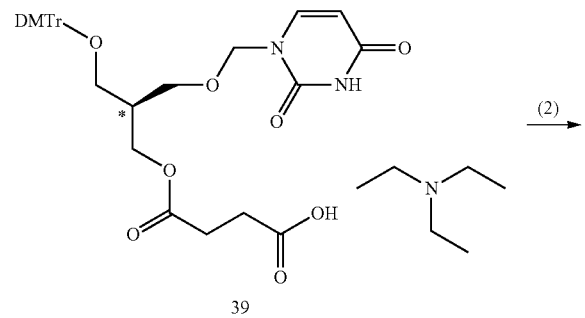

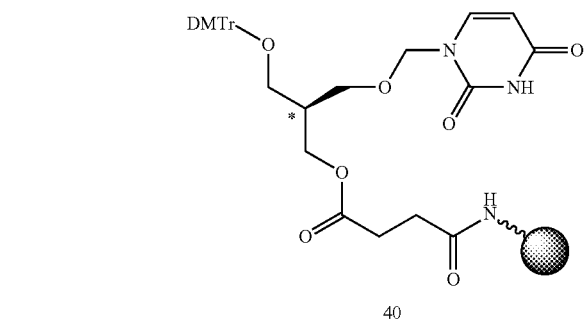

(1) Synthesis of triethylamine (S*)-4-(3-[bis(4-methoxyphenyl)(phenyl)methoxy]-2-{[(2,4-dioxo-3,4-dihydropyrimidin-1(2H)-yl)methoxy]methyl}propoxy)-4-oxobutanoate (Compound 39)

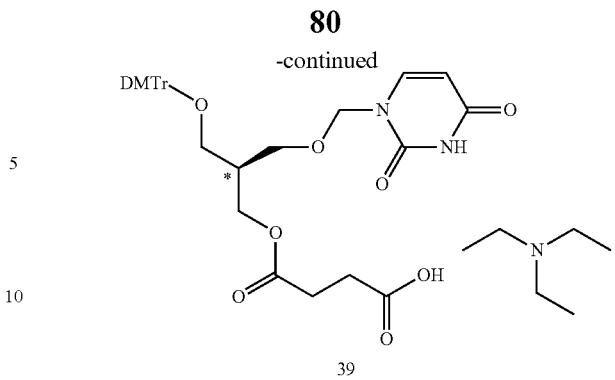

The compound 36a (35 mg, 0.066 mmol) obtained in Synthesis Example 8-(5) and DMAP (24 mg, 0.197 mmol) were dissolved with methylene chloride (0.65 mL), and succinic anhydride (13 mg, 0.13 mmol) was added thereto at room temperature and stirred for 16 hours. The reaction solution was purified by silica gel column chromatography (chloroform/methanol/0.5% TEA) to obtain the titled compound 39 (34 mg, 0.046 mmol).

$^1$H-NMR (400 MHz, CDCl$_3$) δ (ppm): 1.24 (t, J=7.2 Hz, 9H), 2.14-2.28 (m, 1H), 2.55 (br s, 4H), 2.98 (q, J=7.4 Hz, 6H), 3.07-3.17 (m, 2H), 3.55-3.64 (m, 2H), 3.79 (s, 6H), 4.07-4.27 (m, 2H), 5.05 (s, 2H), 5.71 (d, J=8.2 Hz, 1H), 6.78-6.85 (m, 4H), 7.14-7.44 (m, 9H), 7.19 (d, J=8.2 Hz, 1H), 8.29 (br s, 1H).

(2) Synthesis of (S*)-4-(3-[bis(4-methoxyphenyl)(phenyl)methoxy]-2-{[(2,4-dioxo-3,4-dihydropyrimidin-1(2H)-yl)methoxy]methyl}propoxy)-4-oxobutanoate-CPG support (CPG support 40)

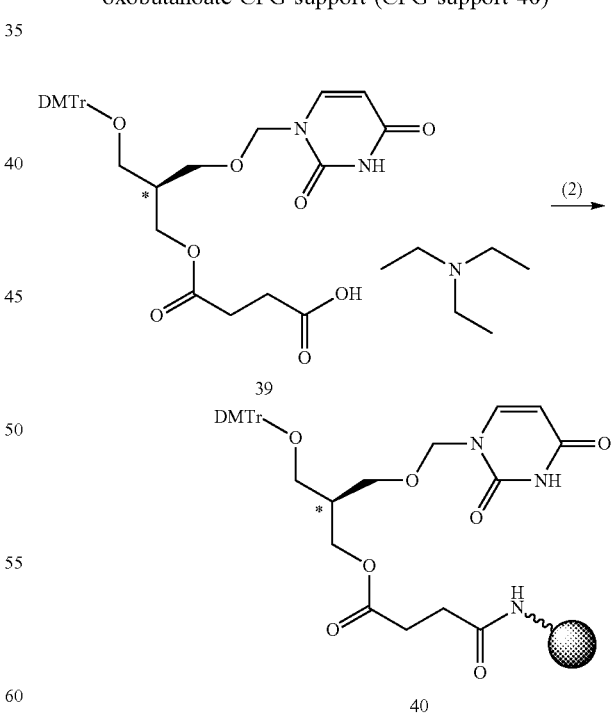

The compound 39 (33 mg, 0.045 mmol) obtained in Example 11-(1) and DIPEA (0.023 L, 0.135 mmol) were dissolved with acetonitrile (3.3 mL), and HBTU (34 mg, 0.090 mmol) was added thereto at room temperature and mildly stirred for 5 minutes. The CPG support (743 mg, 0.077 mmol) was promptly added at room temperature and mildly shaken for 16 hours. Shaking was terminated and the mixture was filtered through a glass filter. The residue was washed with methylene chloride, 20% methanol/methylene chloride, methylene chloride and diethyl ether in this order, and the obtained CPG support was dried under reduced pressure. The CPG support was suspended in pyridine (2.4 mL), and TEA (33 µL) and acetic anhydride (0.80 mL) were added thereto and mildly shaken at room temperature for 1 hour. To the suspension, methylene chloride was added, filtered and washed with methylene chloride, 20% methanol/methylene chloride, methylene chloride and diethyl ether in this order and the obtained CPG support was dried under reduced pressure to obtain the titled CPG support 40 (460 mg). The loading amount calculated from the absorbance after treatment with 5% dichloroacetic acid/1,2-dichloroethane was 62.2 µmol/g.

Example 12

(R*)-4-(3-[bis(4-methoxyphenyl)(phenyl)methoxy]-2-{[(2,4-dioxo-3,4-dihydropyrimidin-1(2H)-yl)methoxy]methyl}propoxy)-4-oxobutanoate-CPG support

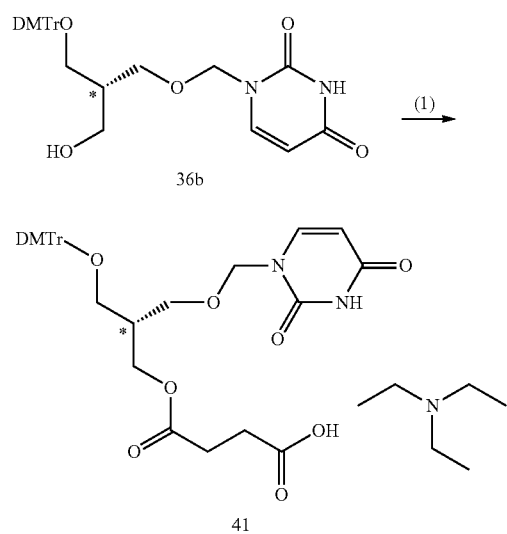

(1) Synthesis of triethylamine (R*)-4-(3-[bis(4-methoxyphenyl)(phenyl)methoxy]-2-{[(2,4-dioxo-3,4-dihydropyrimidin-1(2H)-yl)methoxy]methyl}propoxy)-4-oxobutanoate (Compound 41)

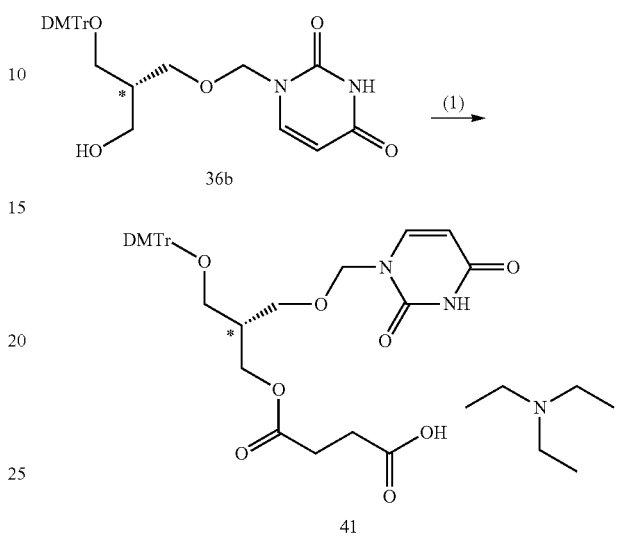

The compound 36b (35 mg, 0.066 mmol) obtained in Synthesis Example 8-(5) and DMAP (24 mg, 0.197 mmol) were dissolved with methylene chloride (0.65 mL), and succinic anhydride (13 mg, 0.13 mmol) was added at room temperature and stirred for 16 hours. The reaction solution was purified by silica gel column chromatography (chloroform/methanol/0.5% TEA) to obtain the titled compound 41 (38 mg, 0.052 mmol).

$^1$H-NMR (400 MHz, CDCl$_3$) δ (ppm): 1.24 (t, J=7.2 Hz, 9H), 2.14-2.28 (m, 1H), 2.55 (br s, 4H), 2.98 (q, J=7.4 Hz, 6H), 3.07-3.17 (m, 2H), 3.55-3.64 (m, 2H), 3.79 (s, 6H), 4.07-4.27 (m, 2H), 5.05 (s, 2H), 5.71 (d, J=8.2 Hz, 1H), 6.78-6.85 (m, 4H), 7.14-7.44 (m, 9H), 7.19 (d, J=8.2 Hz, 1H), 8.29 (br s, 1H).

(2) Synthesis of (R*)-4-(3-[bis(4-methoxyphenyl)(phenyl)methoxy]-2-{[(2,4-dioxo-3,4-dihydropyrimidin-1(2H)-yl)methoxy]methyl}propoxy)-4-oxobutanoate-CPG support (CPG support 42)

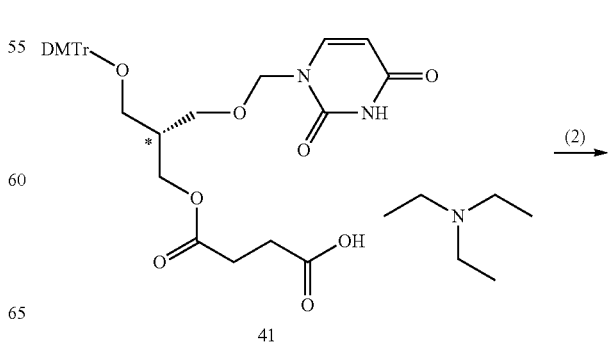

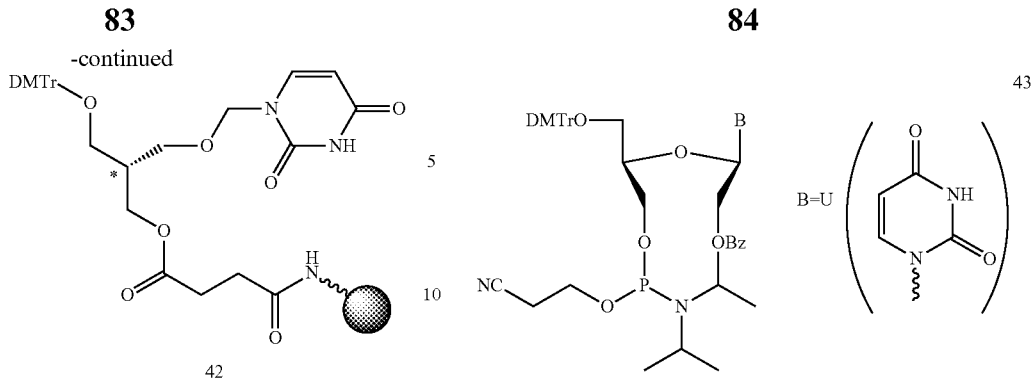

42

According to the method in Example 11-(2), the titled compound-CPG support 42 (550 mg) was obtained from the compound 41 (37 mg, 0.050 mmol) obtained in Example 12-(1), DIPEA (0.026 L, 0.151 mmol), HBTU (38 mg, 0.101 mmol), the CPG support (825 mg, 0.085 mmol), acetonitrile (3.7 mL), pyridine (2.7 mL), TEA (0.037 mL) and acetic anhydride (0.90 mL). The loading amount calculated from the absorbance after treatment with 5% dichloroacetic acid/1,2-dichloroethane was 60.5 μmol/g.

$^1$H-NMR (400 MHz, CDCl$_3$) δ (ppm): 1.24 (t, J=7.2 Hz, 9H), 2.14-2.28 (m, 1H), 2.55 (br s, 4H), 2.98 (q, J=7.4 Hz, 6H), 3.07-3.17 (m, 2H), 3.55-3.64 (m, 2H), 3.79 (s, 6H), 4.07-4.27 (m, 2H), 5.05 (s, 2H), 5.71 (d, J=8.2 Hz, 1H), 6.78-6.85 (m, 4H), 7.14-7.44 (m, 9H), 7.19 (d, J=8.2 Hz, 1H), 8.29 (br s, 1H).

Example 13, Comparative Example

Various siRNAs indicated in Table 1 below were synthesized using the modified nucleic acid monomer compounds produced in Examples 1 to 12, an UNA monomer compound represented by the following formula:

produced according to the method disclosed in NPL 2, an SNA monomer compound represented by the following formula:

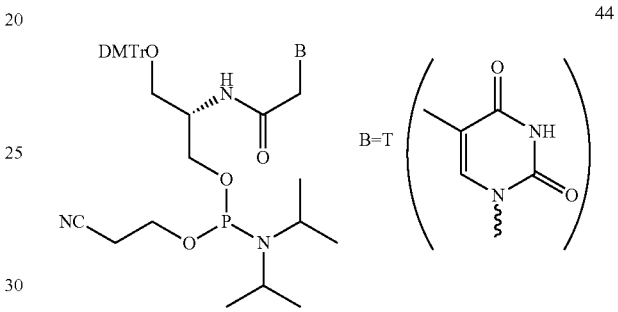

produced according to the method disclosed in NPL 3 (Supporting Information) and a nucleoside monomer having a ribose or deoxyribose by the improved solid phase phosphoramidite method using β-cyanoethylphosphoramidite (Nucleic Acids Research, 18(18), 5433-5441, (1990)).

TABLE 1

| Duplex ID | Firefly Target Position | Monomer No. | Sense | Antisense |
|---|---|---|---|---|
| #1 | A | G: 22 | GCUAUGGGCUGAAUACAAA (SEQ ID NO: 1) | UUUGUAUUCAGCCCAUAGC (SEQ ID NO: 2) |
| #2 | A | A: 27 | GCUAUGGGCUGAAUACAAA (SEQ ID NO: 3) | UUUGUAUUCAGCCCAUAGC (SEQ ID NO: 4) |
| #3 | A | G: 22<br>A: 27 | GCUAUGGGCUGAAUACAAA (SEQ ID NO: 5) | UUUGUAUUCAGCCCAUAGC (SEQ ID NO: 6) |
| #4 | A | C: 20<br>G: 22 | GCUAUGGGCUGAAUACAAA (SEQ ID NO: 7) | UUUGUAUUCAGCCCAUAGC (SEQ ID NO: 8) |
| #5 | A | A: 27 | GCUAUGGGCUGAAUACAAA (SEQ ID NO: 9) | UUUGUAUUCAGCCCAUAGC (SEQ ID NO: 10) |
| #6 | B | T: 8<br>C: 20 | CGAUCAUACAAAAGAUCAT (SEQ ID NO: 11) | AUGAUCUUUUGUAUGAUCG (SEQ ID NO: 12) |
| #7 | B | C: 20<br>G: 22 | CGAUCAUACAAAAGAUCAU (SEQ ID NO: 13) | AUGAUCUUUUGUAUGAUCG (SEQ ID NO: 14) |
| #8 | B | T: 8<br>C: 20<br>G: 22<br>A: 27 | CGAUCAUACAAAAGAUCAT (SEQ ID NO: 15) | AUGAUCUUUUGUAUGAUCG (SEQ ID NO: 16) |
| #9 | B | T: 8 | CGAUCAUACAAAAGAUCAUtt (SEQ ID NO: 17) | AUGAUCUUUUGUAUGAUCGtt (SEQ ID NO: 18) |

TABLE 1-continued

| Du-plex ID | Firefly Target Position | Monomer No. | Sense | Antisense |
|---|---|---|---|---|
| #10 | — | U: 18 | GGAUfCfAUfCfUfCfAAGUf CfUfUfACf (SEQ ID NO: 19) | GUfAAGACfUfUfGAGAUfGA UfCfCf<u>UU</u> (SEQ ID NO: 20) |

In the table, capital letters represent ribonucleotides, the lower case t represents a deoxyribonucleotide, Xf (wherein X is C or U) represents a 2'-fluororibonucleotide, and an underlined base indicates that a modified nucleic acid monomer compound of the compound number (Monomer No.) produced in Examples above was incorporated in the oligomer. For example, it is indicated that the monomer compound 22 produced in Example 5 is incorporated in the position of the underlined first base G in the sense strand of Duplex ID #1. In present Examples, the modified nucleic acid monomer compounds (i.e., compounds 8, 18, 20, 22 and 27) used for incorporation into oligomers have hydrogen atoms ($R^2$ to $R^6$) in amino groups or hydroxy groups of nucleobases protected with protective groups, while in siRNAs after incorporation into oligomers, the protective groups of the amino groups or hydroxy groups in the nucleobases are all deprotected (i.e. $R^2$ to $R^6$ are all hydrogen atoms), and the structural units 8' ((a) or (b)), 18' ((a) or (b)), 20', 22' and 27' ((a) or (b)) indicated below derived from the compounds 8, 18, 20, 22 and 27 are respectively incorporated. Specifically, in case of other than 3'-termini of oligomers, the structural units 8'(a), 18'(a), 20', 22' and 27'(a) are incorporated and in case of 3'-termini of oligomers (specifically, the compound 27 at 3'-termini of sense strands of #2, #3 and #5, the compound 8 at 3'-termini of sense strands of #6 and #8, and the compound 18 at the 3'-terminal of the antisense strand of #10), structural units 27'(b), 8'(b) and 18'(b) without phosphate groups are incorporated.

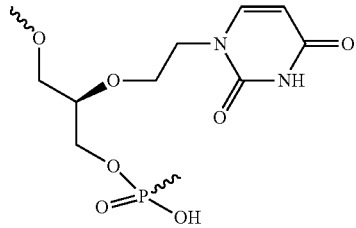

18'(a)

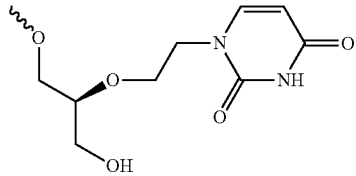

18'(b)

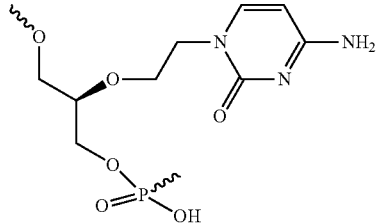

20'

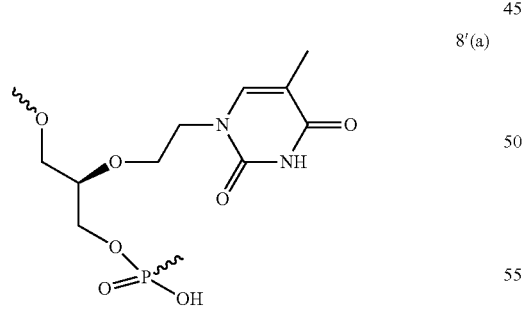

8'(a)

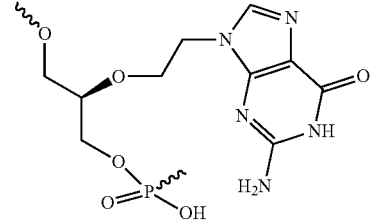

22'

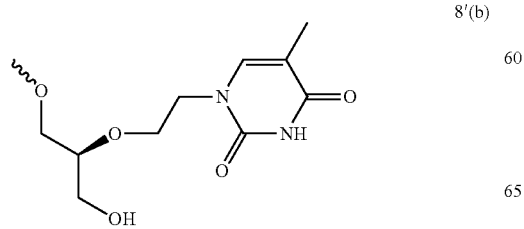

8'(b)

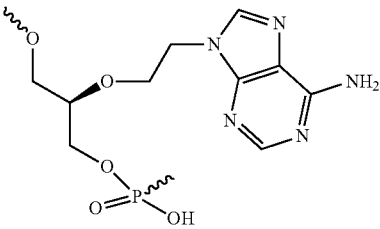

27'(a)

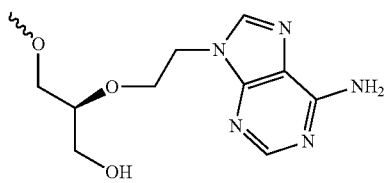

27'(b)

In the table, Firefly Target Position indicates the position of the target sequence in the Firefly Luciferase expression vector, and in the vectors used in Test Example 1, A is 704 and B is 929.

The results for the synthesized siRNAs of molecular weight ([M-H]$^-$) measurement by MALDI-TOF-MS (Tanaka, K., et al. Rapid Commun. Mass Spectrom 1988, 2: 151-153) are indicated in Table 2.

TABLE 2

| Duplex ID | Sense [M − H]$^-$ | Antisense [M − H]$^-$ |
|---|---|---|
| #1 | 6093.0 | 5957.0 |
| #2 | 6093.0 | 5957.0 |
| #3 | 6080.8 | 5959.6 |
| #4 | 6083.2 | 5957.0 |
| #5 | 6078.5 | 5957.0 |
| #6 | 6023.2 | 5999.8 |
| #7 | 6006.7 | 5999.8 |
| #8 | 5994.4 | 5999.8 |
| #9 | 6644.3 | 6607.5 |
| #10 | 6004.1 | 6686.1 |

Comparative Examples

Control siRNAs having sense strands and antisense strands indicated in Table 3 below were synthesized also by the phosphoramidite method without using the modified nucleic acid monomers produced in Examples 1 to 12.

Control siRNAs

In the table, capital letters represent ribonucleotides, the lower case t represents a deoxyribonucleotide, the lower case u represents a 2'-O-methylribonucleotide, Xf (wherein X is C or U) represents a 2'-fluororibonucleotide, ^ represents a phosphorothioate bond, and an underlined base indicates that a modified nucleic acid monomer compound of the compound number (Monomer No.) produced in Examples above was incorporated in the oligomer. In siRNAs after incorporation into oligomers, the protective groups of the amino groups or hydroxy groups in the nucleic acid monomer compounds are all deprotected and structural units 43' and 44' indicated below derived from the compounds 43 and 44 are respectively incorporated.

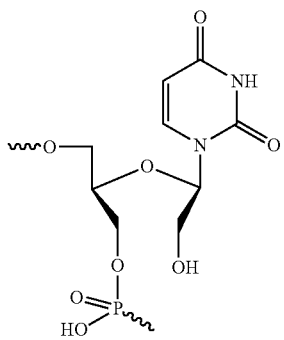

43'

TABLE 3

| Duplex ID | Firefly Target Position | Monomer | Sense | Antisense |
|---|---|---|---|---|
| Cont-1 | A | RNA | GCUAUGGGCUGAAUACAAA (SEQ ID NO: 21) | UUUGUAUUCAGCCCAUAGC (SEQ ID NO: 22) |
| Cont-2 | B | RNA | CGAUCAUACAAAAGAUCAUtt (SEQ ID NO: 23) | AUGAUCUUUUGUAUGAUCGtt (SEQ ID NO: 24) |
| Cont-3 | B | RNA | CGAUCAUACAAAAGAUCAU (SEQ ID NO: 25) | AUGAUCUUUUGUAUGAUCG (SEQ ID NO: 26) |
| Cont-4 | A | RNA | GCUAUGGGCUGAAUACAAAU^U (SEQ ID NO: 27) | UUUGUAUUCAGCCCAUAGCU^U (SEQ ID NO: 28) |
| Cont-5 | — | 2'-OMe-RNA | GGAUfCfAUfCfUfCfAAGUfCfUfUfACf (SEQ ID NO: 29) | GUfAAGACfUfUfGAGAUfGAUfCfCfuu (SEQ ID NO: 30) |
| Cont-6 | B | U: 43 | CGAUCAUACAAAAGAUCAUtt (SEQ ID NO: 31) | AUGAUC<u>U</u>UUUGUAUGAUCGtt (SEQ ID NO: 32) |
| Cont-7 | B | T: 44 | CGAUCAUACAAAAGAUCAUtt (SEQ ID NO: 33) | AUGAUC<u>T</u>UUUGUAUGAUCGtt (SEQ ID NO: 34) |

44'

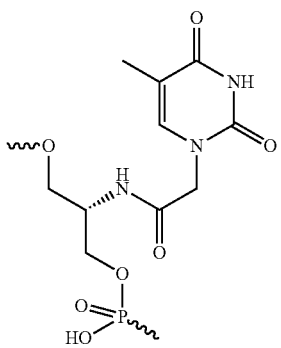

The synthesized control siRNAs were measured for the molecular weight ([M-H]⁻) by MALDI-TOF-MS. The results are indicated in Table 4.

TABLE 4

| Duplex ID | Sense [M − H]⁻ | Antisense [M − H]⁻ |
| --- | --- | --- |
| Cont-1 | 6110.2 | 5960.5 |
| Cont-2 | 6644.2 | 6609.0 |
| Cont-3 | 6034.2 | 5998.8 |
| Cont-4 | 6738.6 | 6589.3 |
| Cont-5 | 6003.7 | 6741.2 |
| Cont-6 | 6644.6 | 6613.1 |
| Cont-7 | 6644.1 | 6621.6 |

Test Examples

The produced various siRNAs were then evaluated as indicated below.

1) Evaluation of In Vitro Activity of siRNAs Using Dual-Luciferase Reporter Assay With the siRNAs (final concentration: 1 to 10 nM/well) indicated in Table 1 and Table 3, a Firefly Luciferase expression vector pGL4.13 (Promega) and a *Renilla* Luciferase expression vector pGL4.73 (Promega), human embryonic kidney cell line HEK293 cells (ATCC) 4.0×10⁴ cells/100 µL/well were reverse-transfected in a 96-well plate using Lipofectamine 2000 reagent (Invitrogen). After overnight incubation, Firefly Luciferase activity and *Renilla* Luciferase activity were measured using the Dual-Glo Luciferase Assay kit (Promega) according to the instruction attached to the kit. With the Luciferase activity (Firefly/ *Renilla* Intensity) of the cells without using siRNA as a control being regarded as 100%, Luciferase activities (relative values) (i.e., Relative Luciferase Activity) of the cells to which various siRNAs were introduced were calculated. The results are indicated in Table 5, Table 6, Table 7, FIG. 1, FIG. 2 and FIG. 3.

TABLE 5

| Duplex ID | Firefly Target Position | Monomer | siRNA 10 nM | siRNA 1 nM |
| --- | --- | --- | --- | --- |
| | | | \multicolumn{2}{c}{Relative Luciferase Activity (% vs control = 100%)} | |
| Cont-1 | A | RNA | 13% | 24% |
| #1 | A | G: 22 | 13% | 26% |
| #2 | A | A: 27 | 11% | 21% |

TABLE 5-continued

| Duplex ID | Firefly Target Position | Monomer | siRNA 10 nM | siRNA 1 nM |
| --- | --- | --- | --- | --- |
| #3 | A | G: 22 A: 27 | 9.9% | 22% |
| #4 | A | C: 20 G: 22 | 9.4% | 23% |

TABLE 6

| Duplex ID | Firefly Target Position | Monomer | siRNA 10 nM | siRNA 1 nM |
| --- | --- | --- | --- | --- |
| Cont-3 | B | RNA | 9.2% | 20% |
| #6 | B | T: 8 C: 20 | 6.4% | 22% |
| #7 | B | C: 20 G: 22 | 7.0% | 19% |
| #8 | B | T: 8 C: 20 G: 22 A: 27 | 7.7% | 20% |

TABLE 7

| Duplex ID | Firefly Target Position | Monomer | siRNA 10 nM | siRNA 1 nM |
| --- | --- | --- | --- | --- |
| Cont-2 | B | RNA | 17% | 32% |
| Cont-6 | B | U: 43 | 26% | 45% |
| Cont-7 | B | T: 44 | 8.5% | 19% |
| #9 | B | T: 8 | 6.7% | 12% |

2) Nuclease resistance test

Nuclease resistance was evaluated for a siRNA made of natural nucleotides containing riboses as sugar and a siRNA containing some modified nucleotides of the present invention substituting the natural nucleotides.

The siRNAs (final concentration: 0.5 µM) and 3'-exonuclease which was a snake venom phosphodiesterase SVPD (Sigma-Aldrich) were mixed in a solution containing Tris-HCl (40 mM, pH 8.5), NaCl (100 mM) and MgCl₂ (15 mM). After being left to stand at 37° C. for 60 minutes, the reaction was quenched by adding the equivalent amount of EDTA (0.5 M). The solution was electrophoresed using a Tris-Glycine buffer and a native gel e-PAGEL (ATTO) and nucleic acid was then stained with SYBR Green II RNA gel stain (Invitrogen) and subjected to image analysis using LAS-4000 (Fujifilm). The results are shown in [FIG. 4].

As indicated in the results in [FIG. 4], the siRNA containing the monomer of the present invention has resistance to 3'-exonuclease compared to the siRNA prepared from normal ribonucleotides, and thus suppression of decomposition in vivo may be expected.

3) Evaluation of siRNA In Vivo Activity i) Preparation of siRNA-LNP

Various siRNAs were dissolved with 25 mM sodium acetate pH 4.0 to prepare siRNA dilutions with the concentration of 0.053 mg/mL. An ionised lipid, 1-(2-octylcyclopropyl)heptadecan-8-yl 1-methylpiperidine-4-carboxylate, DSPC (Nippon Fine Chemical Co., Ltd.), cholesterol (Nippon Fine Chemical Co., Ltd.) and MPEG 2000-DMG (NOF Corporation) were dissolved with ethanol at a molar ratio of 60/8.5/30/1.5. The siRNA dilution and the lipid solution at a flow rate of 3 mL/min and 1 mL/min, respectively, were mixed at the weight ratio between siRNA and lipids of 0.06 to obtain lipid nanoparticles (LNPs). The outer solution of the obtained LNP aqueous solution was replaced by PBS pH 7.4 by dialysis using 100 kD Float-A-Lyzer G2 (SPECTRUM). After the dialysis, filter sterilisation was performed and the LNPs were used for experiments. The siRNA concentration and the encapsulation rate were measured using Quant-iT RiboGreen RNA Reagent (Invitrogen) (the siRNA concentration measured after dilution with RNase Free Water was regarded as the siRNA in the LNP outer solution and the siRNA concentration measured after dilution with 1% Triton X-100 was regarded as the total siRNA concentration in the preparation, thereby calculating the encapsulation rate). The average particle diameter was measured on a particle diameter analyser (manufactured by Malvem, Zetasizer Nano ZS). The measurement results are shown in Table 8.

TABLE 8

Properties of LNPs containing modified Factor VII siRNA

| Duplex ID | Particle diameter | Index of dispersion | siRNA encapsulation rate |
|---|---|---|---|
| Cont-5 | 73 nm | 0.14 | 97% |
| #10 | 66 nm | 0.14 | 98% | ii) Evaluation of siRNA In Vivo Activity Targeting Blood Coagulation Factor VII

LNPs containing Factor VII siRNA encapsulated therein were administered to mice (n=3 per group) via the tail vein, and the blood was collected at 24 hours after administration under anaesthesia. The plasma was separated from the blood by centrifugation and the plasma Factor VII protein level was quantified with the BIOPHEN FVII kit (Aniara). The Factor VII protein level (relative value) ("Relative Factor VII protein level in mouse plasma") of the LNP administration group was calculated with the Factor VII protein level in the plasma of mice without treatment as control being 100%. The results are shown in Table 9.

TABLE 9 in vivo activity in mice using modified Factor VII siRNA

| | Relative Factor VII protein level in mouse plasma (% vs control = 100%) | |
|---|---|---|
| Duplex ID | siRNA 0.2 mg/kg | siRNA 0.05 mg/kg |
| Cont-5 | 1.4% | 6.7% |
| #10 | <1.0% | 5.2% |

As indicated in the results in Table 9, the siRNA formed with the monomer of the present invention showed the target protein silencing effect upon intravenous administration of the LNP preparation to mice that was equivalent to or above the effect from the siRNA prepared with ribonucleotides containing 2'-O-methylribose, and thus may be applicable to pharmaceutical preparations.

The scope of the present invention is not limited to the above descriptions, and may be appropriately modified and implemented in embodiments other than the above without departing from the purpose of the present invention. All references and publications described herein are incorporated herein by reference in the entirety thereof regardless of the purpose thereof. The present specification encompasses the entire disclosure in the claims and specification of Japanese Patent Application No. 2017-118572 (filed on 16 Jun. 2017) which serves as the basis of priority claim of the present application.

INDUSTRIAL APPLICABILITY

The present invention provides a modified nucleic acid monomer compound and an oligonucleic acid analogue containing the monomer compound as a building block. The oligonucleic acid analogue has excellent biological stability and/or target gene silencing activity, and thus is useful for therapy and diagnosis.

The invention claimed is:

1. An oligonucleic acid analogue comprising one or more partial structures represented by the following formula (IX) or a salt thereof,

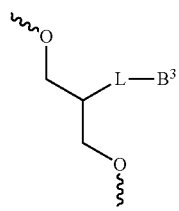

(IX)

wherein:

B³ represents a nucleobase; and

L represents —OCH₂CH₂— or —CH₂OCH₂—; provided that when two or more partial structures are included, B³ and L in the partial structures may be respectively the same or different.

2. The oligonucleic acid analogue according to claim 1 or a salt thereof, wherein B³ is a nucleobase selected from the following formulae (II)', (III)', (IV)' and (V)':

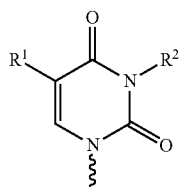

(II)'

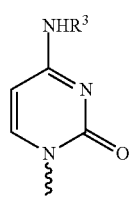

(III)'

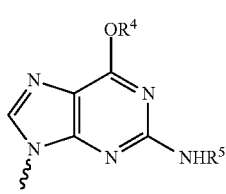

(IV)'

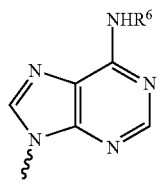

(V)' wherein:

R¹ represents a hydrogen atom or methyl;

R² and R⁴ each independently represent a hydrogen atom, $C_{1-6}$ alkyl, $C_{1-6}$ alkoxy, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl, $C_{6-14}$ arylsulphonyl or a protective group; and R³, R⁵ and R⁶ each independently represent a hydrogen atom, $C_{1-6}$ alkyl, $C_{3-6}$ alkenyl, $C_{3-6}$ alkynyl, $C_{1-6}$ alkyl-carbonyl, $C_{1-6}$ alkylsulphonyl, $C_{6-14}$ aryloxy-carbonyl, $C_{6-14}$ aryl-carbonyl, $C_{6-14}$ arylsulphonyl or a protective group.

3. The oligonucleic acid analogue according to claim 2 or a salt thereof, wherein the protective groups in R², R³, R⁵ and R⁶ are each independently selected from a carbamate protective group, an acyl protective group, an imide protective group and a benzyl protective group, and the protective group in R⁴ is selected from a silyl protective group, a trityl protective group, a heterocyclic protective group, a benzyl protective group, an aliphatic acyl protective group, an aromatic acyl protective group, an ether protective group, a carbamoyl protective group and an alkoxycarbonyl protective group.

4. The oligonucleic acid analogue according to claim 2 or a salt thereof, wherein B³ is selected from the following formulae (X), (XI), (XII) and (XIII):

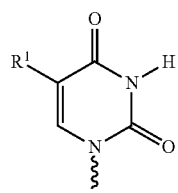

(X)

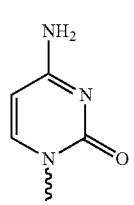

(XI)

-continued

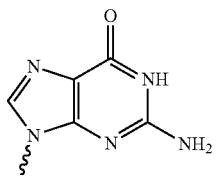
(XII)

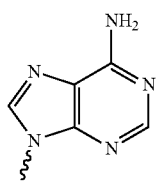
(XIII)

wherein R¹ is as defined above.

5. The oligonucleic acid analogue according to claim 2 or a salt thereof, wherein L is —OCH₂CH₂—.

6. The oligonucleic acid analogue according to claim 2 or a salt thereof, wherein the oligonucleic acid analogue contains 4 to 100 nucleobase units in total per strand.

7. The oligonucleic acid analogue according to claim 2 or a salt thereof, wherein the oligonucleic acid analogue contains 4 to 30 nucleobase units in total per strand.

* * * * *